United States Patent
Kim et al.

(10) Patent No.: US 9,871,207 B2
(45) Date of Patent: Jan. 16, 2018

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Wonsam Kim, Cheonan-si (KR); Sunhee Lee, Cheonan-si (KR); Hyeryeong Kim, Cheonan-si (KR); Jaewan Jang, Cheonan-si (KR); Yuri Kim, Wonju-si (KR); Junghwan Park, Seoul (KR); Seongje Park, Busan (KR)

(73) Assignee: DUK SAN NEOLUX CO., LTD., Cheonan-si, Chungcheongnam-do (KR)

( * ) Notice: Subject to any disclaimer, the term of this patent is extended or adjusted under 35 U.S.C. 154(b) by 131 days.

(21) Appl. No.: 14/766,183

(22) PCT Filed: Feb. 5, 2014

(86) PCT No.: PCT/KR2014/000970
§ 371 (c)(1),
(2) Date: Aug. 6, 2015

(87) PCT Pub. No.: WO2014/123348
PCT Pub. Date: Aug. 14, 2014

(65) Prior Publication Data
US 2015/0380661 A1   Dec. 31, 2015

(30) Foreign Application Priority Data
Feb. 7, 2013   (KR) .................. 10-2013-0014167

(51) Int. Cl.
| | |
|---|---|
| H01L 51/00 | (2006.01) |
| C07D 495/04 | (2006.01) |
| C07D 409/14 | (2006.01) |
| C07D 209/56 | (2006.01) |
| C07D 209/96 | (2006.01) |
| C07D 487/04 | (2006.01) |
| C07D 493/04 | (2006.01) |
| C09K 11/06 | (2006.01) |
| C07D 403/04 | (2006.01) |
| C07D 403/14 | (2006.01) |
| C07D 491/048 | (2006.01) |
| C07D 307/93 | (2006.01) |
| C07D 333/78 | (2006.01) |
| C07D 209/94 | (2006.01) |
| C07C 13/62 | (2006.01) |
| C07C 13/72 | (2006.01) |
| H01L 51/50 | (2006.01) |

(52) U.S. Cl.
CPC .......... $H01L\ 51/0071$ (2013.01); $C07C\ 13/62$ (2013.01); $C07C\ 13/72$ (2013.01); $C07D\ 209/56$ (2013.01); $C07D\ 209/94$ (2013.01); $C07D\ 209/96$ (2013.01); $C07D\ 307/93$ (2013.01); $C07D\ 333/78$ (2013.01); $C07D\ 403/04$ (2013.01); $C07D\ 403/14$ (2013.01); $C07D\ 409/14$ (2013.01); $C07D\ 487/04$ (2013.01); $C07D\ 491/048$ (2013.01); $C07D\ 493/04$ (2013.01); $C07D\ 495/04$ (2013.01); $C09K\ 11/06$ (2013.01); $H01L\ 51/0072$ (2013.01); $H01L\ 51/0074$ (2013.01); $C07C\ 2603/54$ (2017.05); $C07C\ 2603/94$ (2017.05); $C09K\ 2211/1007$ (2013.01); $C09K\ 2211/1033$ (2013.01); $C09K\ 2211/1037$ (2013.01); $C09K\ 2211/1044$ (2013.01); $C09K\ 2211/1092$ (2013.01); $H01L\ 51/5016$ (2013.01); $Y02E\ 10/549$ (2013.01)

(58) Field of Classification Search
None
See application file for complete search history.

(56) References Cited

U.S. PATENT DOCUMENTS

| | | |
|---|---|---|
| 2010/0117064 A1 | 5/2010 | Lee et al. |
| 2010/0244008 A1 | 9/2010 | Lee et al. |
| 2012/0292603 A1 | 11/2012 | Kwak et al. |
| 2013/0001528 A1 | 1/2013 | Chang et al. |

FOREIGN PATENT DOCUMENTS

CN         101747335 A   *   6/2010

OTHER PUBLICATIONS

Machine English translation of Li et al. (CN 101747335 A). Jun. 12, 2017.*

* cited by examiner

*Primary Examiner* — J. L. Yang
(74) *Attorney, Agent, or Firm* — Vorys, Sater, Seymour and Pease LLP; Mih Suhn Koh

(57) ABSTRACT

The present invention provides a novel compound capable of improving light emitting efficiency, stability, and lifespan of the element, an organic element using the same, and an electric device for the same.

8 Claims, 1 Drawing Sheet

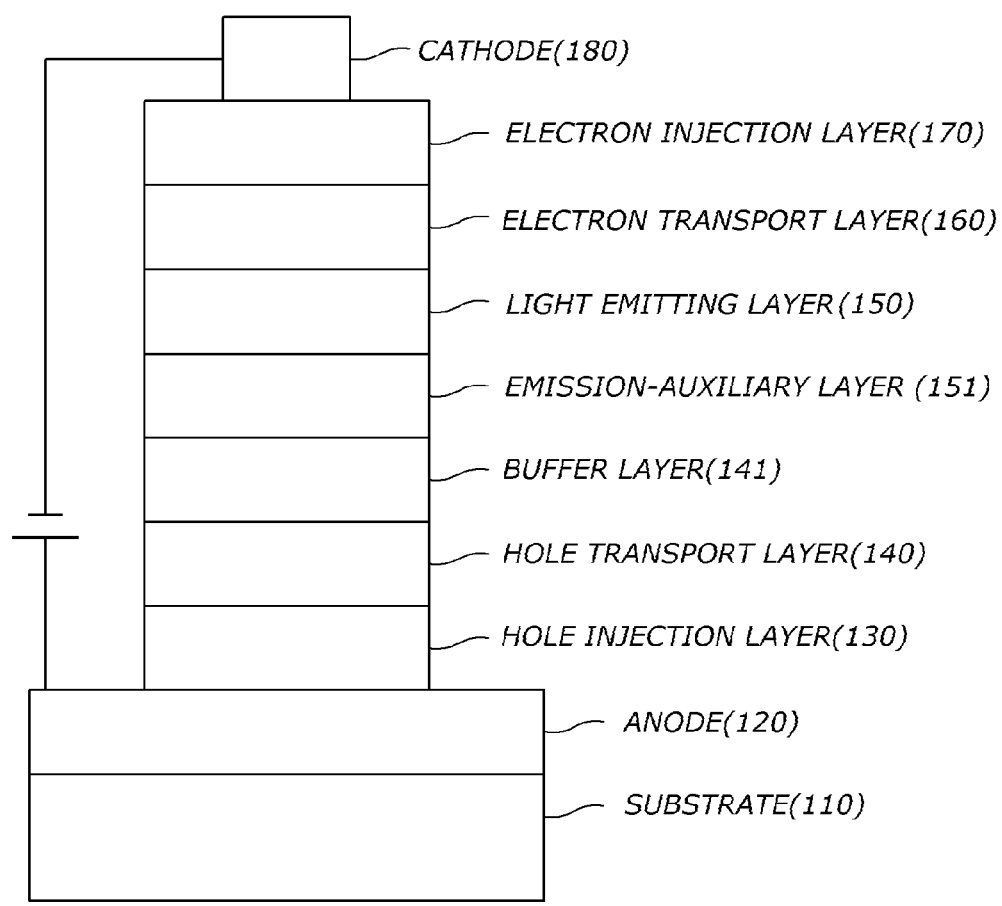

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application claims priority from and the benefit under 35 §119(a) of Korean Patent Application No. 10-2013-0014167, filed on Feb. 7, 2013, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

Meanwhile, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, alight emitting material, an electron transport material, an electron injection material, or the like, by a stable and efficient material. However, such a stable and efficient organic material layer material for an organic electric element has not yet been fully developed.

Accordingly, there is a continuous need to develop new materials for an organic material layer.

SUMMARY

In order to solve one or more of the above-mentioned problems occurring in the prior art, an aspect of the present invention is to provide a compound which allows an organic electric element to have high luminous efficiency, low driving voltage and high heat-resistant and to be improved in color purity and life span, an organic electric element using the same, and an electronic device including the organic electric element.

In accordance with an aspect of the present invention, there is provided compounds represented by the formula below.

[Formula 1]

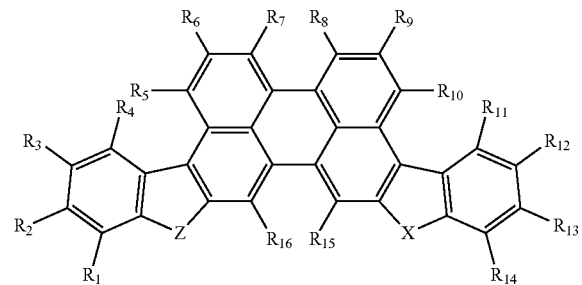

In another aspect of the present invention, there are provided organic electric elements using the compound represented by the formula above and electronic devices including the organic electric element.

By using the compound according to embodiments of the present invention, an organic electric element according to one or more embodiments of the present invention not only has high luminous efficiency, low driving voltage and high heat-resistant and, but can also be significantly improved in color purity, luminous efficiency, and life span.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component (s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine (F), chlorine (Cl), bromine (Br), or iodine(I).

Unless otherwise stated, the term "alkyl" or "alkyl group" as used herein has, but not limited to, 1 to 60 carbon atoms.

Unless otherwise stated, the term "alkenyl" or "alkynyl" as used herein has, but not limited to, double or triple bonds of 2 to 60 carbon atoms Unless otherwise stated, the term "cycloalkyl" as used herein means, but not limited to, alkyl forming a ring having 3 to 60 carbon atoms.

Unless otherwise stated, the term "alkoxy group" as used herein has, but not limited to, 1 to 60 carbon atoms.

Unless otherwise stated, the term "aryl group" or "arylene group" as used herein has, but not limited to, 6 to 60 carbon atoms.

Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group.

Unless otherwise stated, the term "heterocyclic alkyl" or "heterocyclic group" as used herein contains one or more heteroatoms, but not limited to, has 2 to 60 carbon atoms, includes both monocyclic and polycyclic rings, may be formed in conjuction with an adjacent group. Also, the heterocyclic group may mean an alicyclic and/or aromatic group containing heteroatoms.

Unless otherwise stated, the term "heteroatoms" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer formed on at least one of the sides the first and second electrodes, which is a side opposite to the organic material layer.

The inventive compound employed in the organic material layer may be used as materials of the hole injection layer 130, the hole transport layer 140, the electron transport layer 160, the electron injection layer 170, a host material or a dopant material of the light emitting layer 150, or a capping layer material.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

Further, the organic electric element according to an embodiment of the present invention may be anyone of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

[Formula 1]

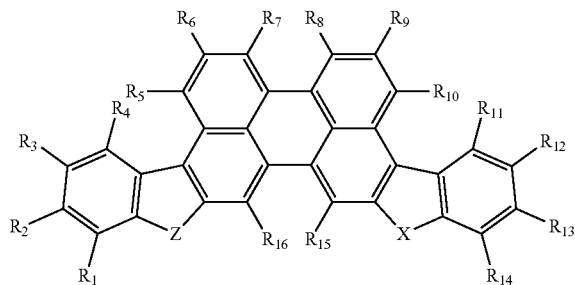

In Formula 1 above, $R_1$ to $R_{16}$ may be i) independently selected from the group consisting of hydrogen, deuterium, halogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, -L-N($Ar_1$) ($Ar_2$) and a fluorenyl group, or ii) any two adjacent groups can be independently linked together to form at least one fused ring. Here, remaining groups not forming a ring can be as defined above i).

Herein, 'adjacent group' means neighboring groups such as $R_1$ and $R_2$, $R_2$ and $R_3$, $R_3$ and $R_4$, and fused ring means monocycle or polycycle, saturated or unsaturated ring, aromatic or aliphatic ring, hetero ring. Also, fused ring may be substituted or unsubstituted rings.

X and Z may be the same or different, indepantantly N(Ar), S, O or C(R') (R"). Ar may be selected from the group containing of a $C_6$-$C_{60}$ aryl group, a $C_2$-$C_{60}$ heterocyclic group containing at least one heteroatom selected from the group consisting of O, N, S, Si and P, $C_1$-$C_{50}$ alkyl group, $C_2$-$C_{20}$ alkenyl group, fluorenyl group, $C_1$-$C_{30}$ alkoxy group, and -$L_1$-N($Ar_3$) ($Ar_4$).

L and $L_1$ may be independently selected from the group consisting of a single bond, a $C_6$-$C_{60}$ arylene group, a fluorenylen group, and a bivalent aliphatic hydrocarbon group. With the provisos that, 'single bond' means abescnt of L and $L_1$. On the other hands, L and $L_1$ is an arylene group, a heteroarylene group, a fluorentlene group, and a bivalent aliphatic hydrocarbon group, it may be substituted one or more substituted group selects from the group consisting a nitro group, a cyano group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group and an amino group.

$Ar_1$ to $Ar_4$ may be independently selected from the group consisting of a $C_6$-$C_{60}$ aryl group, a $C_2$-$C_{60}$ heterocyclic group containing at least one heteroatom selected from the group consisting of O, N, S, Si, and P, and $C_1$-$C_{50}$ alkyl group, $C_2$-$C_{20}$ alkenyl group, $C_1$-$C_{30}$ alkoxy group, fluorenyl group.

R' and R" may be independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and $C_1$-$C_{50}$ alkyl group.

When $R_1$ to $R_{16}$, Ar, $Ar_1$ to $Ar_4$, R' and R" are an aryl group, $R_1$ to $R_{16}$, Ar, $Ar_1$ to $Ar_4$, R' and R" may be substituted by one or more substuents selected from the group of consistion of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

When $R_1$ to $R_{16}$, Ar, $Ar_1$ to $Ar_4$, R' and R" are a hetero ring, $R_1$ to $R_{16}$, Ar, $Ar_1$ to $Ar_4$, R' and R" may be substituted by one or more substuents selected from the group of consisting of deuterium, halogen, a silane group, a cyano group, a nitro group, a $C_1$-$C_{20}$ alkoxyl group, a $C_1$-$C_{20}$ alkyl group, a $C_2$-$C_{20}$ alkenyl group, a $C_6$-$C_{20}$ aryl group, a aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

When $R_1$ to $R_{16}$, Ar, $Ar_1$ to $Ar_4$, R' and R" are a fluorenyl group, $R_1$ to $R_{16}$, Ar, $Ar_1$ to $Ar_4$, R' and R" may be substituted by one or more substuents selected from the group of consisting of deuterium, halogen, a silane group, a cyano group, a $C_1$-$C_{20}$ alkyl group, a $C_2$-$C_{20}$ alkenyl group, a $C_6$-$C_{20}$ aryl group, a aryl group substituted by deuterium, a $C_2$-$C_{20}$ heterocyclic group, a $C_3$-$C_{20}$ cycloalkyl group.

When $R_1$ to $R_{16}$, Ar, $Ar_1$ to $Ar_4$, R' and R" are an alkyl group, $R_1$ to $R_{16}$, Ar, $Ar_1$ to $Ar_4$, R' and R" may be substituted by one or more substuents selected from the group of consisting of halogen, a silane group, a boron group, a cyano group, a $C_1$-$C_{20}$ alkoxyl group, a $C_1$-$C_{20}$ alkyl group, a $C_2$-$C_{20}$ alkenyl group, a $C_6$-$C_{20}$ aryl group, a aryl group substituted by deuterium, a $C_2$-$C_{20}$ heterocyclic group, a $C_7$-$C_{20}$ arylalkyl group and a $C_8$-$C_{20}$ arylalkenyl group.

When Ar, $Ar_1$ to $Ar_4$ are an alkenyl group, Ar, $Ar_1$ to $Ar_4$ may be substituted by one or more substuents selected from the group of consisting of deuterium, halogen, a silane group, a cyano group, a $C_1$-$C_{20}$ alkoxyl group, a $C_1$-$C_{20}$ alkyl group, a $C_2$-$C_{20}$ alkenyl group, a $C_6$-$C_{20}$ aryl group, a aryl group substituted by deuterium, a $C_2$-$C_{20}$ heterocyclic group, a $C_3$-$C_{20}$ cycloalkyl group, a $C_7$-$C_{20}$ arylalkyl group and a $C_8$-$C_{20}$ arylalkenyl group.

When Ar, $Ar_1$ to $Ar_4$ are an alkoxyl group, Ar, $Ar_1$ to $Ar_4$ may be substituted by one or more substuents selected from the group of consisting of deuterium, halogen, a silane group, a $C_1$-$C_{20}$ alkyl group, a $C_6$-$C_{20}$ aryl group, a aryl group substituted by deuterium, a $C_2$-$C_{20}$ heterocyclic group, a $C_3$-$C_{20}$ cycloalkyl group.

Specially, Formula 1 above may be represented by one of Formulas below.

[Formula 2]

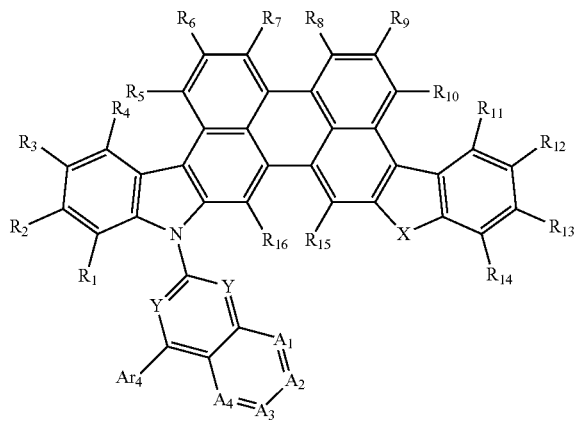

[Formula 3]

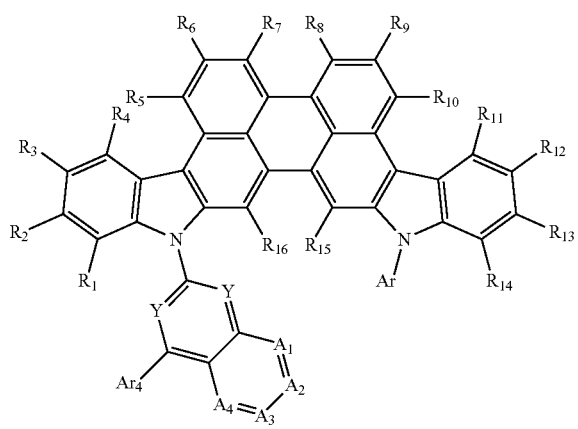

[Formula 4]

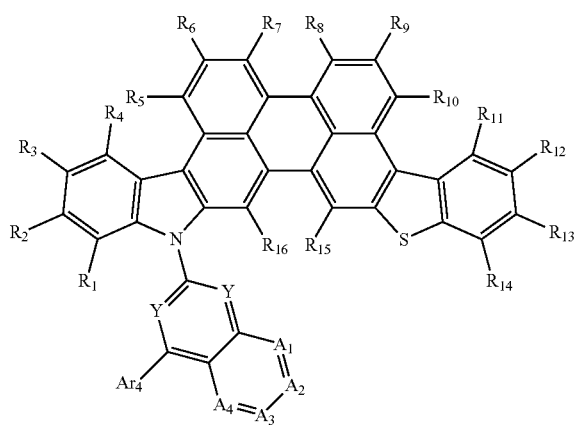

[Formula 5]

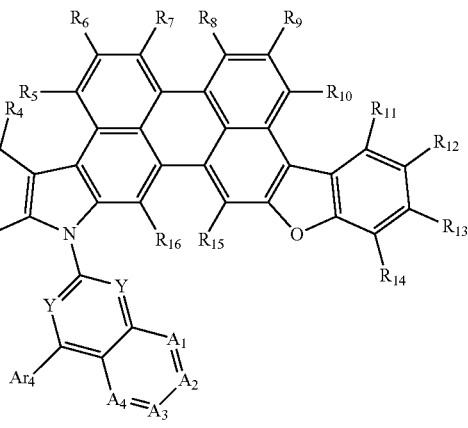

[Formula 6]

In Formula 2 to 6, $R_1$ to $R_{16}$, X, R', R" and Ar can be equally defined as in Formula 1.

Y and $A_1$ to $A_4$ may be the same or different, independently N or $C(R_{17})$.

Here, $R_{17}$ may be hydrogen, deuterium, $C_6$-$C_{60}$ aryl group, a $C_2$-$C_{60}$ heterocyclic group containing at least one heteroatom selected from the group consisting of O, N, S, Si, and P. When Y and $A_1$ to $A_4$ are $CR_{17}$, $R_{17}$ can be different.

In Formula 2 to 6 above, $A_{r11}$ may be selected from the group consisting of a $C_6$-$C_{60}$ aryl group, a $C_2$-$C_{60}$ heterocyclic group containing at least one heteroatom selected from the group consisting of O, N, S, Si, and P, $C_1$-$C_{50}$ alkyl group, $C_2$-$C_{20}$ alkenyl group, $C_1$-$C_{30}$ alkoxyl group and fluorenyl group, and those can be more substituted as substituents defined Formula 1 above such as the aryl group, hetero cyclic group, alkyl group, alkenyl group, alkoxyl group, and fluorenyl group.

Herein, in case of an aryl group above, carbon number is $C_6$-$C_{60}$, desirably $C_6$-$C_{30}$, more desirably $C_6$-$C_{20}$ aryl group.

In case of a heterocyclic group above, carbon number is $C_2$-$C_{60}$, desirably $C_2$-$C_{30}$, more desirably $C_2$-$C_{20}$ heterocyclic group.

In case of an arylen group above, carbon number is $C_6$-$C_{60}$, desirably $C_6$-$C_{30}$, more desirably $C_6$-$C_{20}$ arylen group.

In case of an alkyl group above, carbon number is $C_1$-$C_{50}$, desirably $C_1$-$C_{30}$, more desirably $C_1$-$C_{20}$ alkyl group.

Specifically, the compound represented by Formulae 1 above may be represented by one of compounds below.

1-1
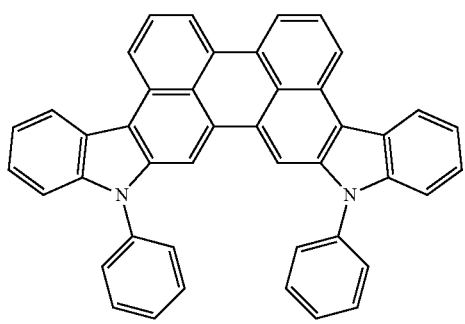
1-2
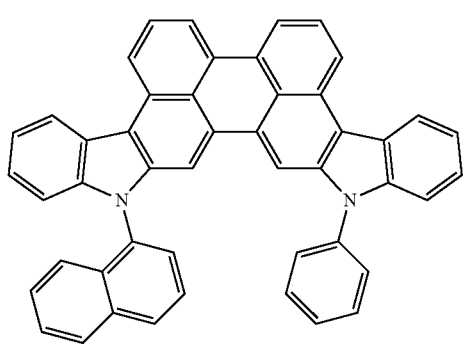
1-3
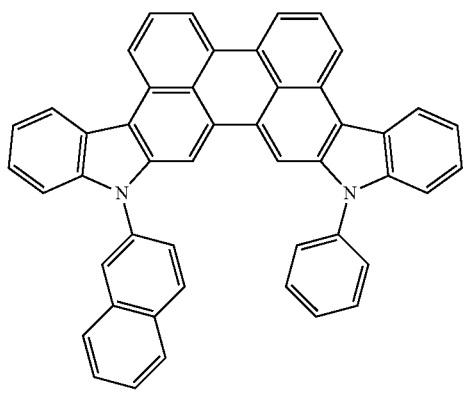
1-4
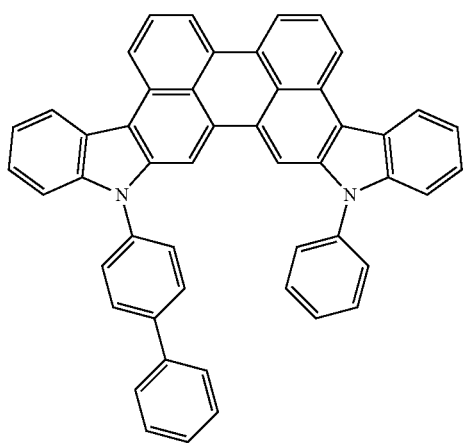
1-5
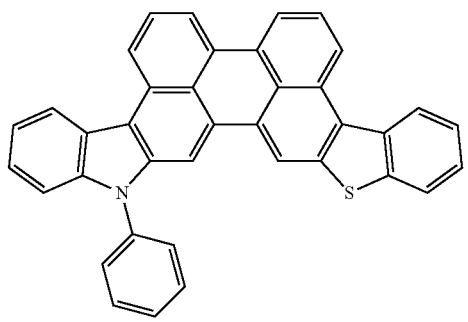
1-6
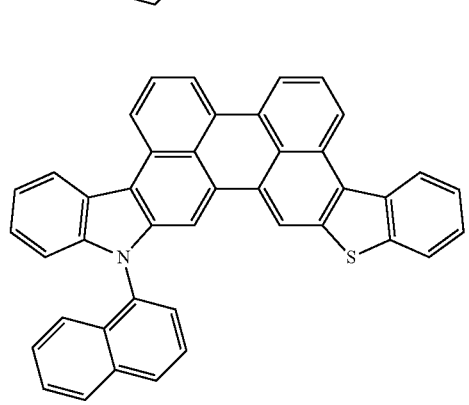
1-7
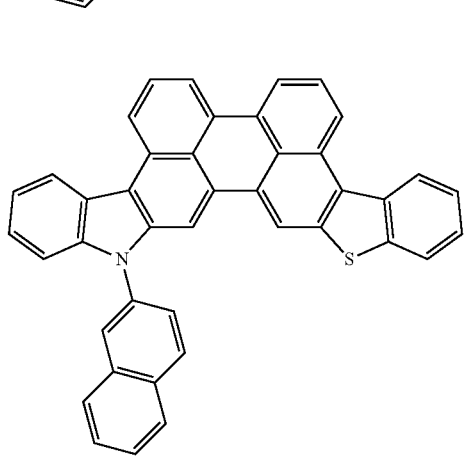
1-8
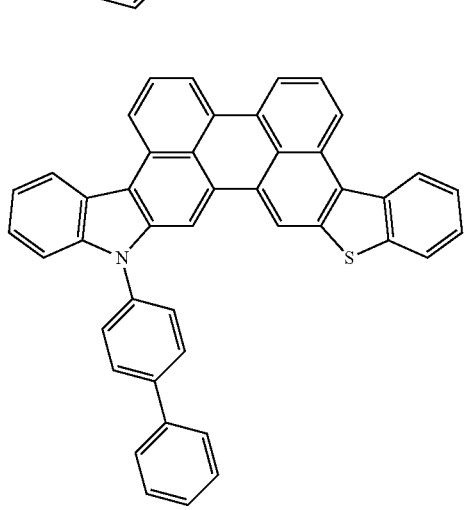

-continued
1-9
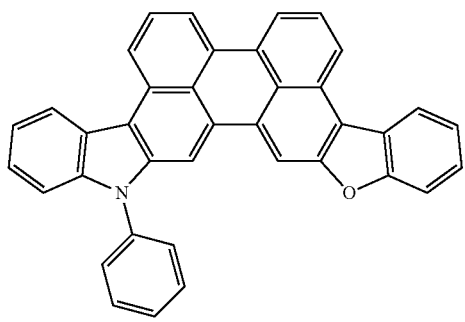
I-10
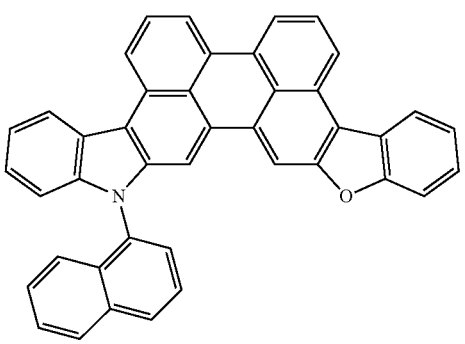
1-11
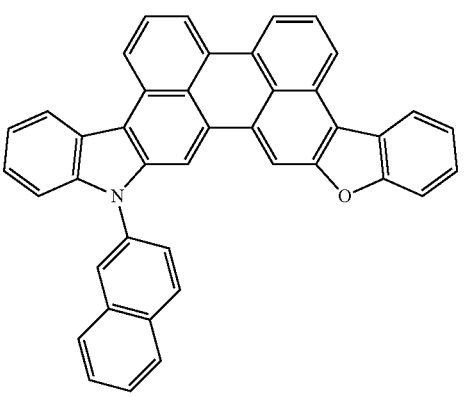
1-12
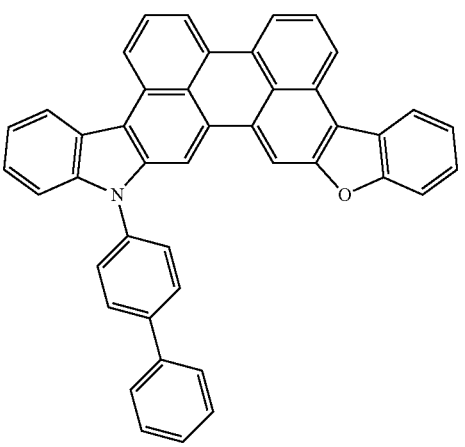
-continued
1-13
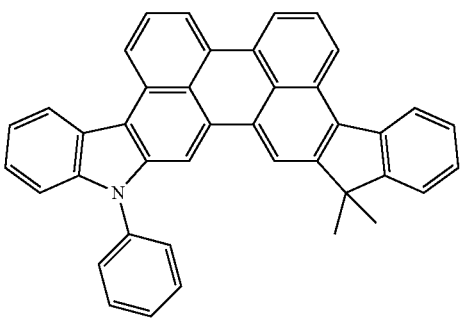
1-14
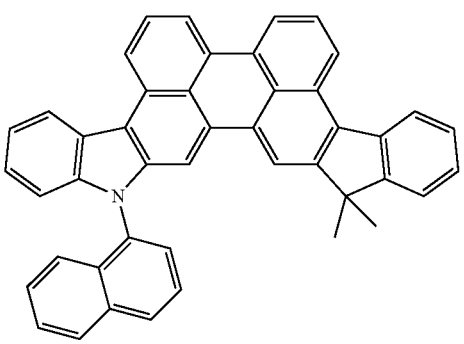
1-15
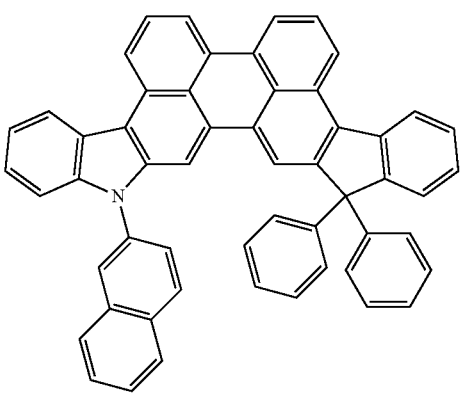
1-16
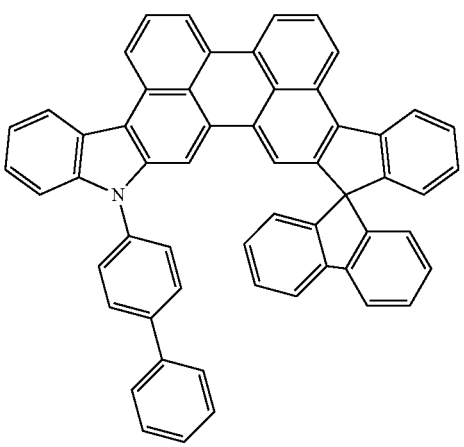

1-17
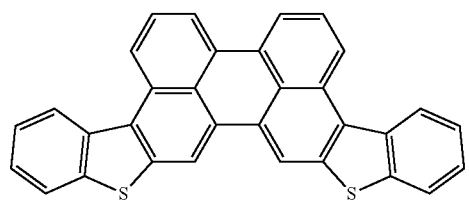
1-18
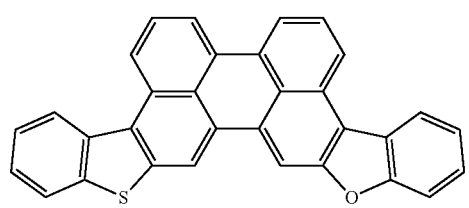
1-19
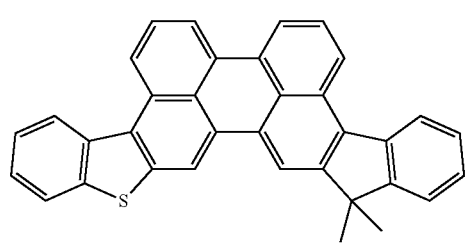
1-20
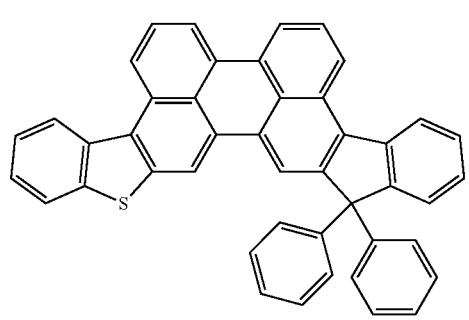
1-21
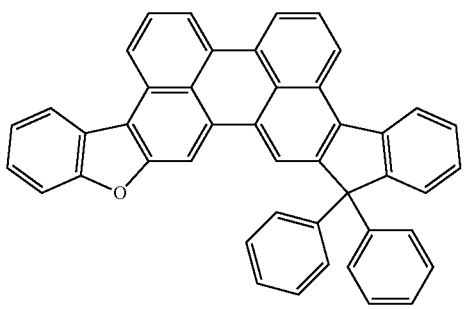
1-22
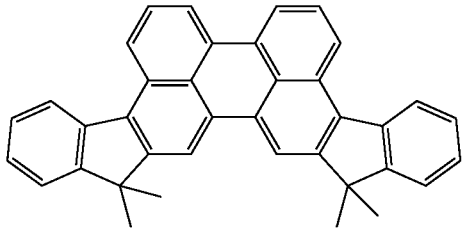
1-23
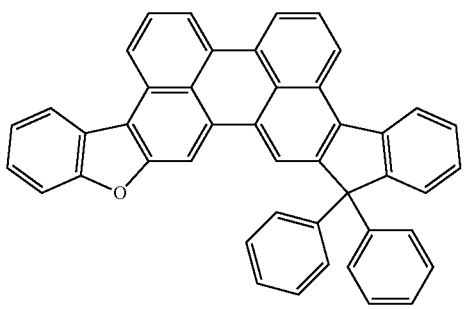
1-24
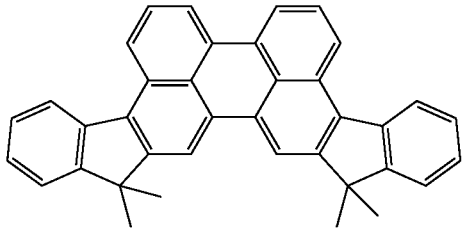
1-25
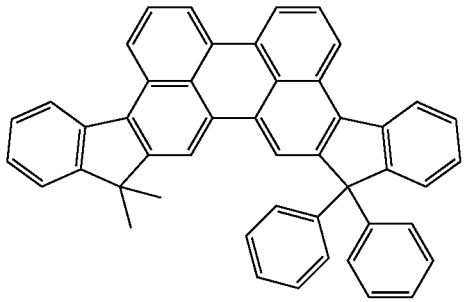
1-26
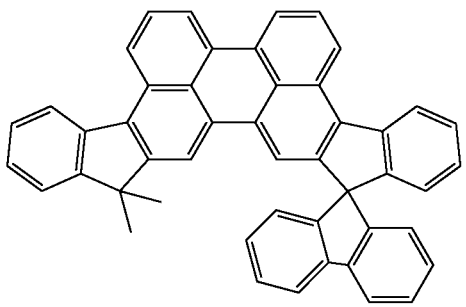
1-27
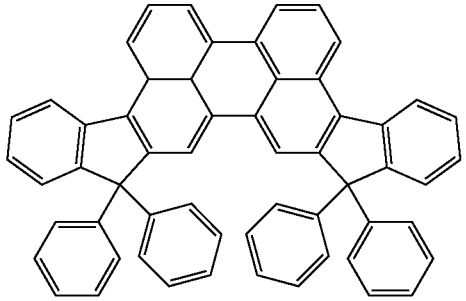

15
-continued
16
-continued
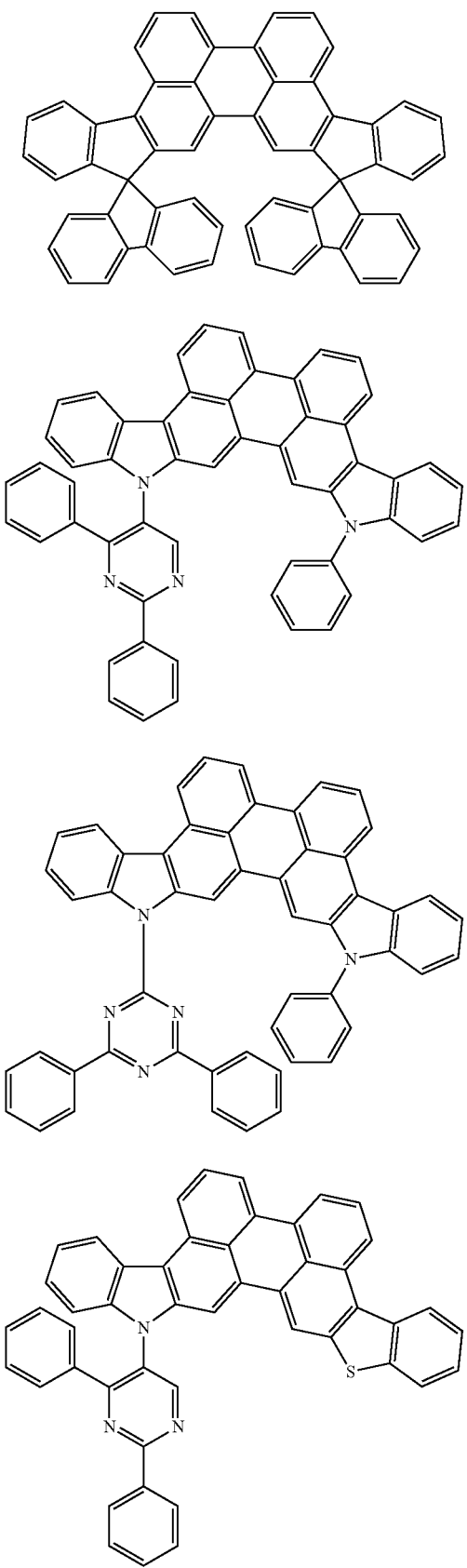
1-28
1-29
1-30
1-31
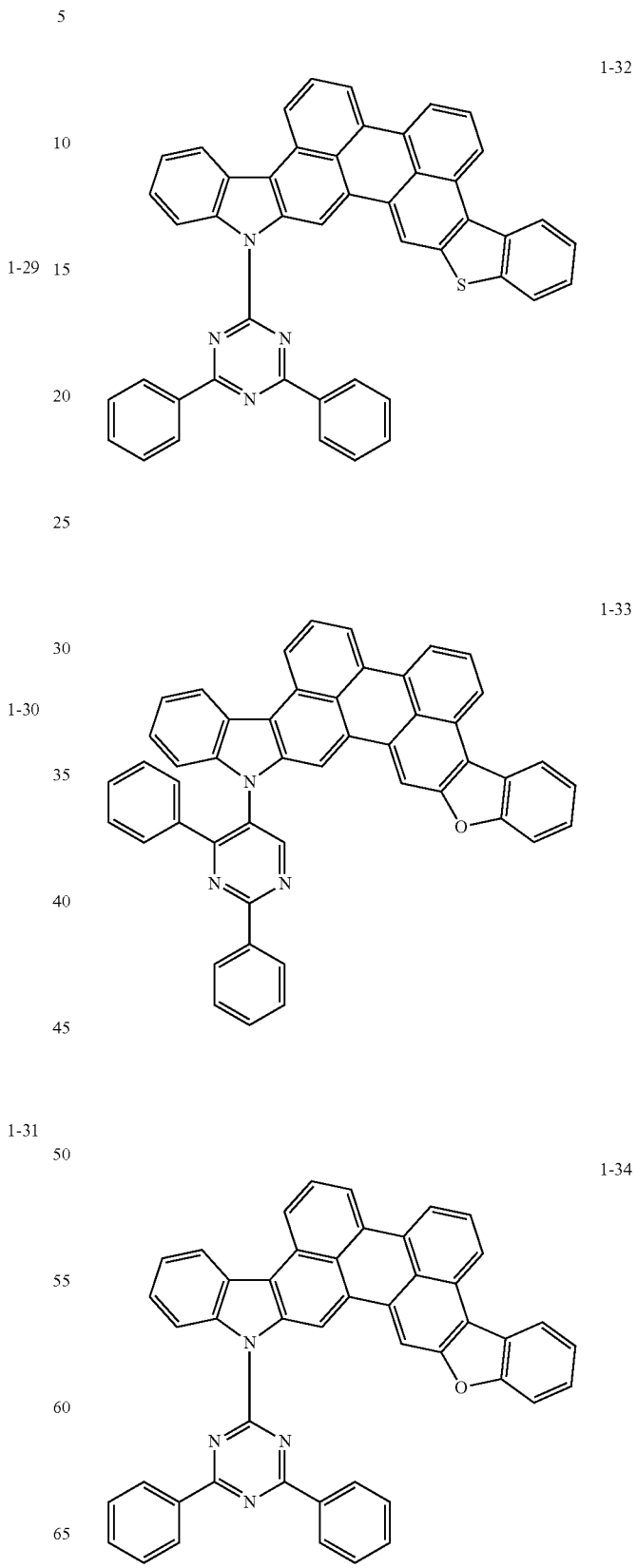
1-32
1-33
1-34

1-35
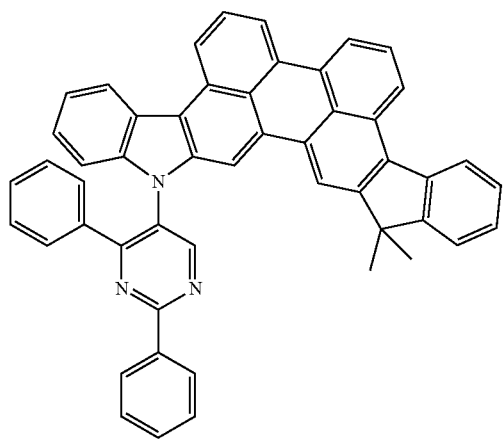
1-36
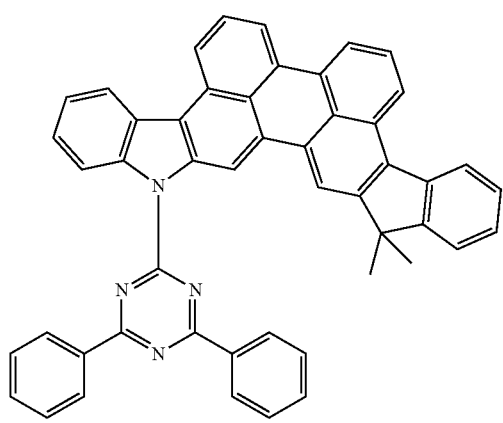
2-1
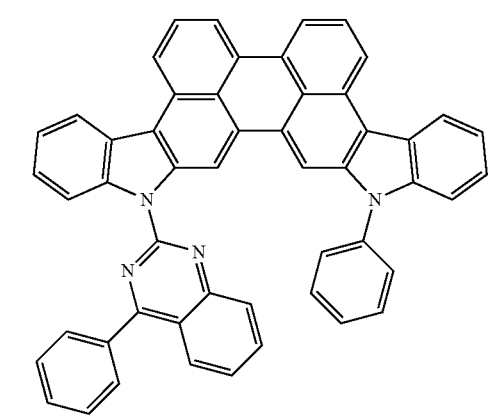
2-2
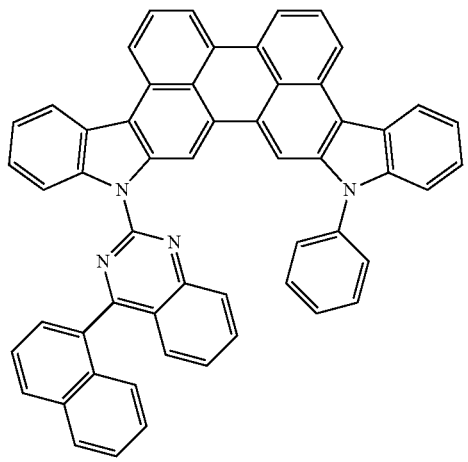
2-3
2-4

US 9,871,207 B2
19
-continued
2-5
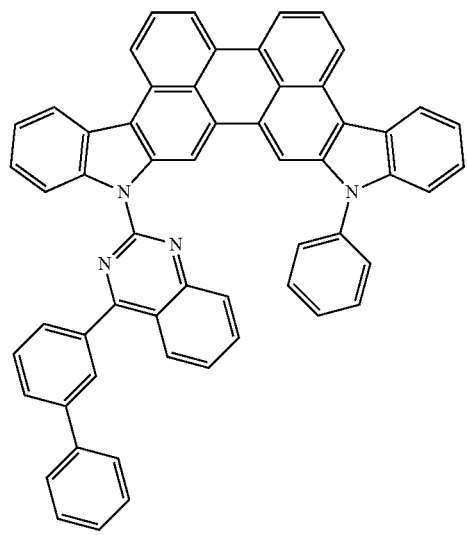
2-6
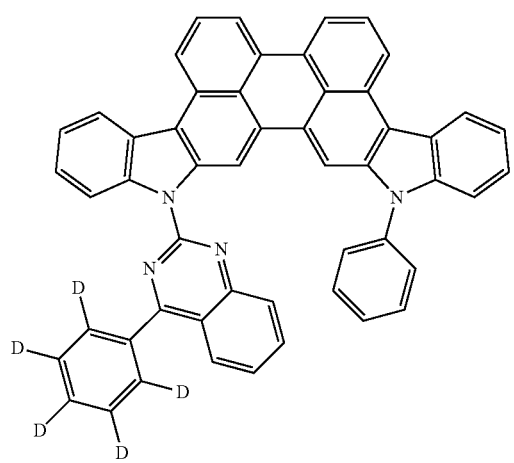
2-7
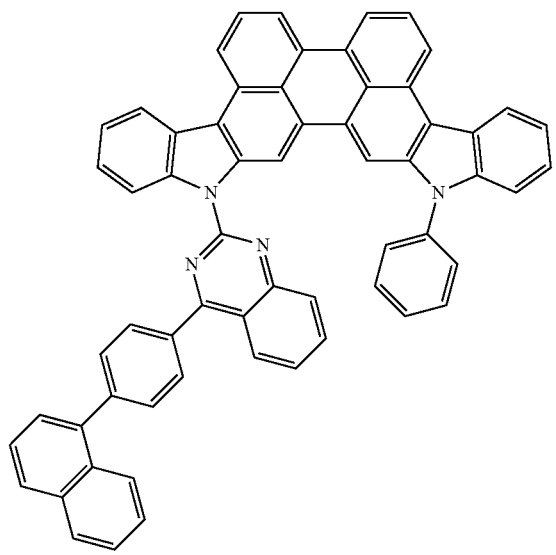
20
-continued
2-8
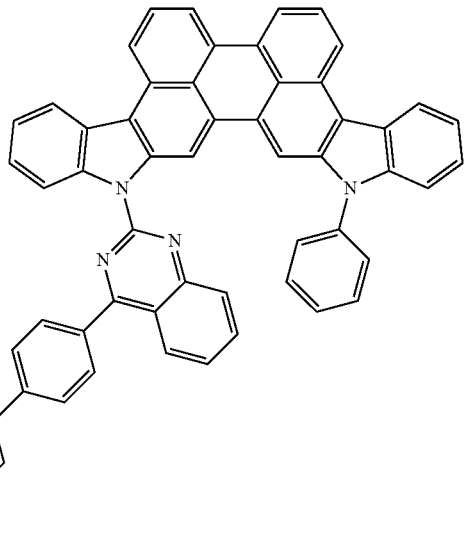
2-9
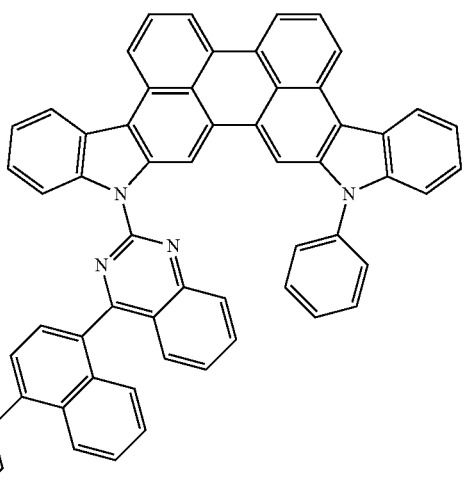
2-10
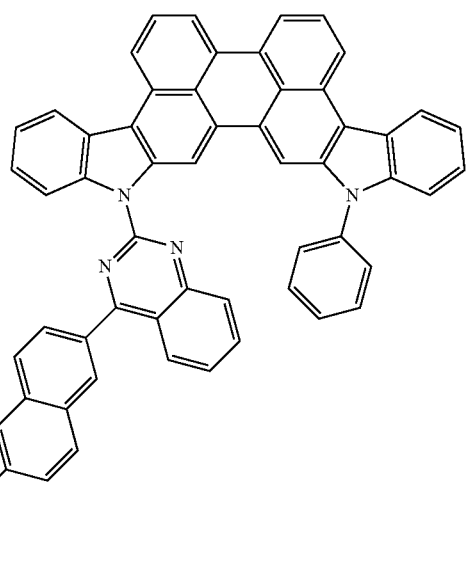

2-11
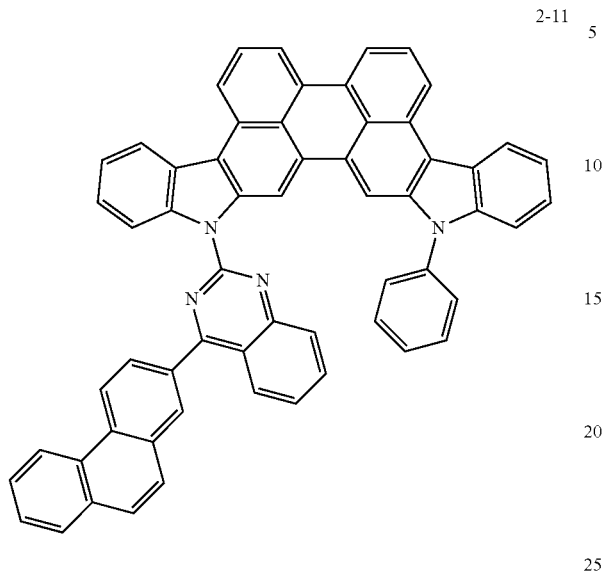
2-14
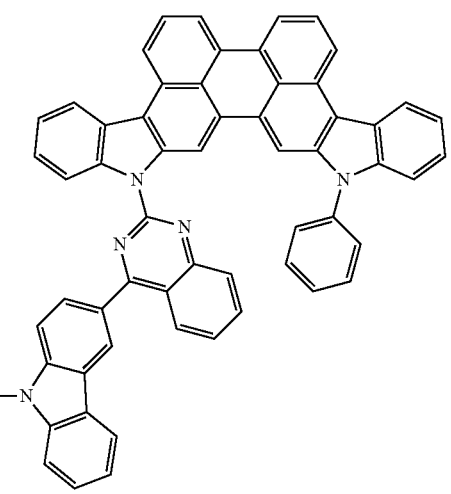
2-12
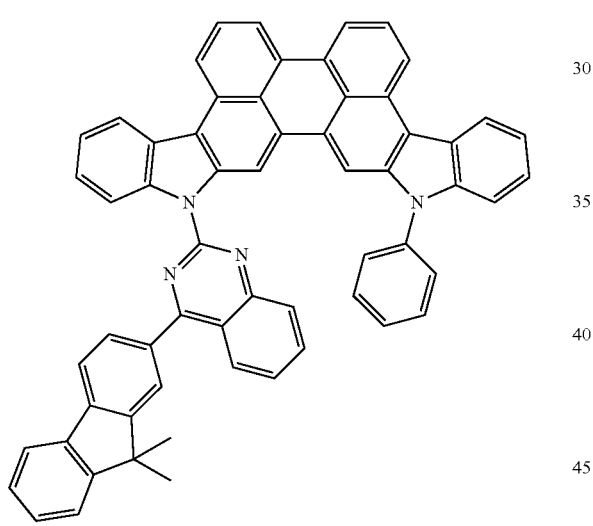
2-15
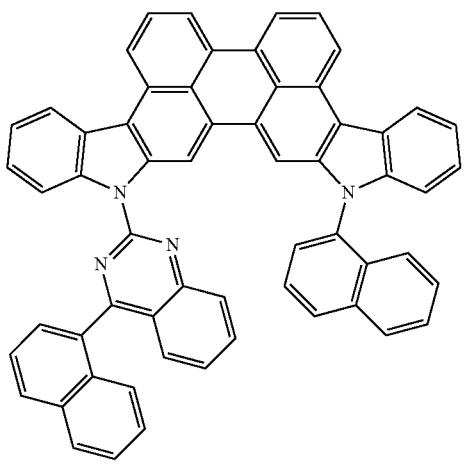
2-13
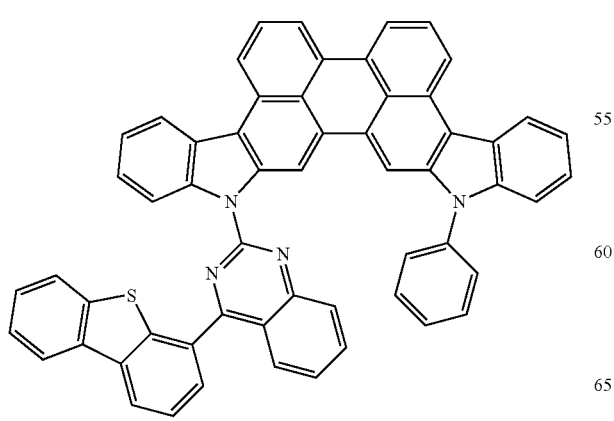
2-16
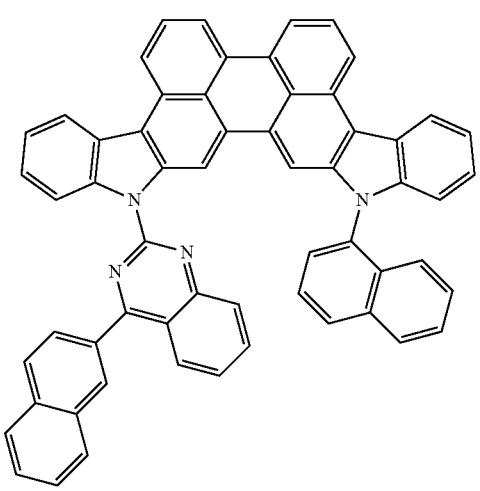

2-17
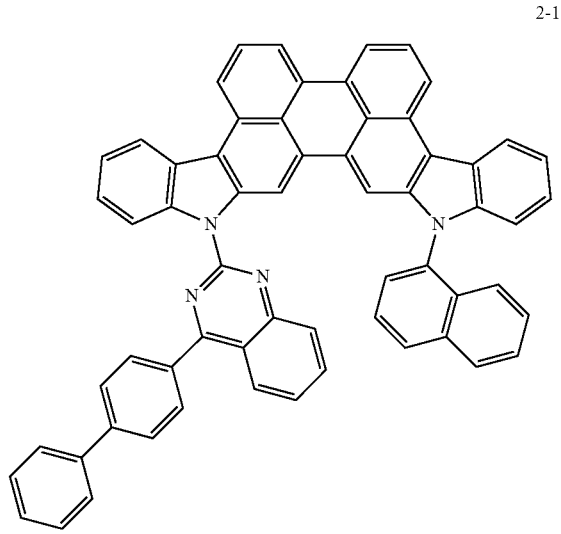
2-18
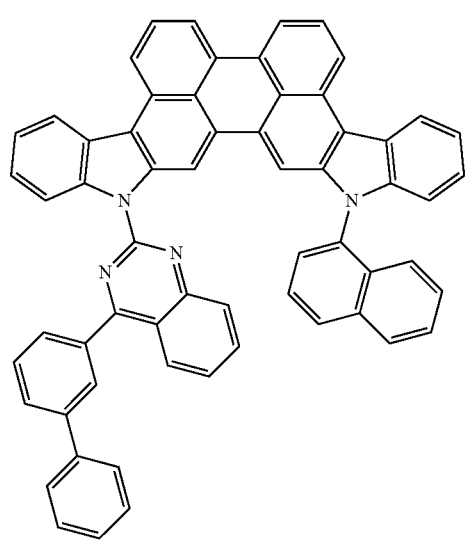
2-19
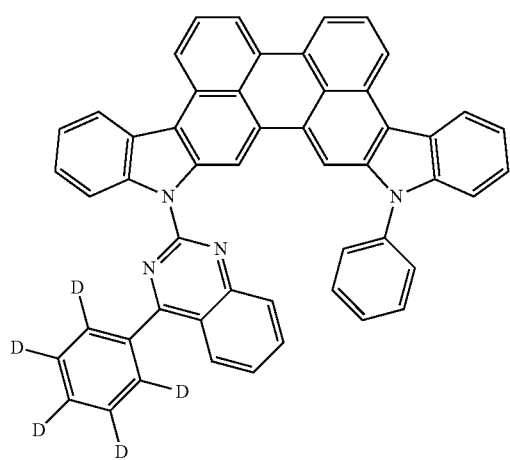
2-20
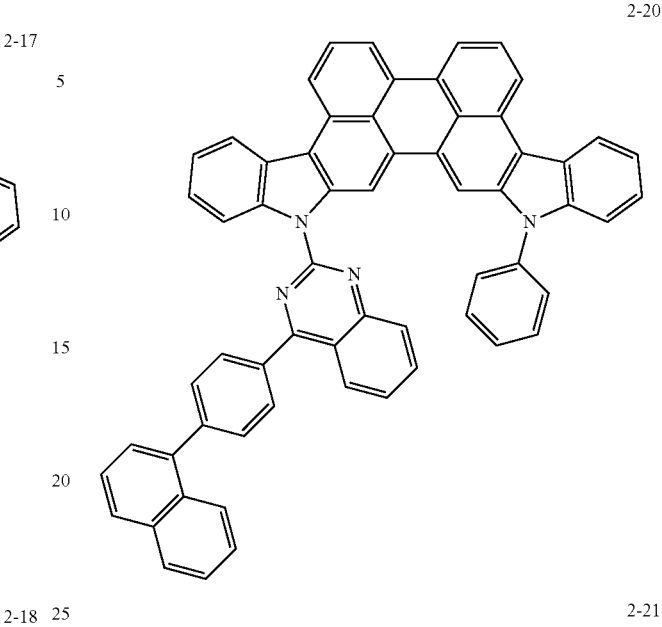
2-21
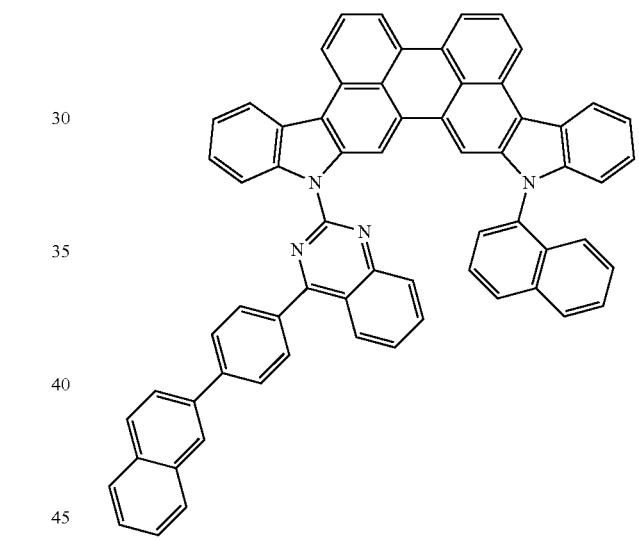
2-22
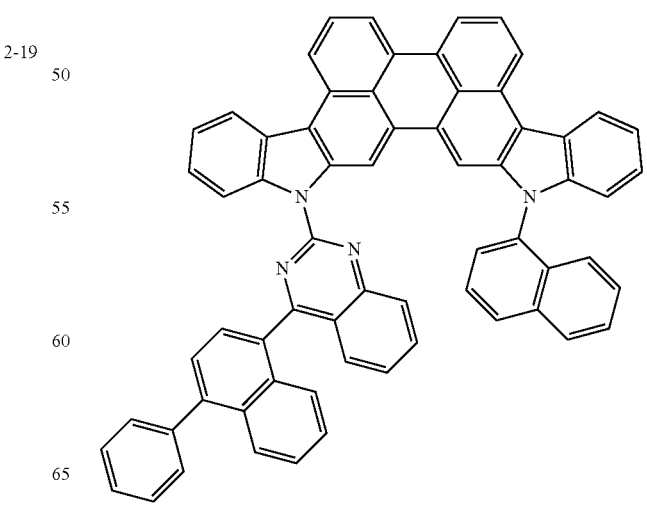

2-23
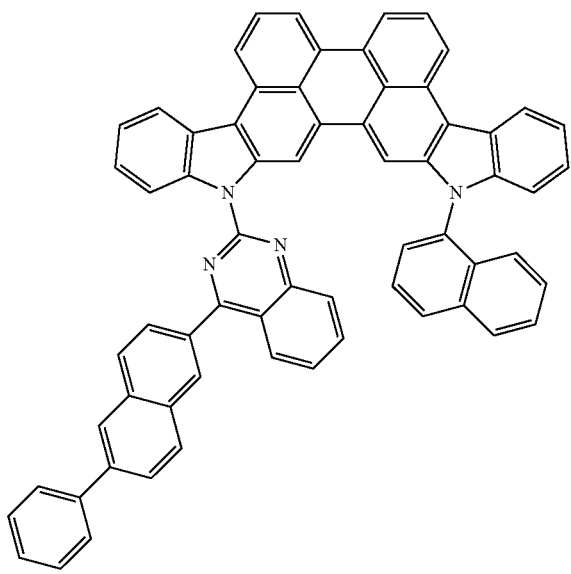
2-24
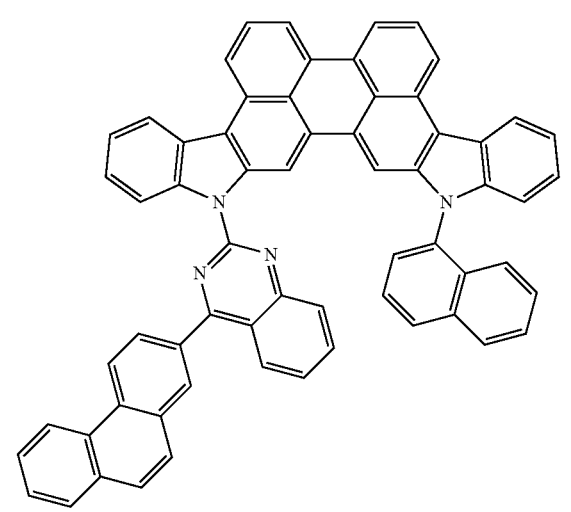
2-25
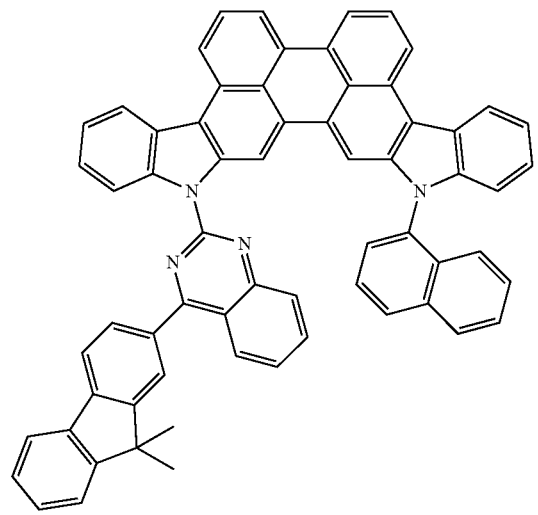
2-26
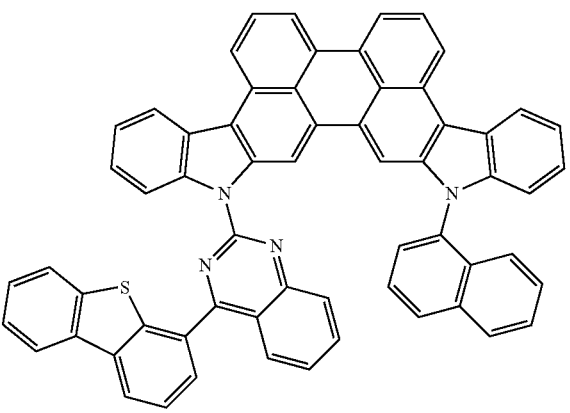
2-27
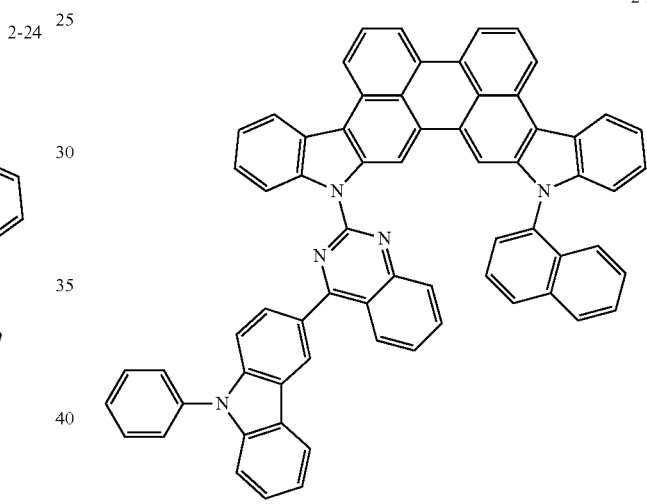
2-28
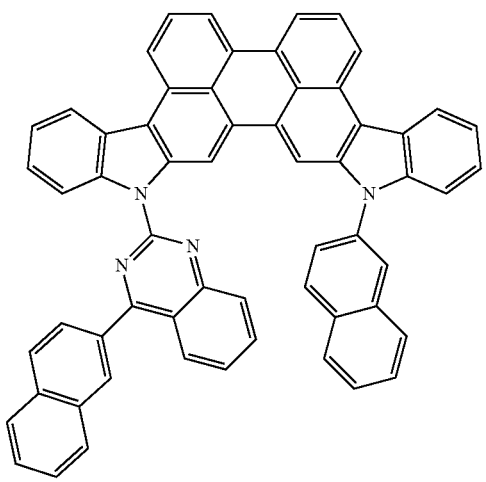

2-29
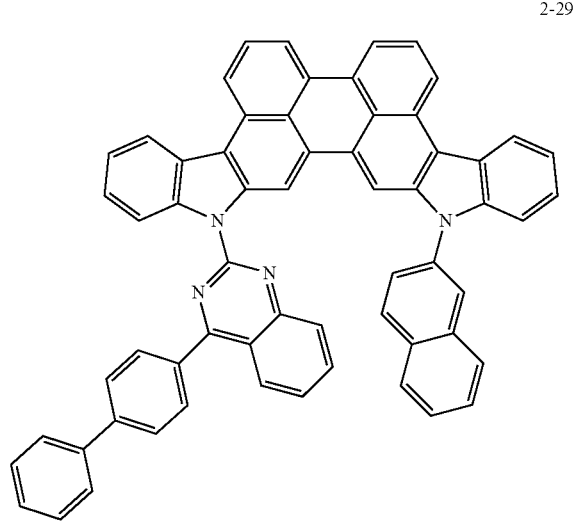
2-30
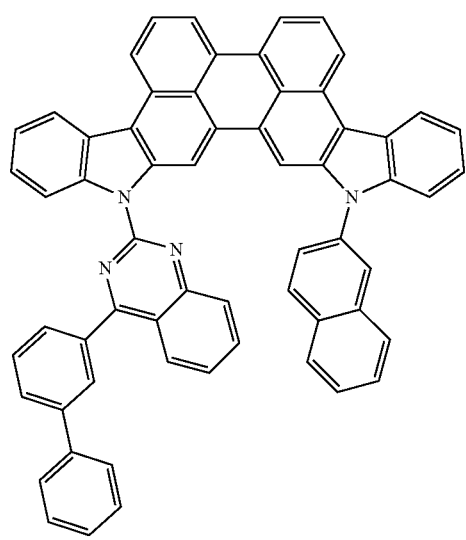
2-31
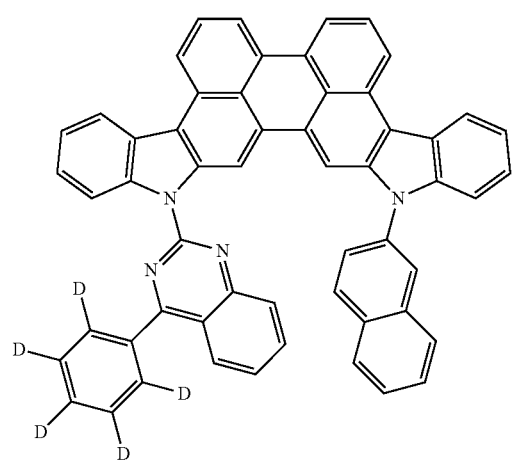
2-32
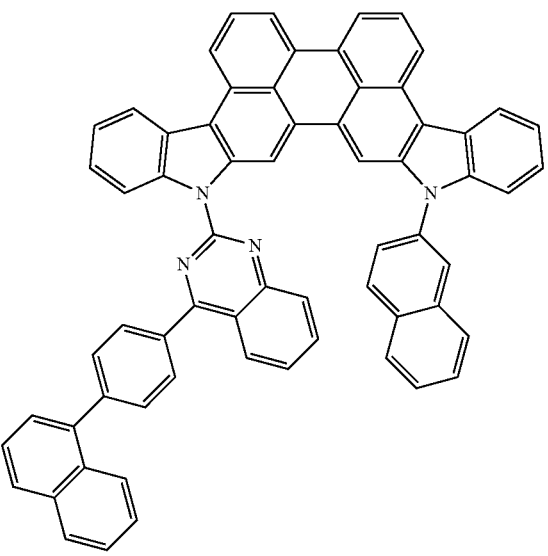
2-33
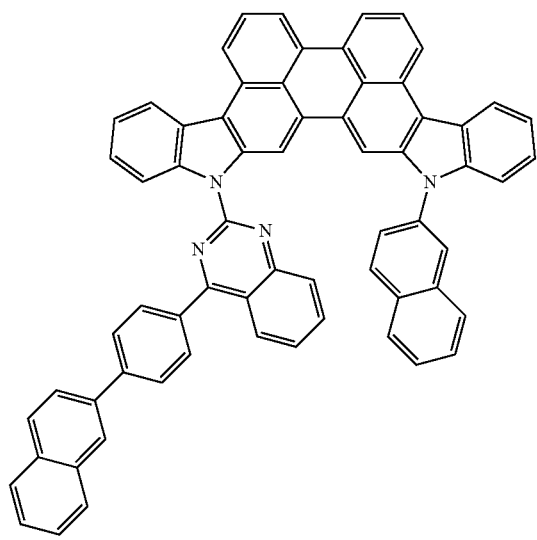
2-34
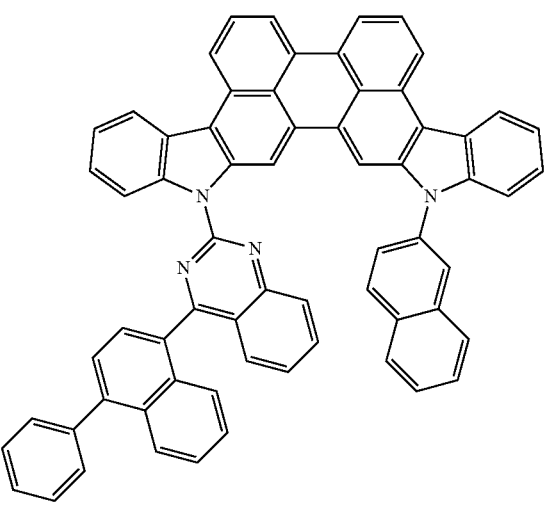

-continued
2-35
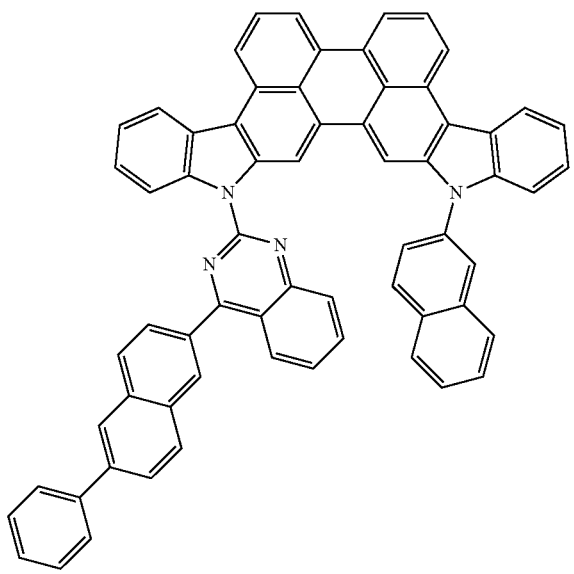
2-36
2-37
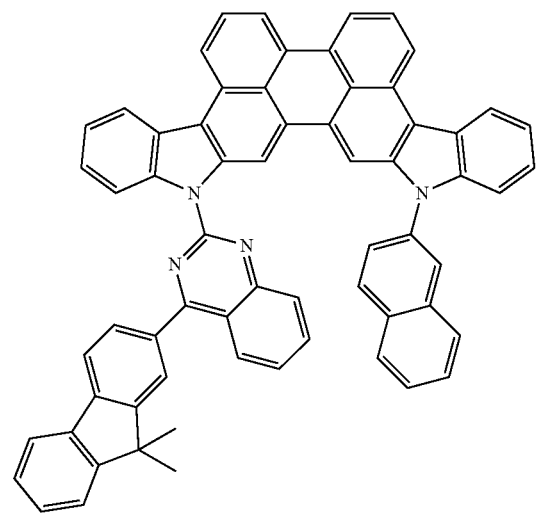
-continued
2-38
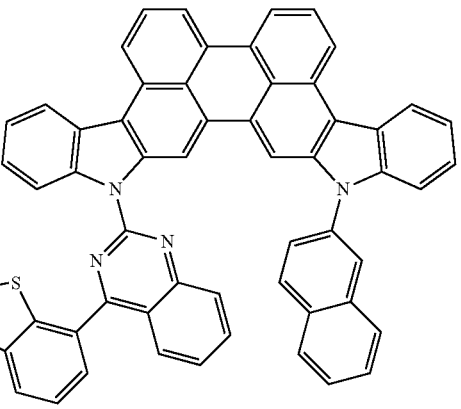
2-39
2-40
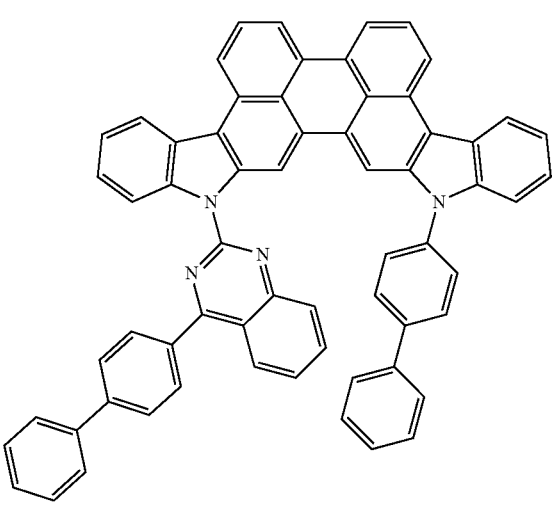

2-41
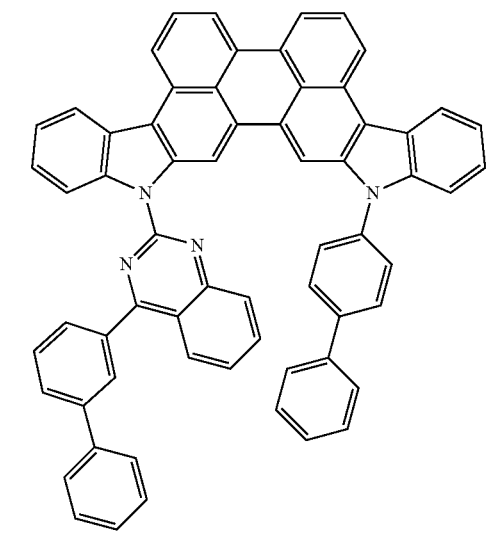
2-42
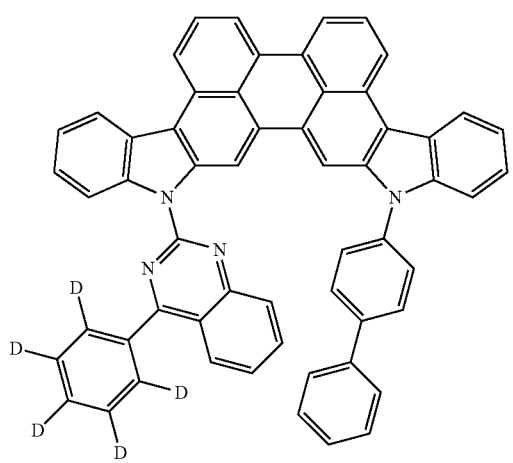
2-43
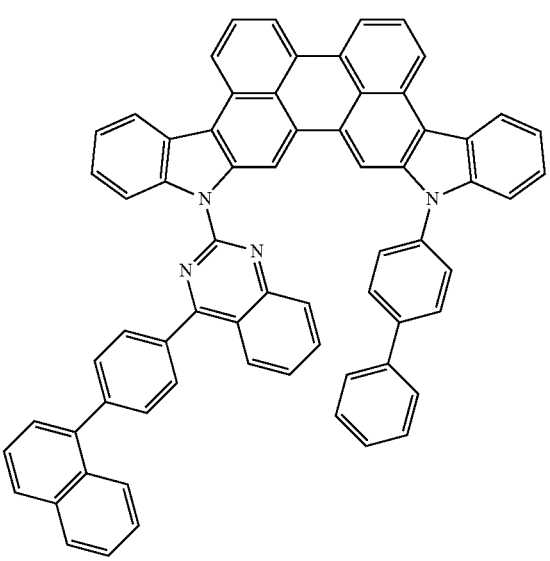
2-44
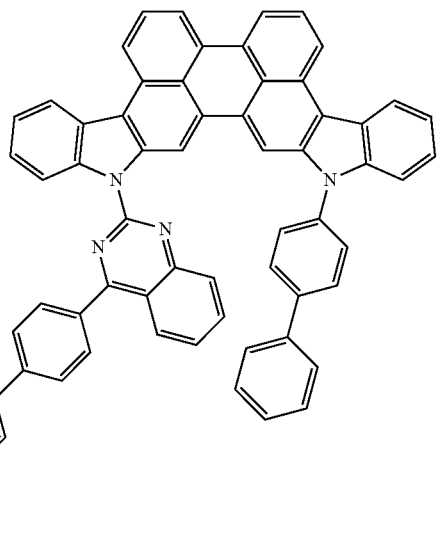
2-45
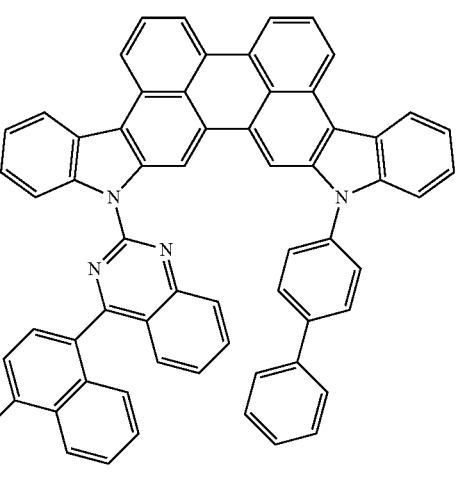
2-46
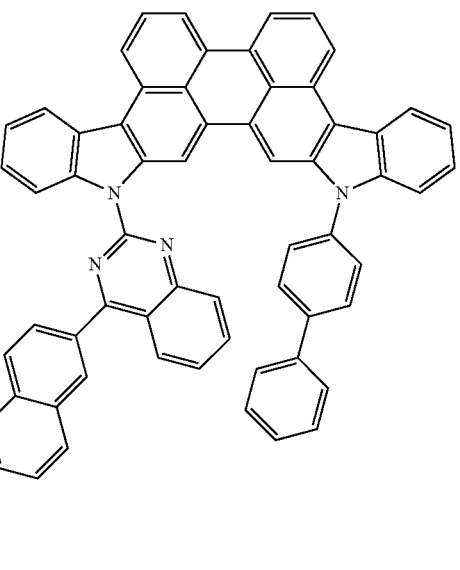

2-47
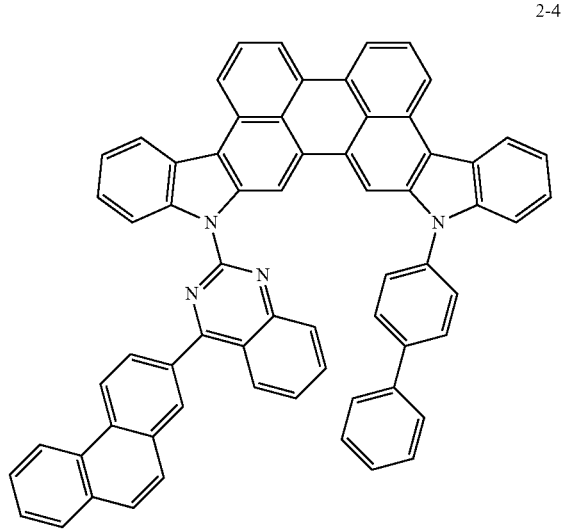
2-48
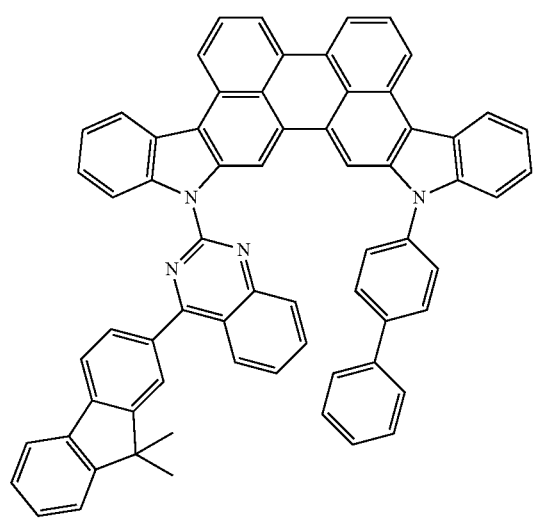
2-49
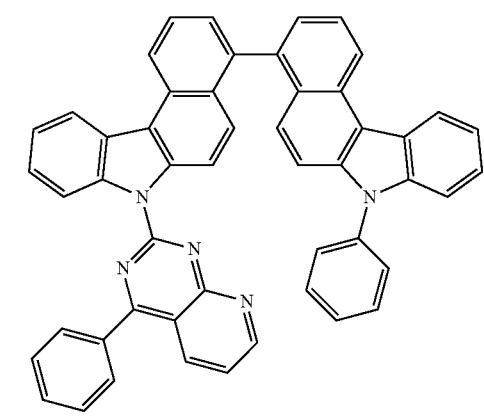
2-50
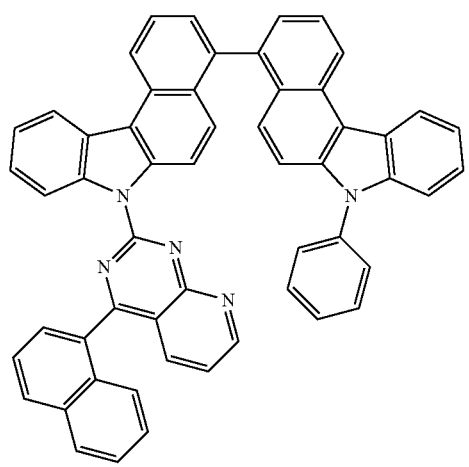
2-51
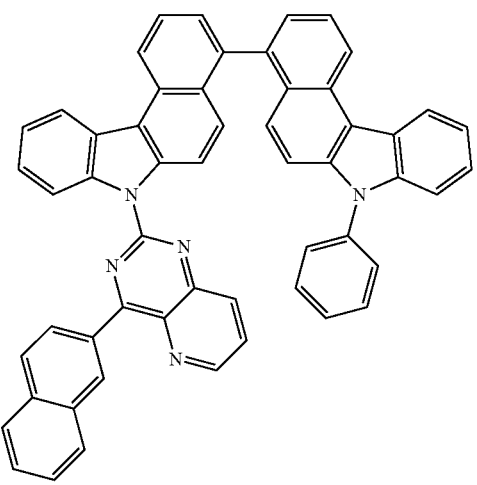
2-52
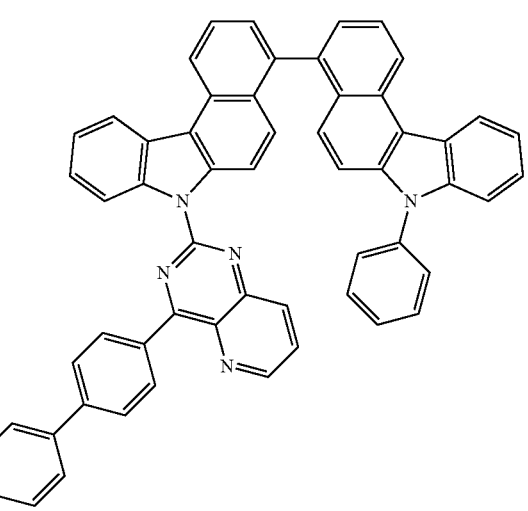

3-1 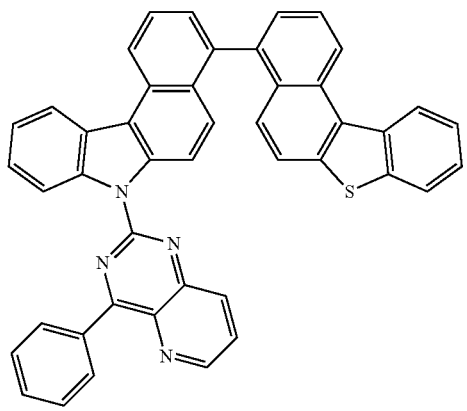
3-2 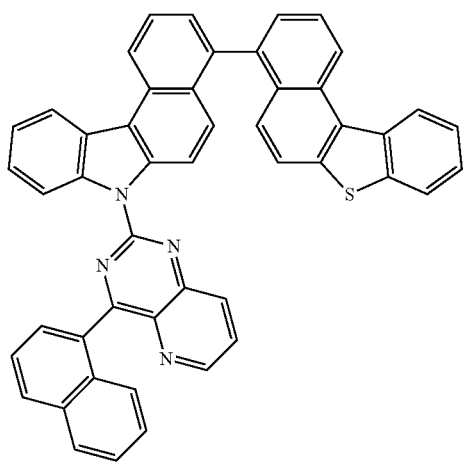
3-3 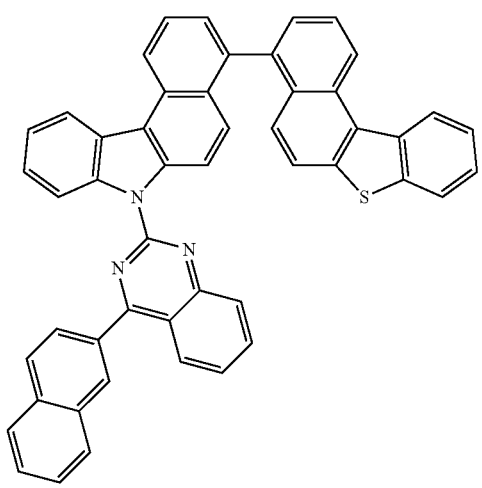
3-4 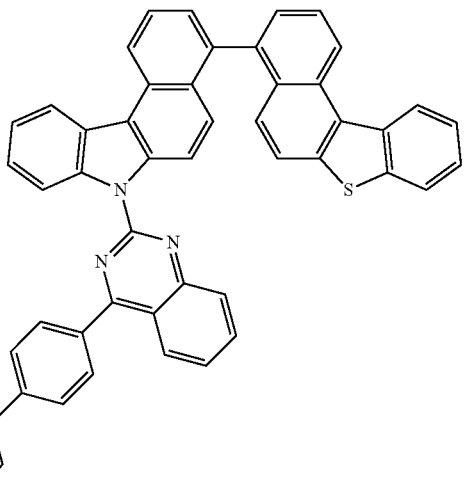
3-5 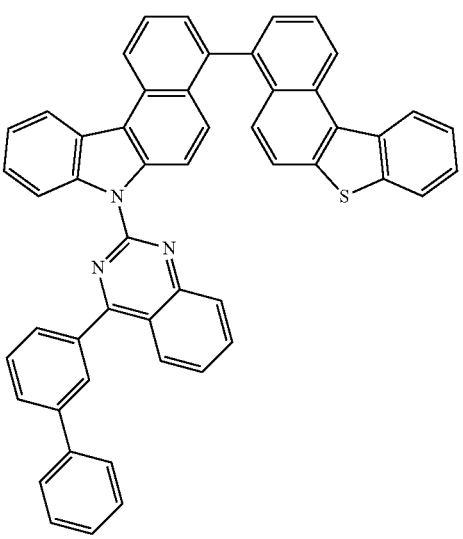
3-6 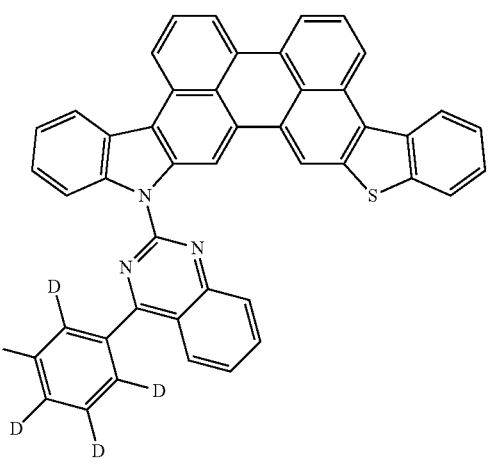

3-7
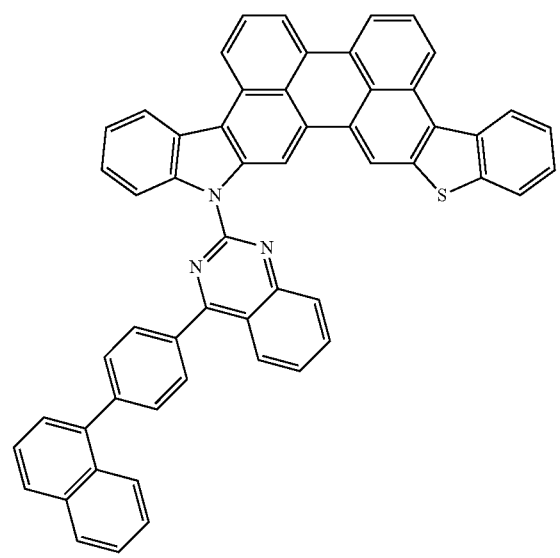
3-8
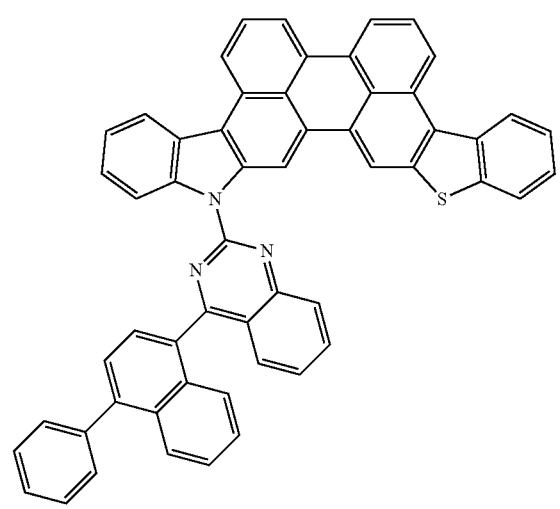
3-9
3-10
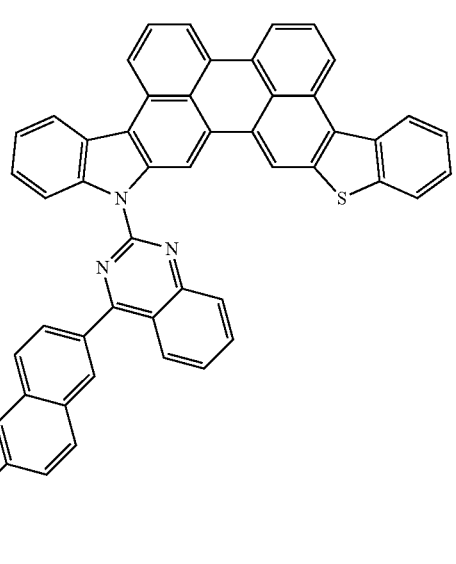
3-11
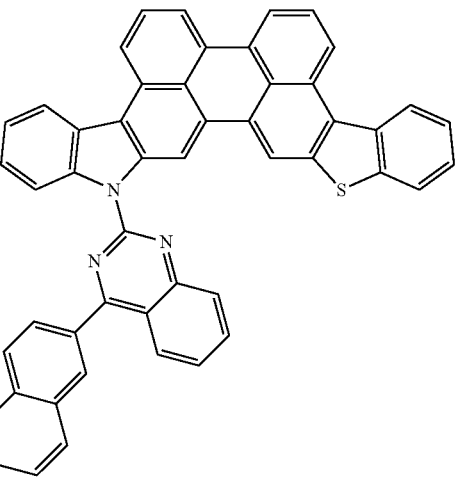
3-12
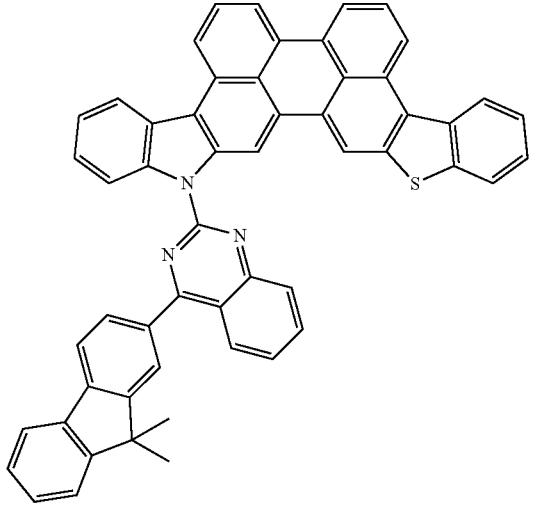

3-13
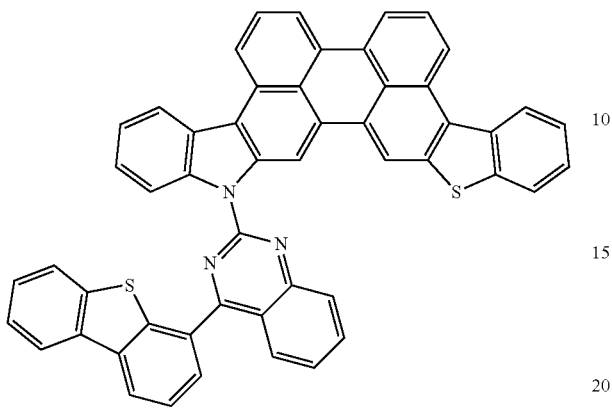
3-14
3-15
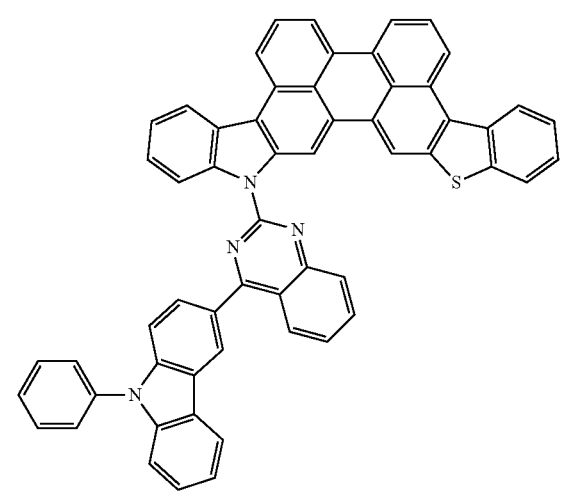
3-16
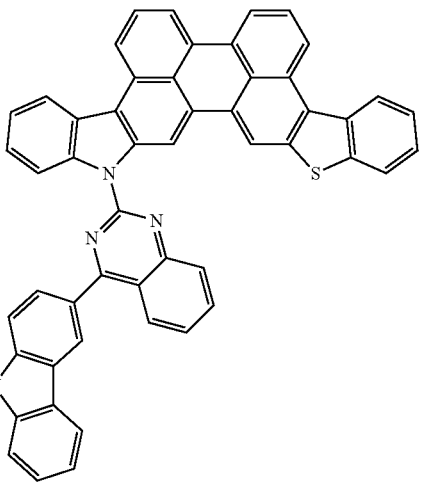
4-1
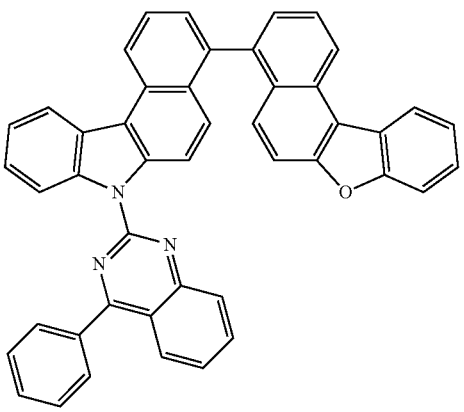
4-2
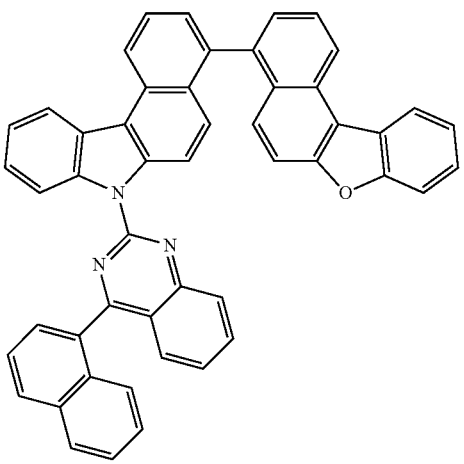

4-3
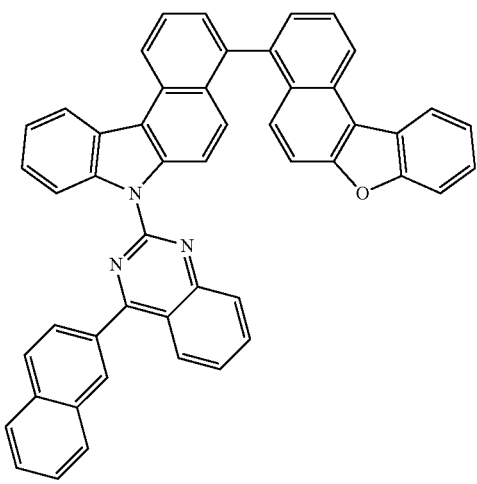
4-4
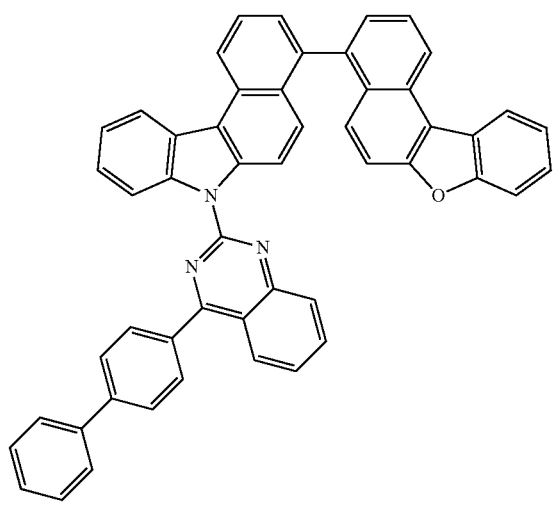
4-5
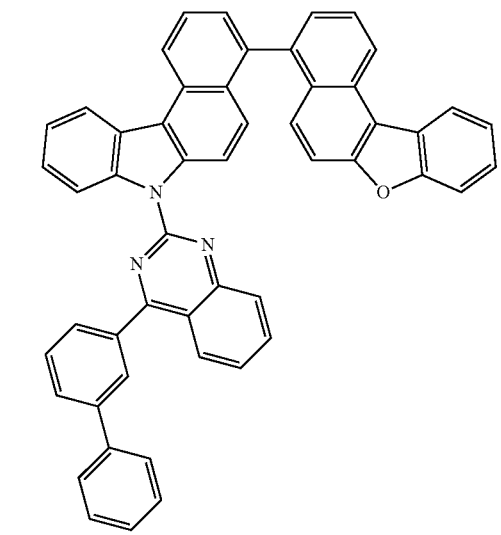
4-6
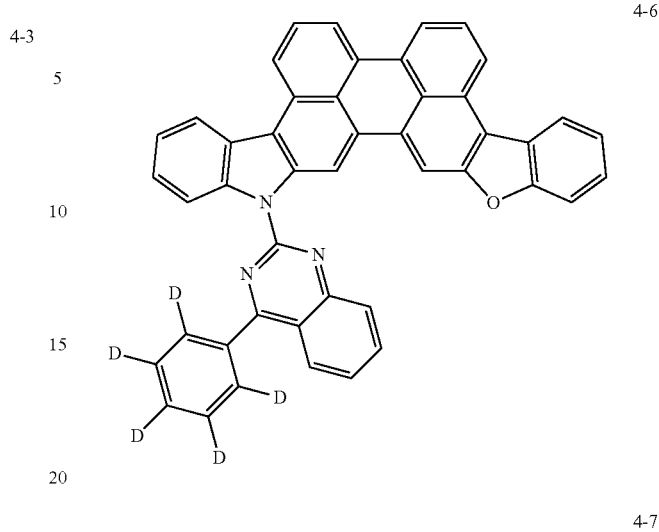
4-7
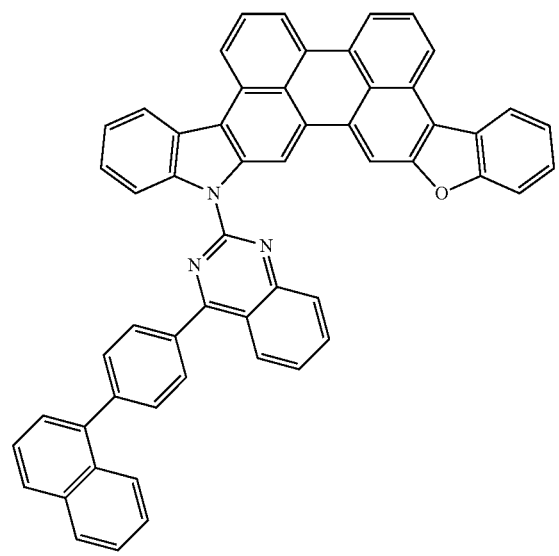
4-8
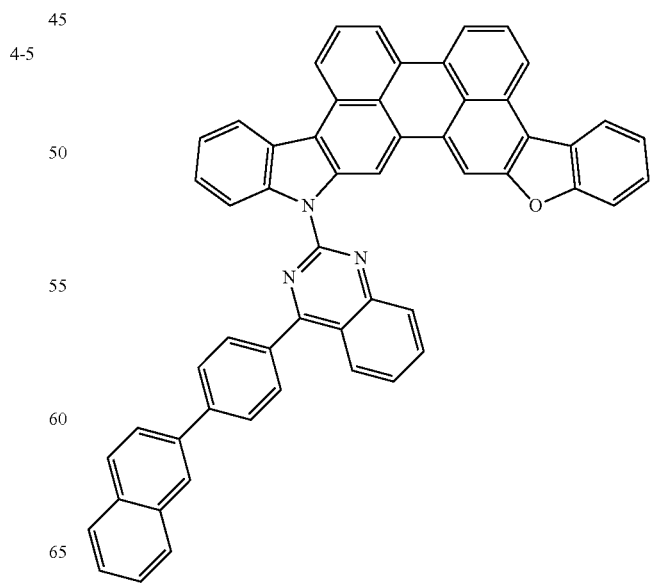

4-9
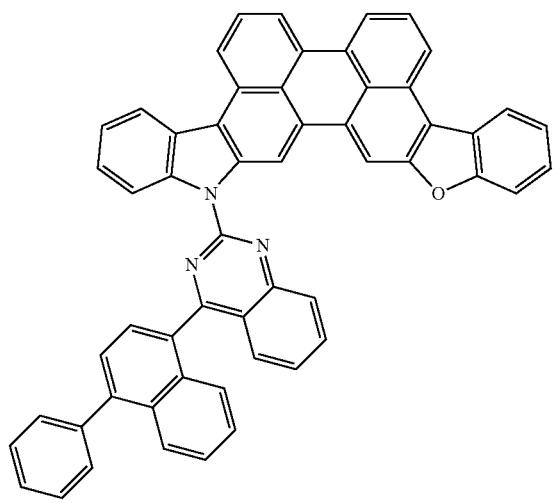
4-10
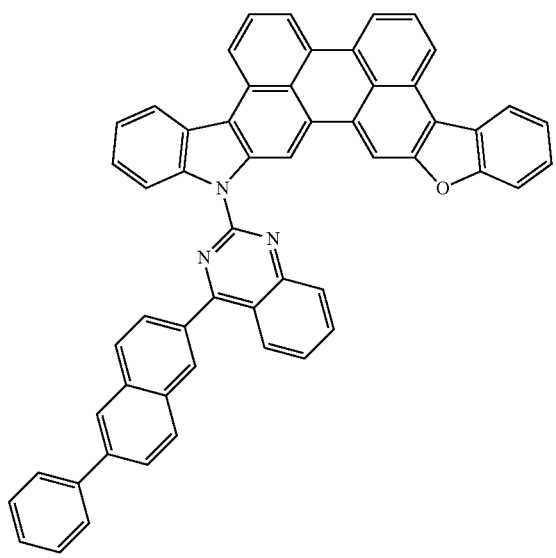
4-11
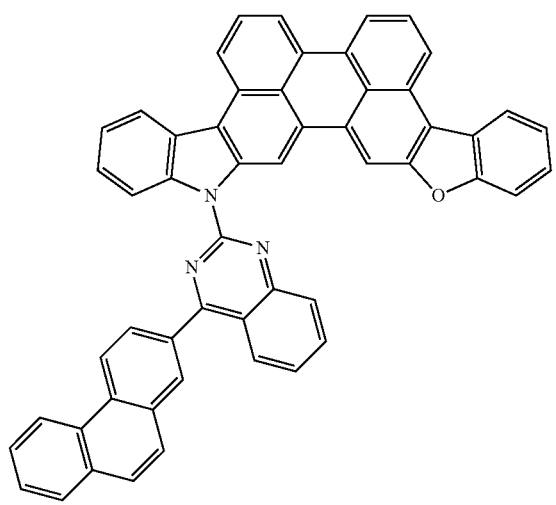
4-12
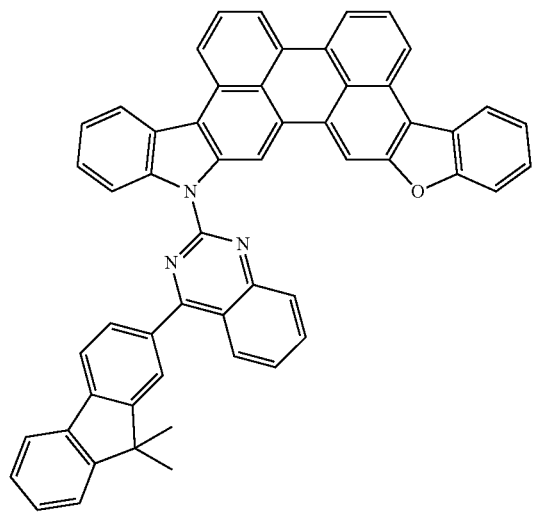
4-13
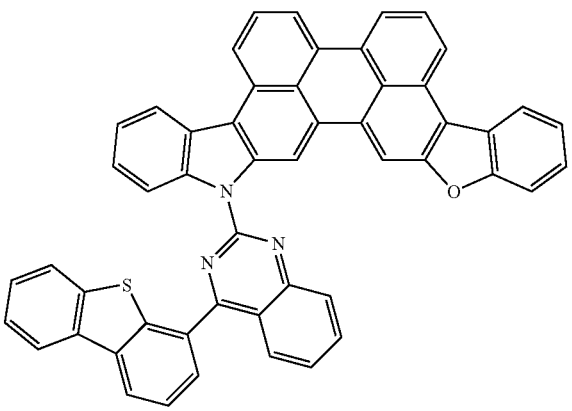
4-14
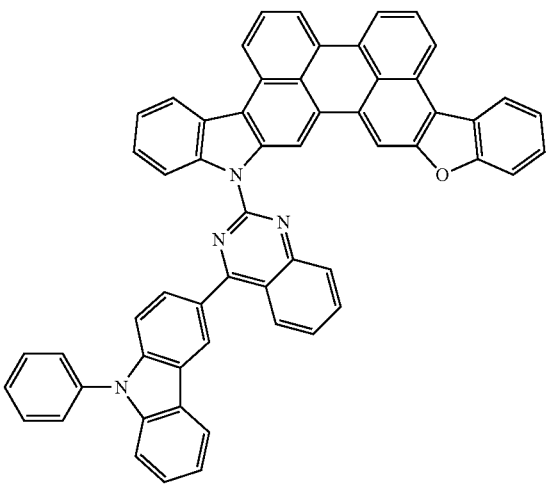

4-15
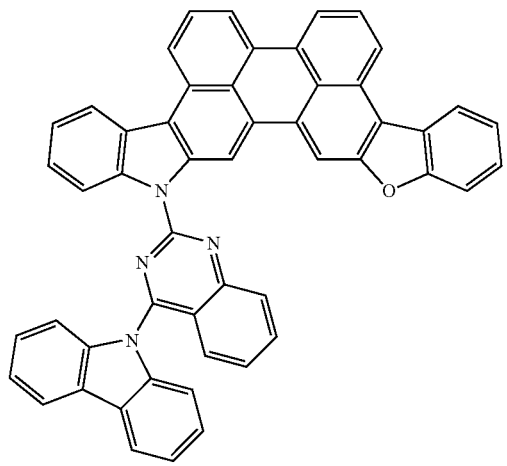
4-16
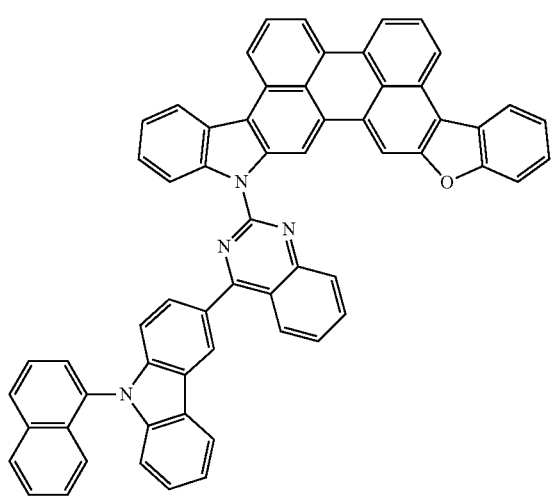
5-1
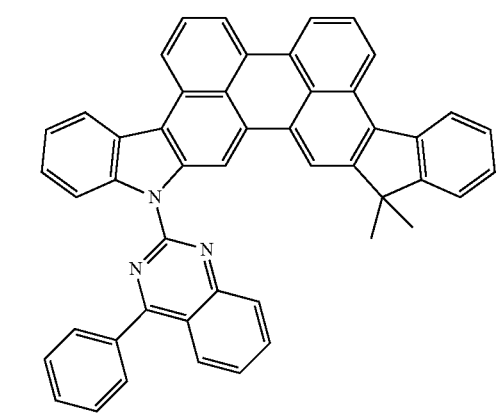
5-2
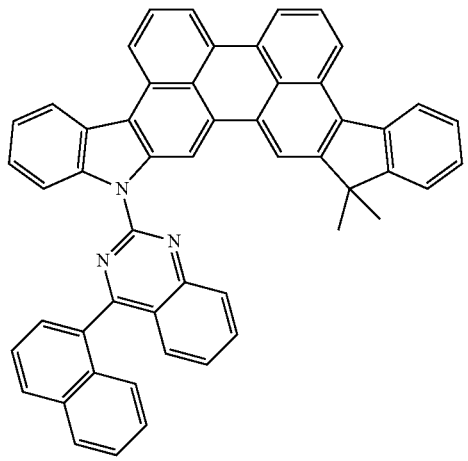
5-3
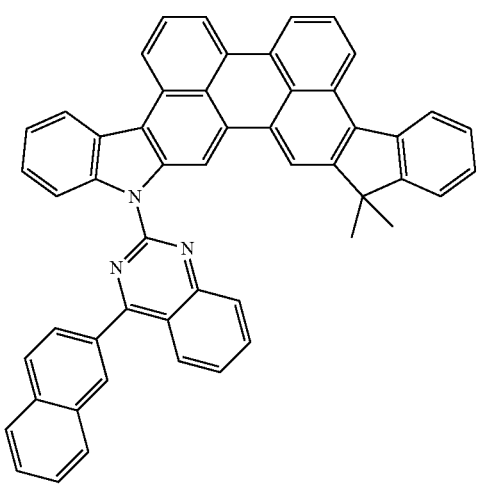
5-4
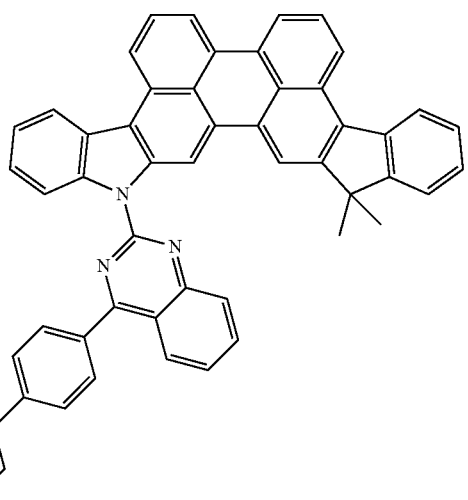

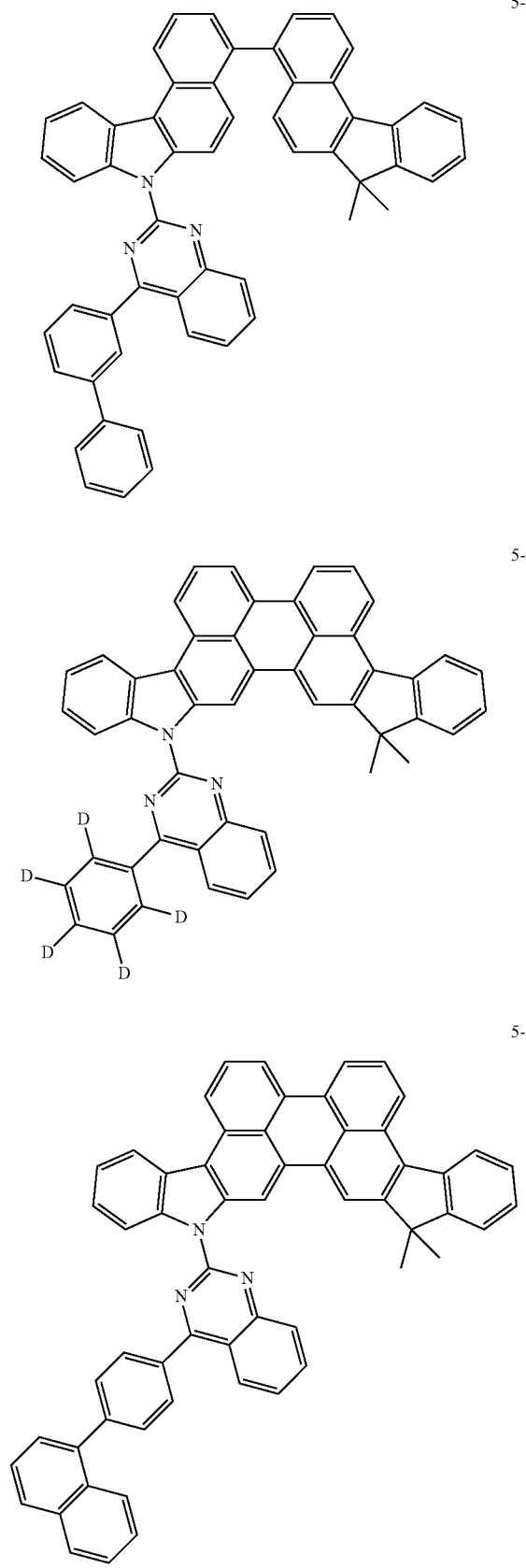
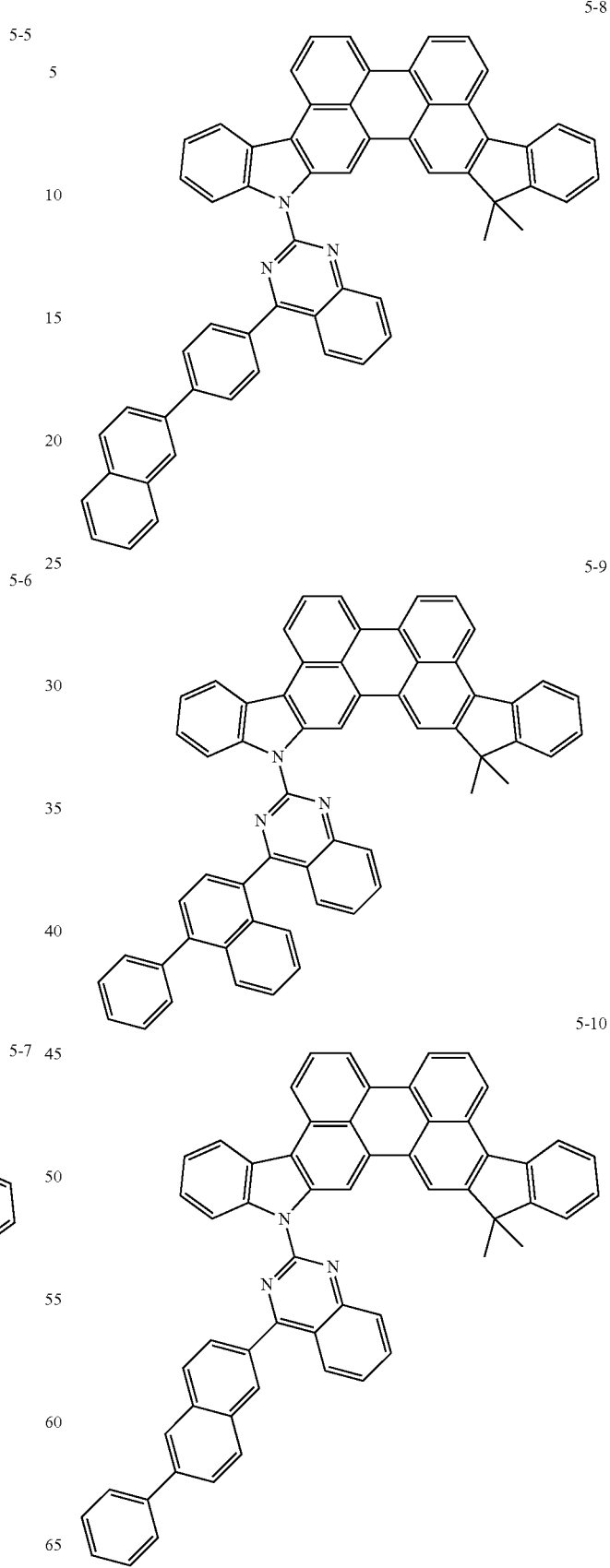

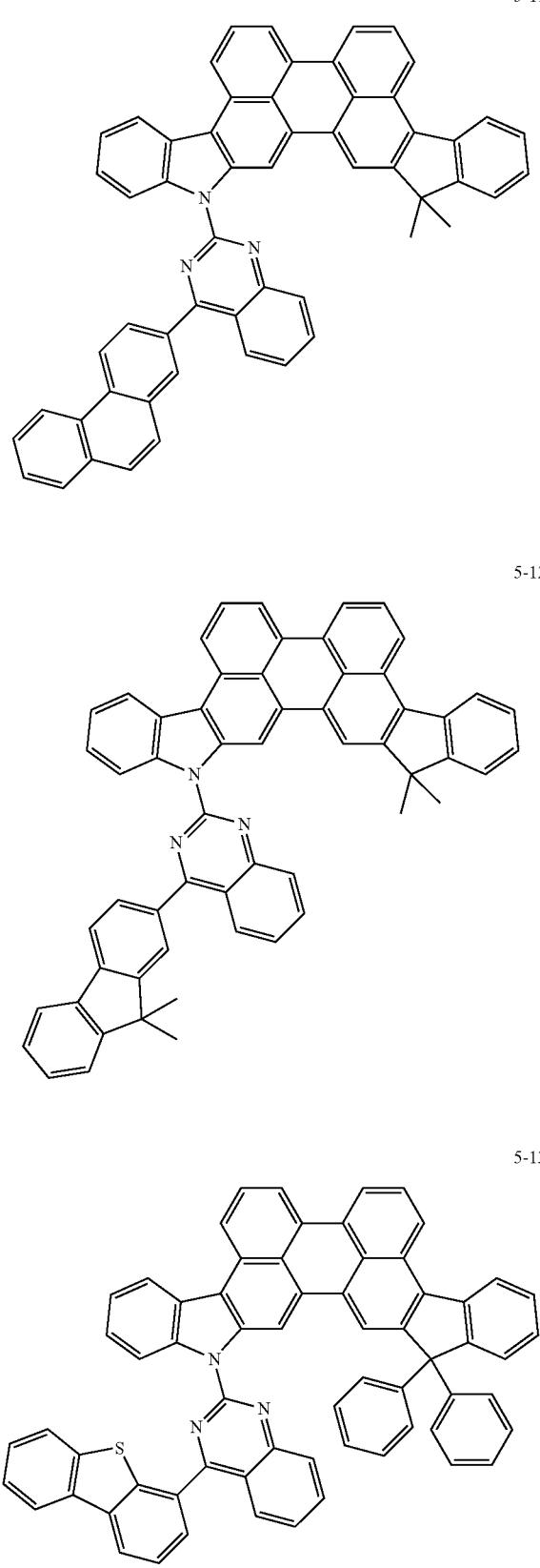
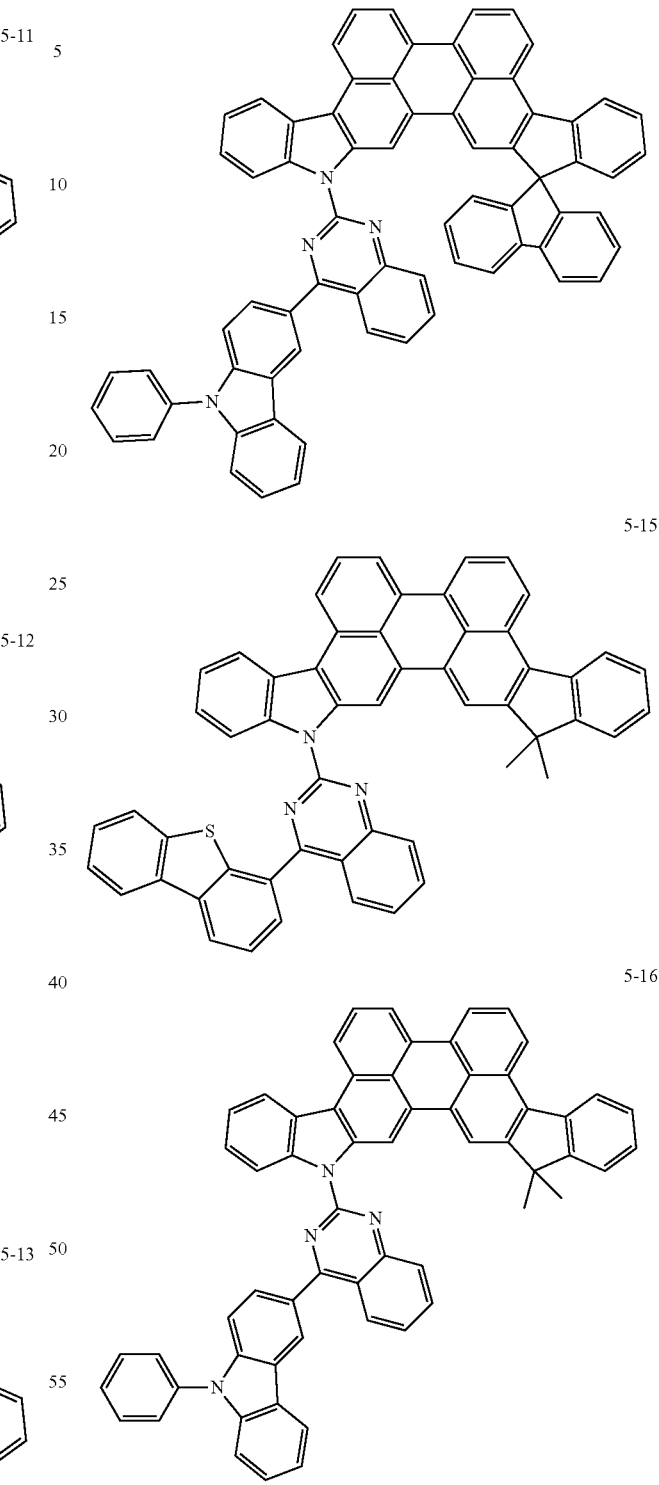
Hereinafter, Synthesis Examples of the compound represented by Formulae according to the present invention and Preparation Examples of an organic electric element will be described in detail by way of example. However, the following examples are only for illustrative purposes and are not intended to limit the scope of the invention.

SYNTHESIS EXAMPLE

Synthesis Example of Product 1

The final product 1 of the present invention, represented by Formula 1, can be synthesized by reaction between Sub 1 and Sub 2 as illustrated in, but not limited to, the following Reaction Scheme 1.

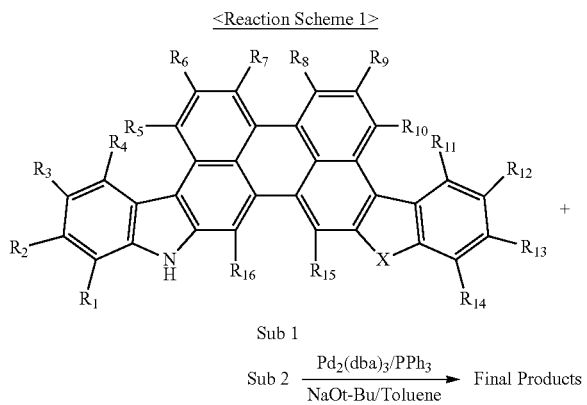

Synthesis Method of Sub 1

Sub 1 of Reaction Scheme 1 can be synthesized according to, but not limited to, the following Reaction Scheme 2 to 4.

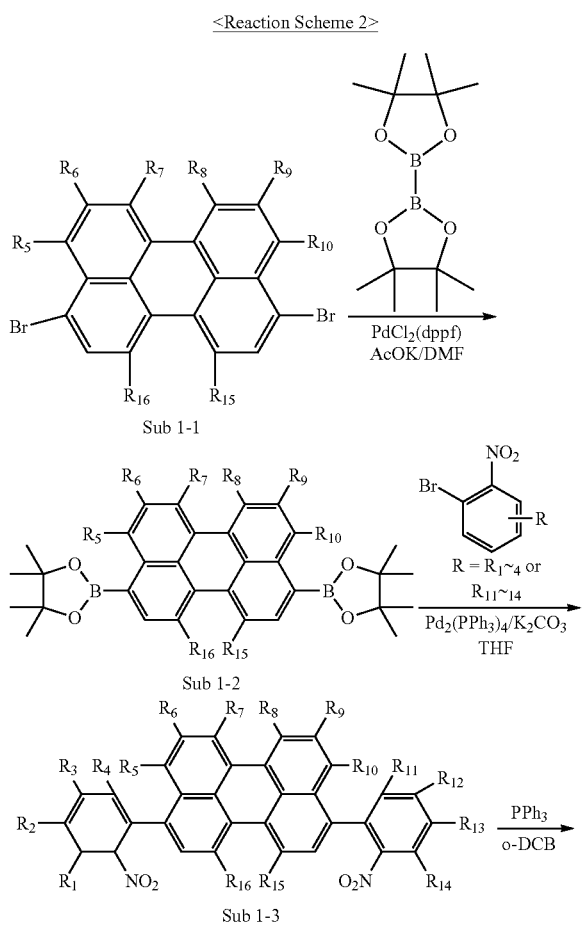

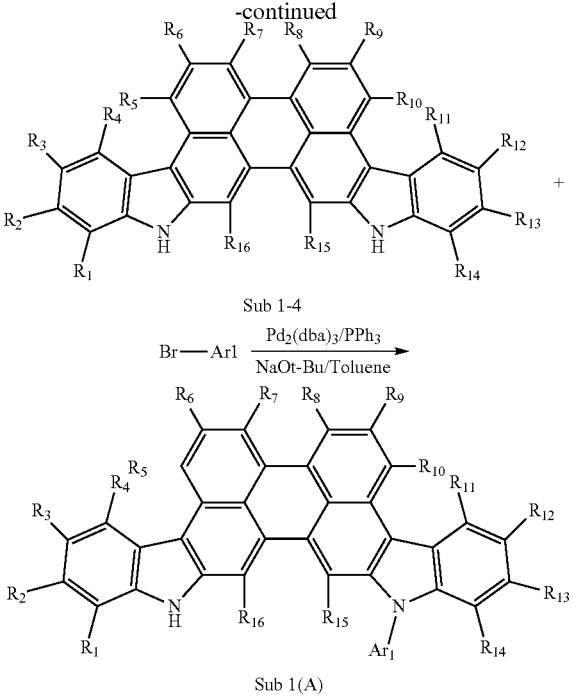

Synthesis Method of Sub 1-2

Sub 1-1 (1eq) was dissolved in DMF in a round bottom flask, and Bis(pinacolato)diboron (2.2eq), Pd(dppf)Cl$_2$ (0.03eq), KOAc (3eq) were added to the reaction solution, followed by stirring at 90° C. After completion of the reaction, DMF was removed under vacuum distillation and the reaction product was extracted with CH$_2$Cl$_2$ and Water. The extracted organic layer was dried with MgSO4 and concentrated, and then the residual was separated by silica gel column and recrystallized to obtain Sub 1-2.

Synthesis Method of Sub 1-3

The obtained Sub 1-2 (1eq) and R substituted 1-bromo-2-nitrobenzene(2eq), Pd(PPh$_3$)$_4$ (0.03eq), K$_2$CO$_3$(3eq) were dissolved in anhydrous DMF and trace amount of water, and then refluxed for 24 hr. After completion of the reaction, the reaction solution was cooled until room temperature, extracted with CH$_2$Cl$_2$. The extracted CH$_2$Cl$_2$ layer was washed with water, dried with MgSO4, filtered under vacuum and then concentrated. And then the residual was separated by silica gel column chromaography to obtain Sub 1-3.

Synthesis Method of Sub 1-4

The obtained Sub 1-3(1eq) and triphenylphosphine (2.5eq) were dissolved in o-dichlorobenzene, and then refluxed for 24 hr. After completion of the reaction, the solvent was removed under vacuum distillation. And then the residual was separated by silica gel column chromaography to obtain Sub 1-4.

Synthesis Method of Sub 1(A)

The obtained Sub 1-4 (1eq) and Br—Ar$_1$ compound (2.5eq) in Toluene was added Pd$_2$(dba)$_3$ (0.05eq), PPh$_3$ (0.1eq), NaOt-Bu (3eq), and then refluxed for 24 hr at 100° C. After completion of the reaction, the reaction solution was extracted with ether and water, dried with MgSO$_4$ and concentrated. And then the residual was separated by silica gel column chromatography and recrystallized to obtain Sub 1(A).

<Reaction Scheme 3>

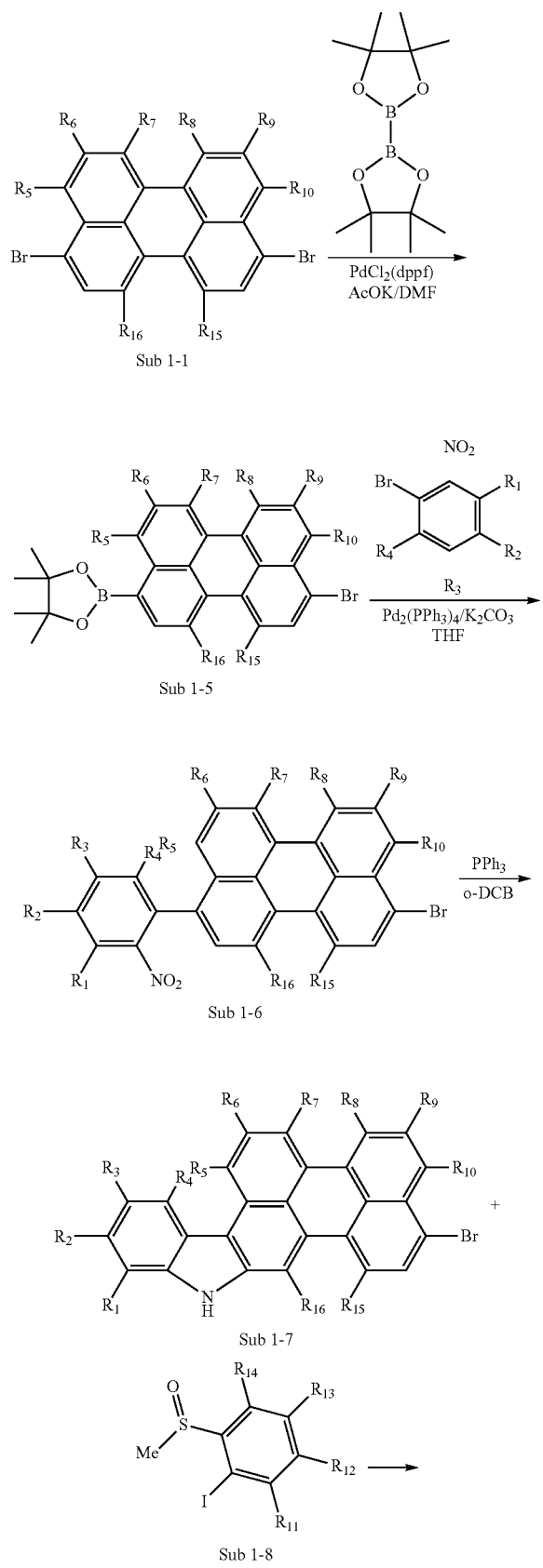

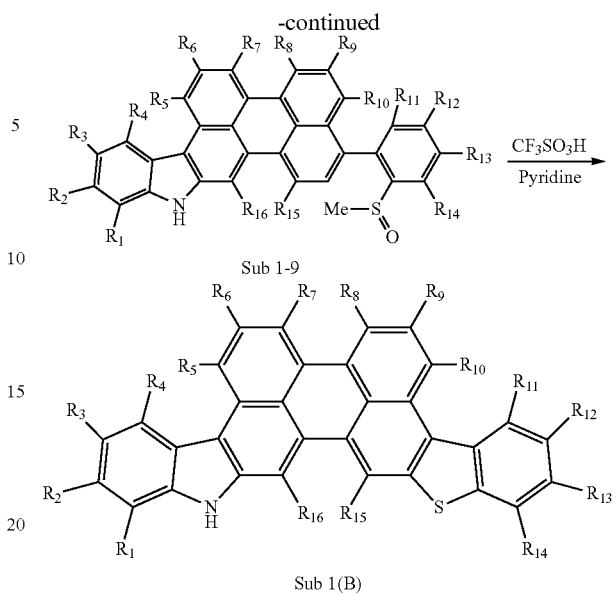

Synthesis Method of Sub 1-5

Sub 1-1(1eq) was dissolved in DMF in a round bottom flask and Bis(pinacolato)diboron (2.2eq), Pd(dppf)Cl$_2$ (0.03eq), KOAc (3eq) were added to the reaction solution, stirred at 90° C. After completion of the reaction, DMF was removed under vacuum distillation and the reaction product was extracted with CH$_2$Cl$_2$ and water. The organic layer was dried with MgSO4 and concentrated, and then the residual was separated by silica gel column and recrystallized to obtain Sub 1-5.

Synthesis Method of 1-6

The obtained Sub 1-5(1eq) and R$_1$~R$_4$ substituted 1-bromo-2-nitrobenzene(1eq), Pd(PPh$_3$)$_4$ (0.03eq), K$_2$CO$_3$ (3eq) were dissolved in anhydrous DMF and trace amount of water, and then refluxed for 24 hr. After completion of the reaction, the reaction solution was cooled until room temperature, extracted with CH$_2$Cl$_2$. The extracted CH$_2$Cl$_2$ layer was washed with water, dried with MgSO4, filtered under vacuum and concentrated. And then the residual was separated by silica gel column chromaography to obtain Sub 1-6.

Synthesis Method of 1-7

The obtained Sub 1-6(1eq) and triphenylphosphine (2.5eq) were dissolved in o-dichlorobenzene, and then refluxed for 24 hr. After completion of the reaction, the solvent was removed under vacuum distillation. And then the residual was separated by silica gel column chromaography to obtain Sub 1-7.

Synthesis Method of 1-9

The obtained Sub 1-7(1eq) and Sub 1-8 (1eq), Ph(PPh$_3$), NaCO$_3$ were dissolved in dried THF and trace amount of water and then refluxed for 24 hr. After completion of the reaction, the reaction solution was cooleded to room temperature, extracted with CH$_2$Cl$_2$. The extracted CH$_2$Cl$_2$ layer was washed with water, dried with MgSO4, filtered under vacuum and concentrated. And then the residual was separated by silica gel column chromaography to obtain Sub 1-9.

Synthesis Method of Sub 1(B)

The obtained Sub 1-9(1eq) was dissolved in trifluoromethanesulfonic acid and then stirred for 48 hr at room temperature. After completion of the reaction, the reaction solution was poured to a mixture of water and pyridine, refluxed for 20 min. After that, the reaction solution was cooled to room temperature, extracted with CH$_2$Cl$_2$. The extracted CH$_2$Cl$_2$ layer was filtered under vacuum, dried with MgSO$_4$ and concentrated. And then the residual was separated by silica gel column chromatography and recrystallized to obtain Sub 1(B).

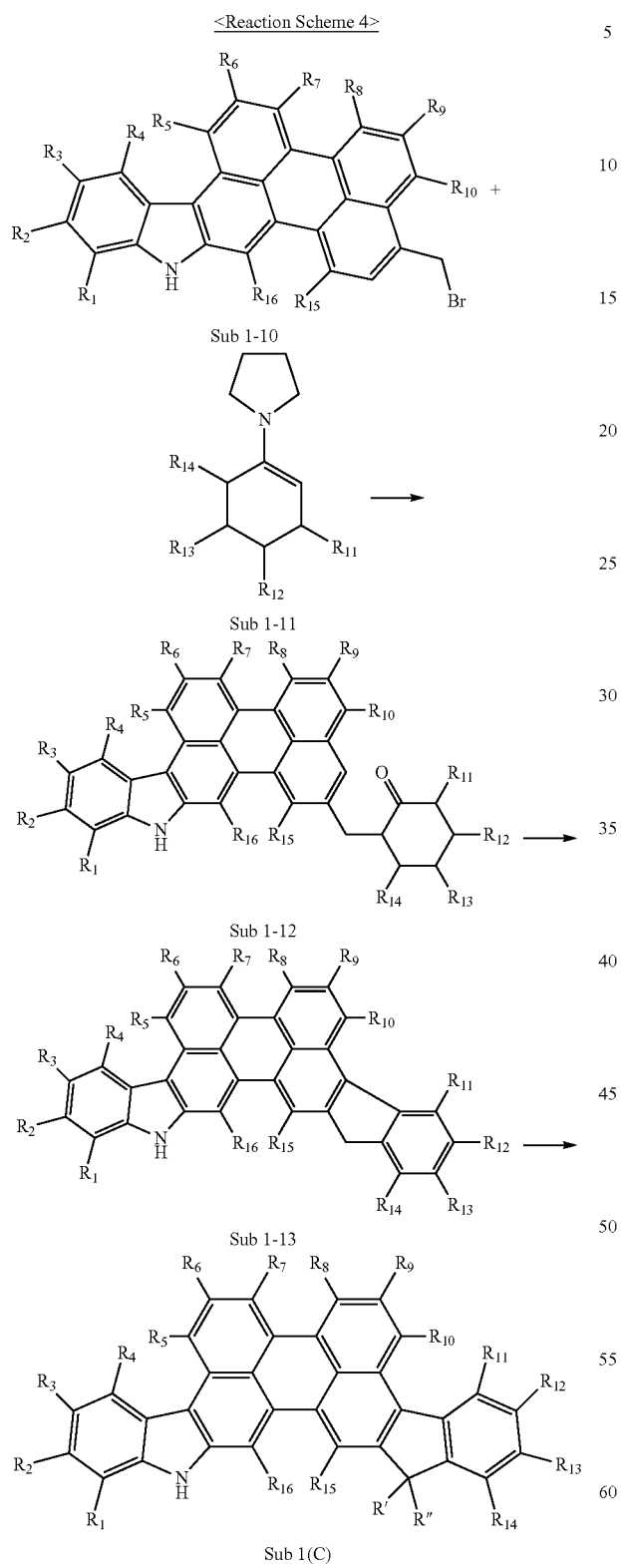

<Reaction Scheme 4>

Sub 1-10

Sub 1-11

Sub 1-12

Sub 1-13

Sub 1(C)

Synthesis Method of 1-12

After Sub 1-10 (1eq) was dissolved in dioxane, R$_{11}$ to R$_{14}$ substituted 1-pyrridino-1-cyclohexne (1.1eq) was added to the solution and the reaction solution was refluxed for 18 hrs. To the reaction solution was added water, heated for 2 hr, worked-up by ether, 5% HCl and 5% NaHCO$_3$ solution. The produced organic material was separated by silica gel column and recrystallized to obtain Sub 1-12.

Synthesis Method of 1-13

Sub 1-12 was dissolved in a mixture of CHCl$_3$ and 10% methansulfonic acid solution and stirred for 2 hr at room temperature. The reaction was stopped by adding sodium bicarbonate solution, and then extracted with CH$_2$Cl$_2$, washed with NaHCO$_3$ and water. After removing the solvent, the produced organic material was separated by following column chromatography and refluxed for 16 hrs after dissolving 10% pd/C in triglym. After that, the reaction solution was performed column chromatography by hexane to obtain Sub 1-13.

Synthesis Method of Sub 1(C)

To a solution of Sub 1-13(1eq) in THF was added n-BuLi 1.6M in hexane (1.1eq) at −78° C. The solution was stirred for 1 hr and added iodomethane(1.3eq). The reaction solution was slowly warmed to the room temperature and additionally stirred for 1 hr at room temperature. The temperature of the reaction solution was lowered to −78° C., and n-BuLi 1.6M in hexane (1.1eq) was slowly added thereto, stirred for 1 hr, added iodomethane(1.3eq). After the temperature of the reaction solution was warmed to room temperature, the solution was stirred for 15 hr at the same temperature. After that, to the reaction solution was added ammonium chloride solution and distilled water to end the reaction. The organic layer was concentrated under vacuum and recrystallized to obtain Sub 1(C).

Examples of Sub 1 compounds include, but are not limited to, the following compounds.

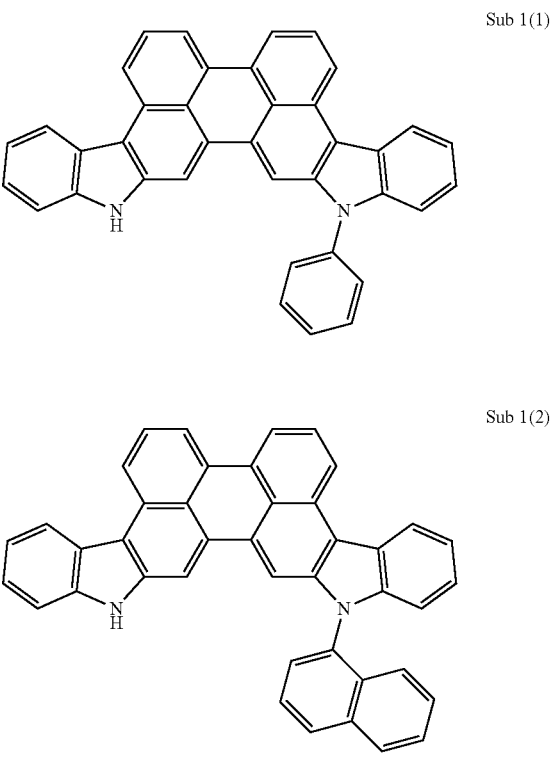

Sub 1(1)

Sub 1(2)

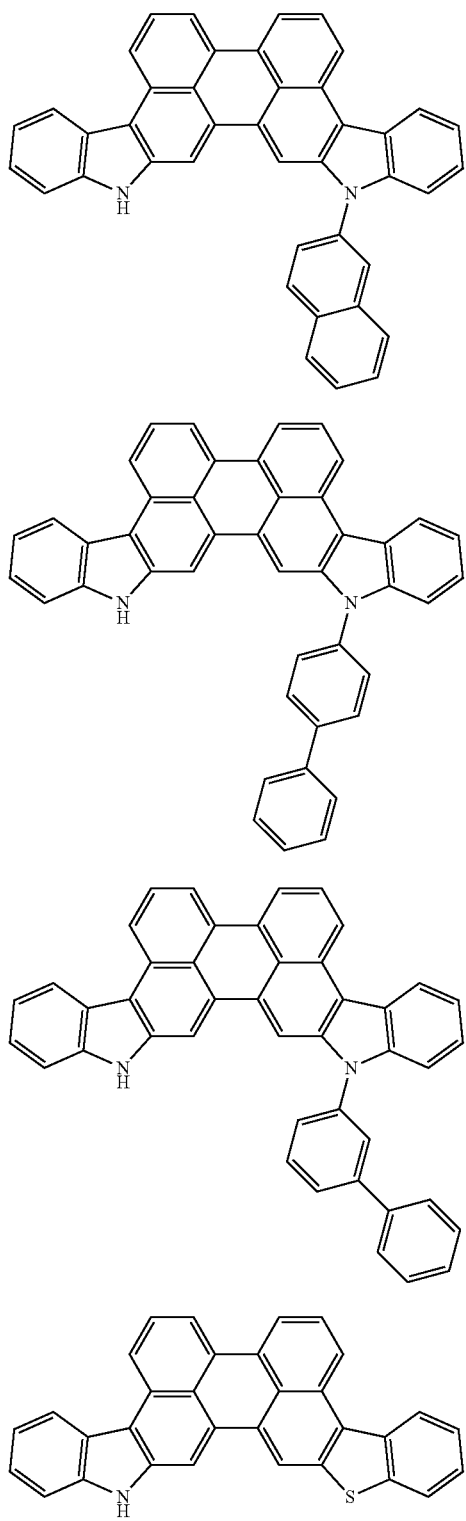
TABLE 1
| Compound | FD-MS | Compound | FD-MS |
| --- | --- | --- | --- |
| Sub 1(1) | m/z = 506.18($C_{38}H_{22}N_2$ = 506.59) | Sub 1(2) | m/z = 556.19($C_{42}H_{24}N_2$ = 556.65) |
| Sub 1(3) | m/z = 556.19($C_{42}H_{24}N_2$ = 556.65) | Sub 1(4) | m/z = 582.21($C_{44}H_{26}N_2$ = 582.69) |
| Sub 1(5) | m/z = 582.21($C_{44}H_{26}N_2$ = 582.69) | Sub 1(6) | m/z = 447.11($C_{32}H_{17}NS$ = 447.55) |

TABLE 1-continued
| Compound | FD-MS | Compound | FD-MS |
|---|---|---|---|
| Sub 1(7) | m/z = 431.13($C_{32}H_{17}NO$ = 431.48) | Sub 1(8) | m/z = 457.18($C_{35}H_{23}N$ = 457.56) |
| Sub 1(9) | m/z = 527.21($C_{45}H_{27}N$ = 581.70) | Sub 1(10) | m/z = 579.20($C_{45}H_{25}N$ = 579.69) |
Examples of Sub 2
Examples of Sub 2 compounds include, but are not limited to, the following compounds.
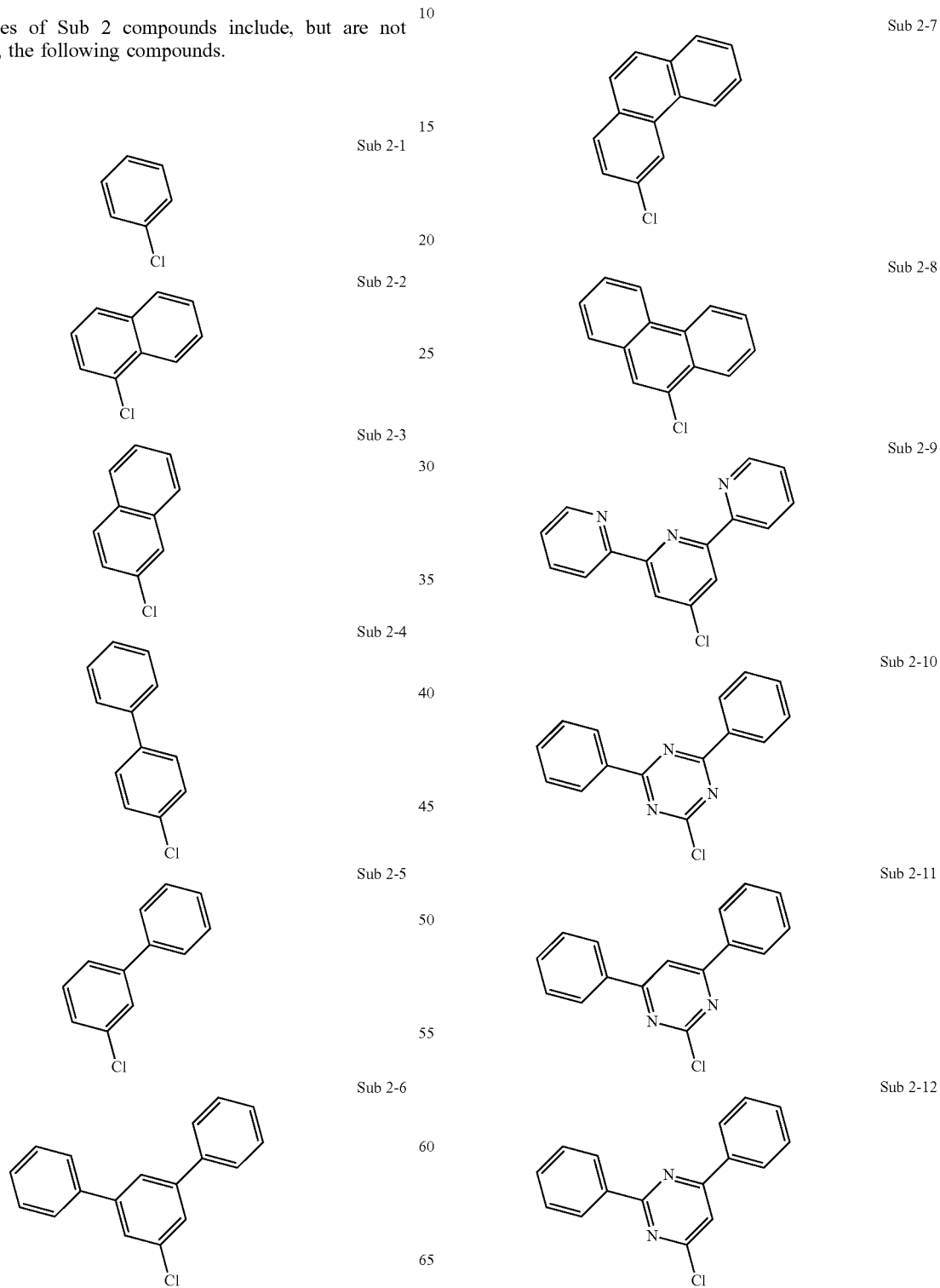

-continued
Sub 2-13
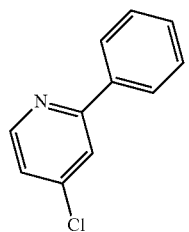
Sub 2-14
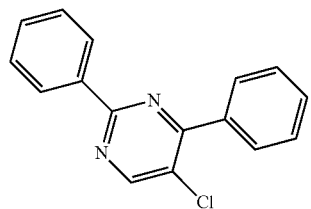
Sub 2-15
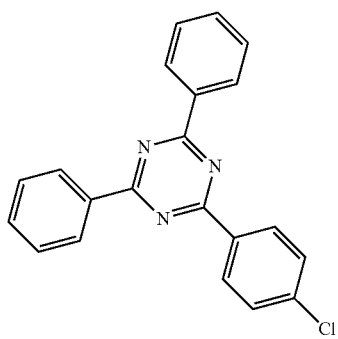
Sub 2-16
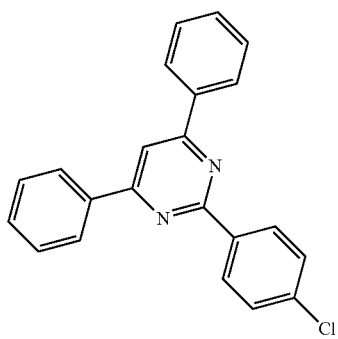
Sub 2-17
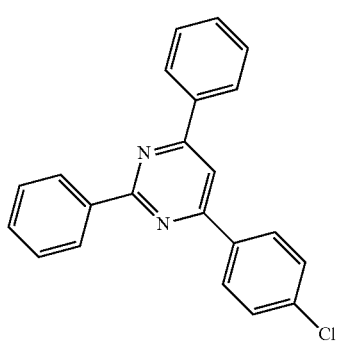
-continued
Sub 2-18
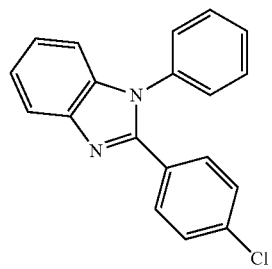
Sub 2-19
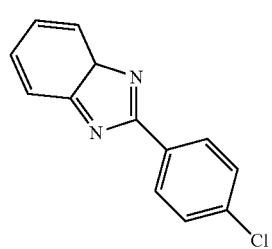
Sub 2-20
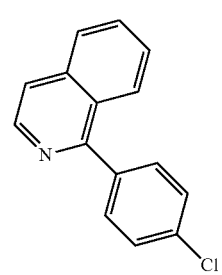
Sub 2-21
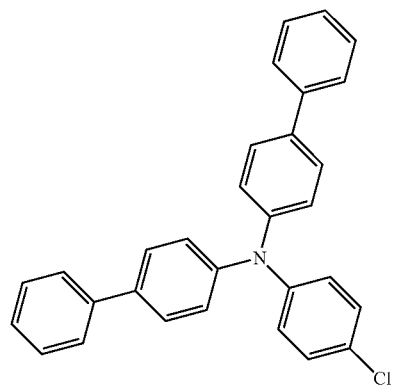
Sub 2-22
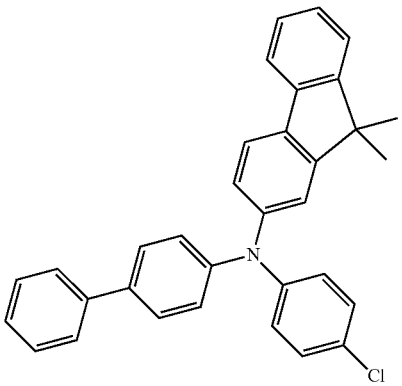

-continued
Sub 2-23
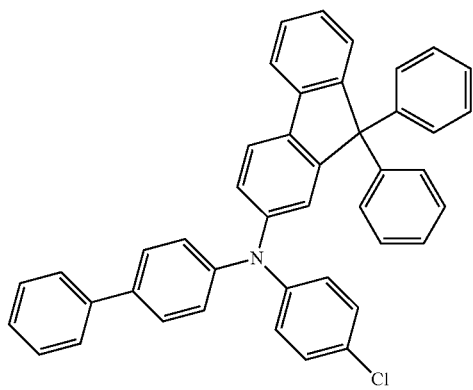
Sub 2-24
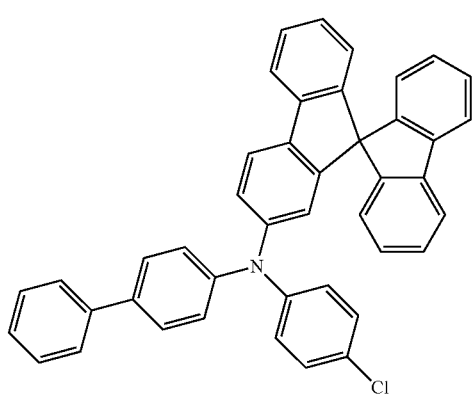
Sub 2-25
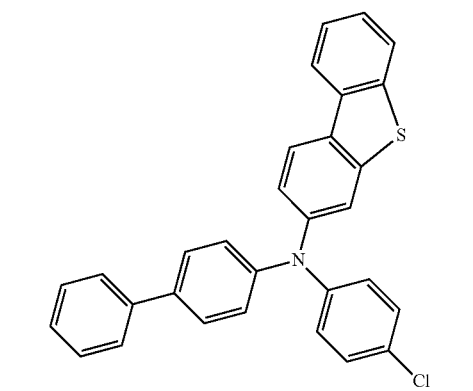
Sub 2-26
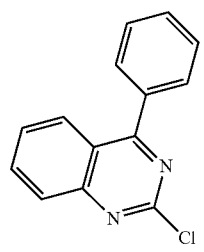
Sub 2-27
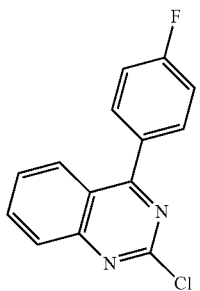
Sub 2-28
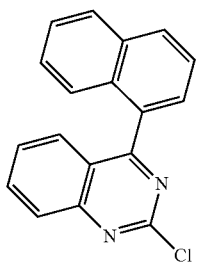
Sub 2-29
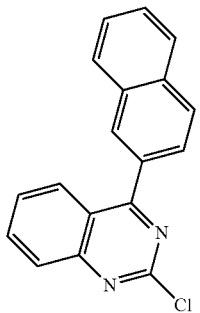
Sub 2-30
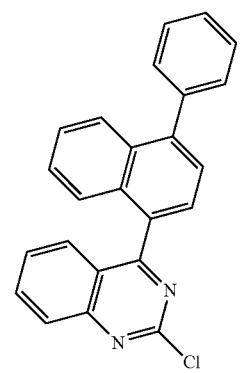
Sub 2-31
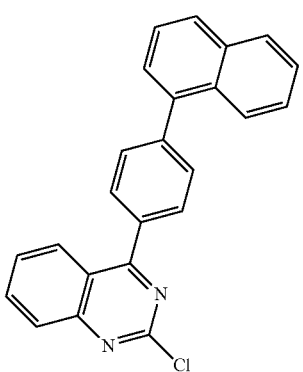

-continued
Sub 2-32
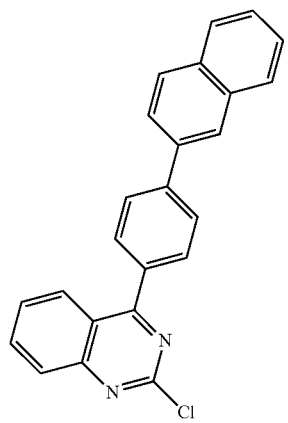
Sub 2-33
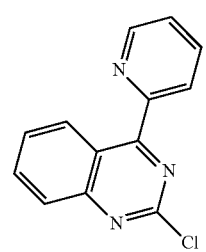
Sub 2-34
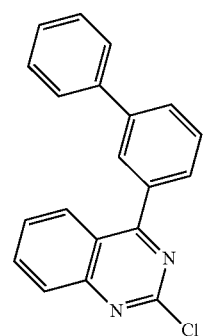
Sub 2-35
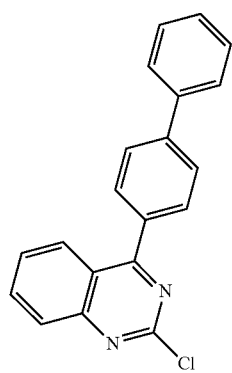
Sub 2-36
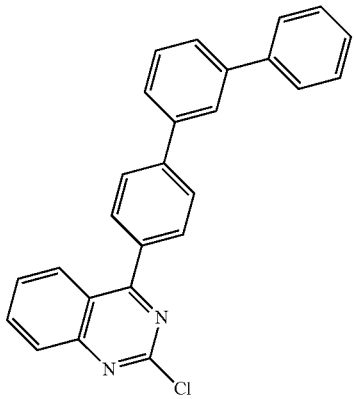
Sub 2-37
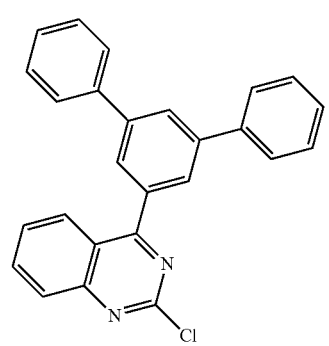
Sub 2-38
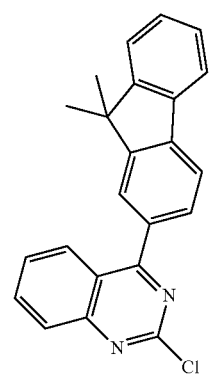
Sub 2-39
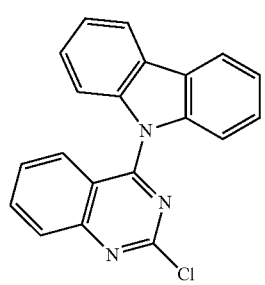

Sub 2-40 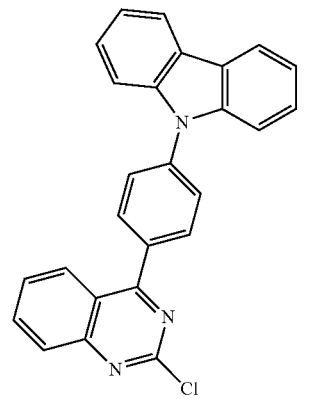
Sub 2-41 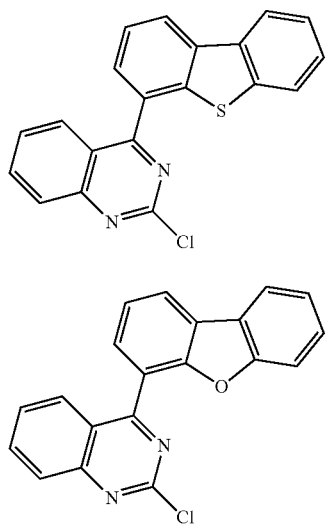
Sub 2-42
Sub 2-43 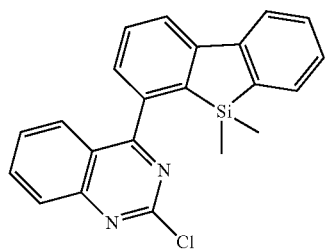
Sub 2-44 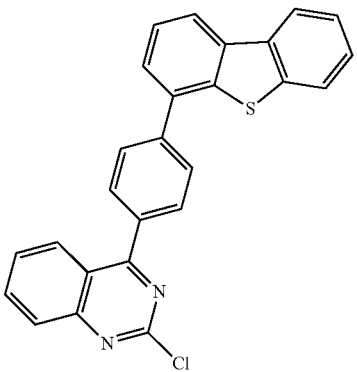
Sub 2-45 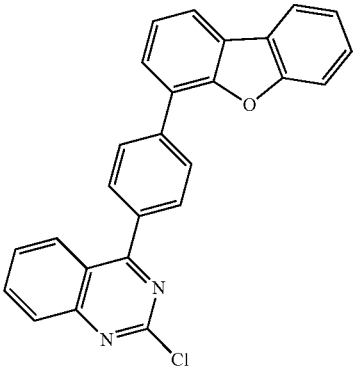
Sub 2-46 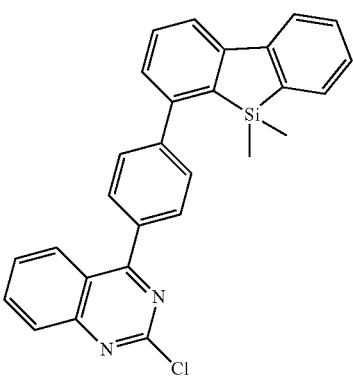
Sub 2-47 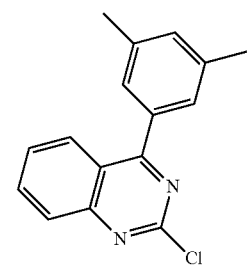
Sub 2-48 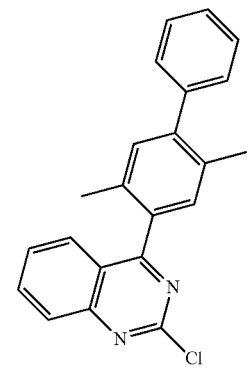

-continued
Sub 2-49
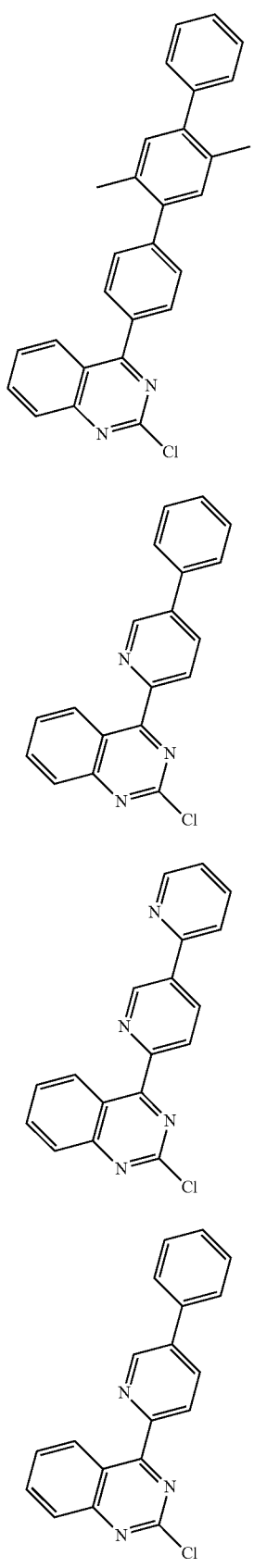
Sub 2-50
Sub 2-51
Sub 2-52
-continued
Sub 2-53
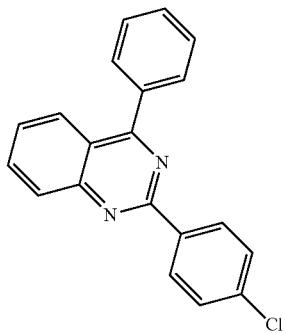
Sub 2-54
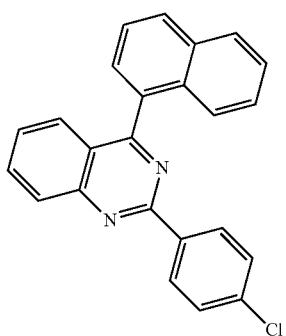
Sub 2-55
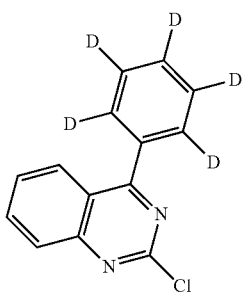
Sub 2-56
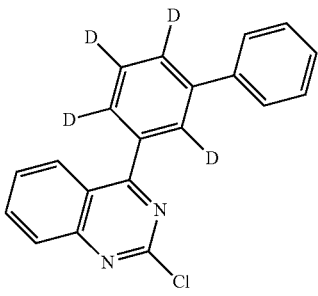
Sub 2-57
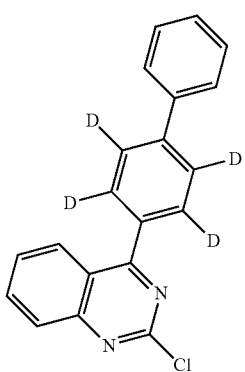

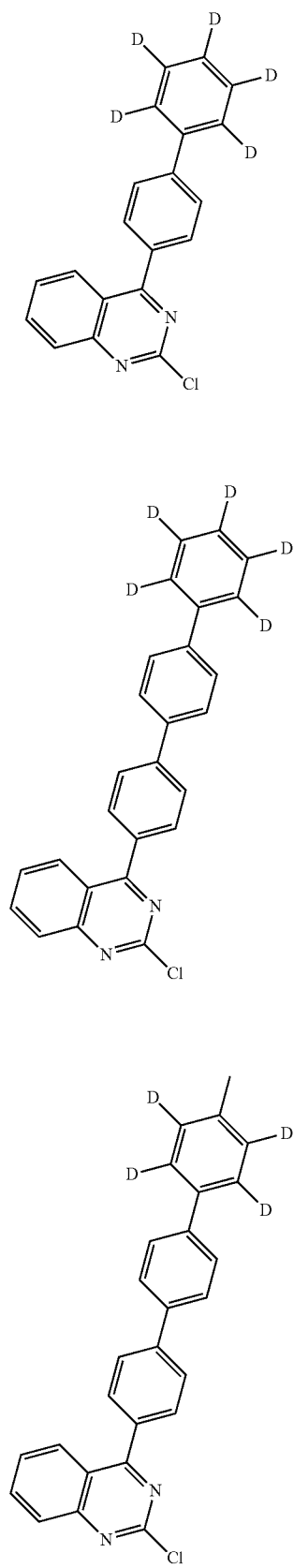
Sub 2-58
Sub 2-59
Sub 2-60
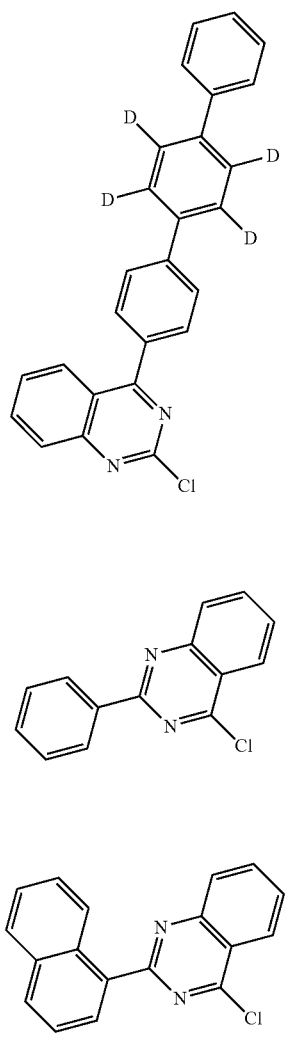
Sub 2-61
Sub 2-62
Sub 2-63
Sub 2-64
Sub 2-65
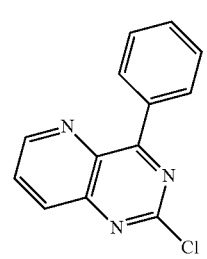

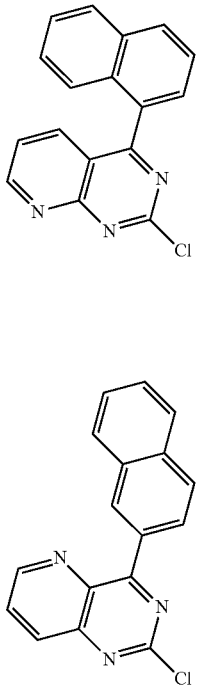

Sub 2-66

Sub 2-67

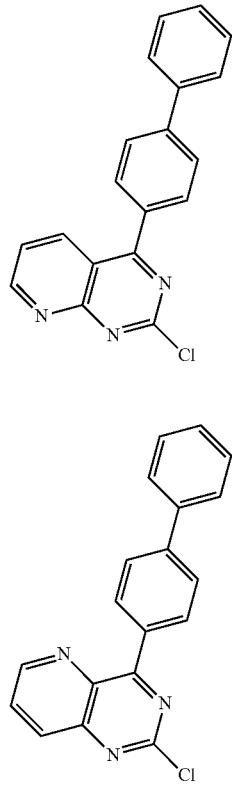

Sub 2-68

Sub 2-69

TABLE 2

| Compound | FD-MS | Compound | FD-MS |
|---|---|---|---|
| Sub 2-1 | m/z = 112.01($C_6H_5Cl$ = 112.56) | Sub 2-2 | m/z = 162.02($C_{10}H_7Cl$ = 162.62) |
| Sub 2-3 | m/z = 188.04($C_{12}H_9Cl$ = 188.65) | Sub 2-4 | m/z = 188.04($C_{12}H_9Cl$ = 188.65) |
| Sub 2-5 | m/z = 188.04($C_{12}H_9Cl$ = 188.65) | Sub 2-6 | m/z = 212.04($C_{14}H_9Cl$ = 212.67) |
| Sub 2-7 | m/z = 212.04($C_{14}H_9Cl$ = 212.67) | Sub 2-8 | m/z = 212.04($C_{14}H_9Cl$ = 212.67) |
| Sub 2-9 | m/z = 267.06($C_{15}H_{10}ClN_3$ = 267.71) | Sub 2-10 | m/z = 267.06($C_{15}H_{10}ClN_3$ = 267.71) |
| Sub 2-11 | m/z = 266.06($C_{16}H_{11}ClN_2$ = 266.72) | Sub 2-12 | m/z = 266.06($C_{16}H_{11}ClN_2$ = 266.72) |
| Sub 2-13 | m/z = 189.03($C_{11}H_8ClN$ = 189.64) | Sub 2-14 | m/z = 266.06($C_{16}H_{11}ClN_2$ = 266.72) |
| Sub 2-15 | m/z = 343.09($C_{21}H_{14}ClN_3$ = 343.81) | Sub 2-16 | m/z = 342.09($C_{22}H_{15}ClN_2$ = 342.82) |
| Sub 2-17 | m/z = 342.09($C_{22}H_{15}ClN_2$ = 342.82) | Sub 2-18 | m/z = 304.08($C_{19}H_{13}ClN_2$ = 304.77) |
| Sub 2-19 | m/z = 228.05($C_{13}H_9ClN_2$ = 228.68) | Sub 2-20 | m/z = 239.05($C_{15}H_{10}ClN$ = 239.70) |
| Sub 2-21 | m/z = 431.14($C_{30}H_{22}ClN$ = 431.96) | Sub 2-22 | m/z = 471.18($C_{33}H_{26}ClN$ = 472.02) |
| Sub 2-23 | m/z = 595.21($C_{43}H_{30}ClN$ = 596.16) | Sub 2-24 | m/z = 593.19($C_{43}H_{28}ClN$ = 594.14) |
| Sub 2-25 | m/z = 461.10($C_{30}H_{20}ClNS$ = 462.00) | Sub 2-26 | m/z = 240.05($C_{14}H_9ClN_2$ = 240.69) |
| Sub 2-27 | m/z = 258.04($C_{14}H_8ClFN_2$ = 258.68) | Sub 2-28 | m/z = 290.06($C_{18}H_{11}ClN_2$ = 290.75) |
| Sub 2-29 | m/z = 290.06($C_{18}H_{11}ClN_2$ = 290.75) | Sub 2-30 | m/z = 366.09($C_{24}H_{15}ClN_2$ = 366.84) |
| Sub 2-31 | m/z = 366.09($C_{24}H_{15}ClN_2$ = 366.84) | Sub 2-32 | m/z = 366.09($C_{24}H_{15}ClN_2$ = 366.84) |
| Sub 2-33 | m/z = 241.04($C_{13}H_8ClN_3$ = 241.68) | Sub 2-34 | m/z = 316.08($C_{20}H_{13}ClN_2$ = 316.78) |
| Sub 2-35 | m/z = 316.08($C_{20}H_{13}ClN_2$ = 316.78) | Sub 2-36 | m/z = 392.11($C_{26}H_{17}ClN_2$ = 392.88) |
| Sub 2-37 | m/z = 392.11($C_{26}H_{17}ClN_2$ = 392.88) | Sub 2-38 | m/z = 356.11($C_{23}H_{17}ClN_2$ = 356.85) |
| Sub 2-39 | m/z = 329.07($C_{20}H_{12}ClN_3$ = 329.78) | Sub 2-40 | m/z = 405.10($C_{26}H_{16}ClN_3$ = 405.88) |
| Sub 2-41 | m/z = 346.03($C_{20}H_{11}ClN_2S$ = 346.83) | Sub 2-42 | m/z = 330.06($C_{20}H_{11}ClN_2O$ = 330.77) |
| Sub 2-43 | m/z = 372.08($C_{22}H_{17}ClN_2Si$ = 372.92) | Sub 2-44 | m/z = 422.06($C_{26}H_{15}ClN_2S$ = 422.93) |
| Sub 2-45 | m/z = 406.09($C_{26}H_{15}ClN_2O$ = 406.86) | Sub 2-46 | m/z = 448.12($C_{28}H_{21}ClN_2Si$ = 449.02) |
| Sub 2-47 | m/z = 268.08($C_{16}H_{13}ClN_2$ = 268.74) | Sub 2-48 | m/z = 420.14($C_{28}H_{21}ClN_2$ = 344.84) |
| Sub 2-49 | m/z = 420.14($C_{28}H_{21}ClN_2$ = 420.93) | Sub 2-50 | m/z = 317.07($C_{19}H_{12}ClN_3$ = 317.77) |
| Sub 2-51 | m/z = 318.07($C_{18}H_{11}ClN_4$ = 318.76) | Sub 2-52 | m/z = 317.07($C_{19}H_{12}ClN_3$ = 317.77) |
| Sub 2-53 | m/z = 316.08($C_{20}H_{13}ClN_2$ = 316.78) | Sub 2-54 | m/z = 366.09($C_{24}H_{15}ClN_2$ = 366.84) |
| Sub 2-55 | m/z = 245.08($C_{14}H_4D_5ClN_2$ = 245.72) | Sub 2-56 | m/z = 320.10($C_{20}H_5D_4ClN_2$ = 320.81) |
| Sub 2-57 | m/z = 320.10($C_{20}H_5D_4ClN_2$ = 320.81) | Sub 2-58 | m/z = 320.10($C_{20}H_5D_4ClN_2$ = 320.81) |
| Sub 2-59 | m/z = 397.14($C_{26}H_{12}D_5ClN_2$ = 397.9) | Sub 2-60 | m/z = 410.15($C_{27}H_{15}D_4ClN_2$ = 410.93) |
| Sub 2-61 | m/z = 396.13($C_{26}H_{13}D_4ClN_2$ = 396.9) | Sub 2-62 | m/z = 240.05($C_{14}H_9ClN_2$ = 240.69) |
| Sub 2-63 | m/z = 290.06($C_{18}H_{11}ClN_2$ = 290.75) | Sub 2-64 | m/z = 241.04($C_{13}H_8ClN_3$ = 241.68) |
| Sub 2-65 | m/z = 241.04($C_{13}H_8ClN_3$ = 241.68) | Sub 2-66 | m/z = 291.06($C_{17}H_{10}ClN_3$ = 291.73) |
| Sub 2-67 | m/z = 291.06($C_{17}H_{10}ClN_3$ = 291.73) | Sub 2-68 | m/z = 317.07($C_{19}H_{12}ClN_3$ = 317.77) |
| Sub 2-69 | m/z = 317.07($C_{19}H_{12}ClN_3$ = 317.77) | | |

Synthesis Method of Final Product

To a solution of Sub 1 (1eq) and Sub 2 (1.1eq) in Toluene, was added Pd$_2$(dba)$_3$ (0.05eq) PPh$_3$ (0.1eq), NaOt-Bu (3eq), refluxed for 24 hr at 100° C. After completion of the reaction, the reaction solution was extracted with ether and water, dried with MgSO$_4$ and concentrated. The produced organic material was separated by silica gel column chromatography and recrystallized to obtain Final product.

Synthesis Method of 1-1

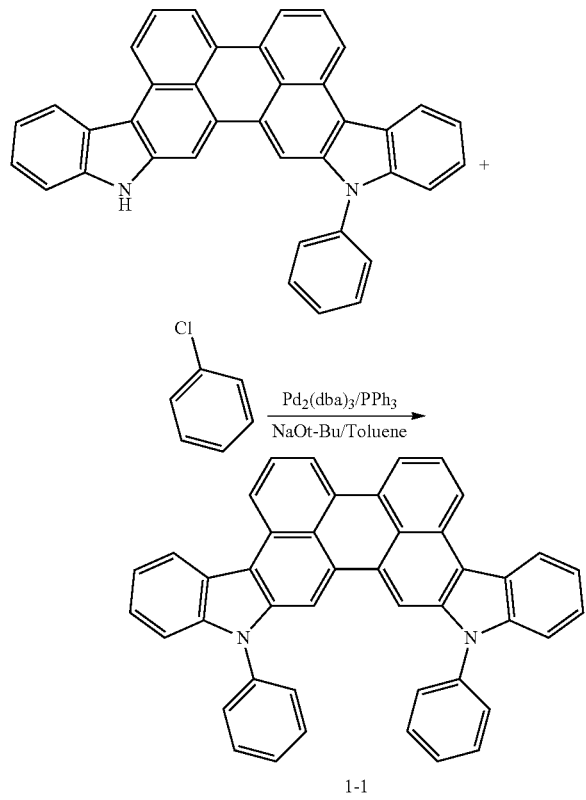

1-1

To a solution of 15-phenyl-15,18-dihydrophenanthro[9,8-bc:10,1-b'c']dicarbazole (10.1 g, 20 mmol) and chlorobenzene (2.7 g, 24 mmol) in Toluene was added Pd$_2$(dba)$_3$ (1.0 g, 1 mmol), PPh$_3$ (0.5 g, 2 mmol), NaOt-Bu (5.8 g, 60 mmol) and refluxed for 24 hr at 100° C. After completion of the reaction, the reaction solution was extracted with ether and water, dried with MgSO$_4$ and concentrated. The produced organic material was separated by silica gel column chromatography and recrystallized to obtain 7.8 g of Final product (yield: 67%).

Synthesis Method of 2-1

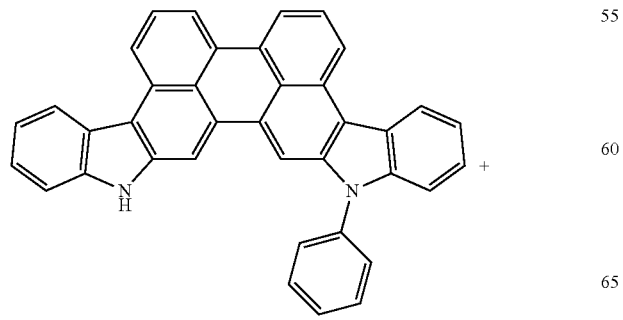

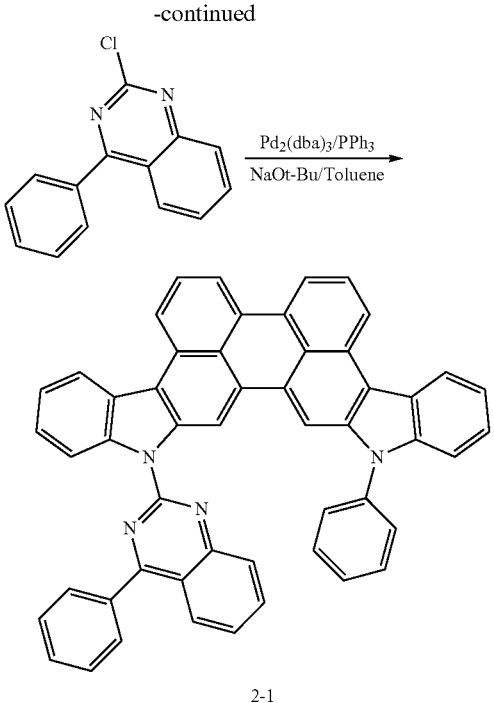

2-1

To a solution of 15-phenyl-15,18-dihydrophenanthro[9,8-bc:10,1-b'c']dicarbazole (10.1 g, 20 mmol) and 2-chloro-4-phenylquinazoline (5.8 g, 24 mmol) in Toluene was added Pd$_2$(dba)$_3$ (1.0 g, 1 mmol), PPh$_3$ (0.5 g, 2 mmol), NaOt-Bu (5.8 g, 60 mmol) and refluxed for 24 hr at 100° C. After completion of the reaction, the reaction solution was extracted with ether and water, dried with MgSO$_4$ and concentrated. The produced organic material was separated by silica gel column chromatography and recrystallized to obtain 9.0 g of Final product (yield: 63%).

Synthesis Method of 3-5

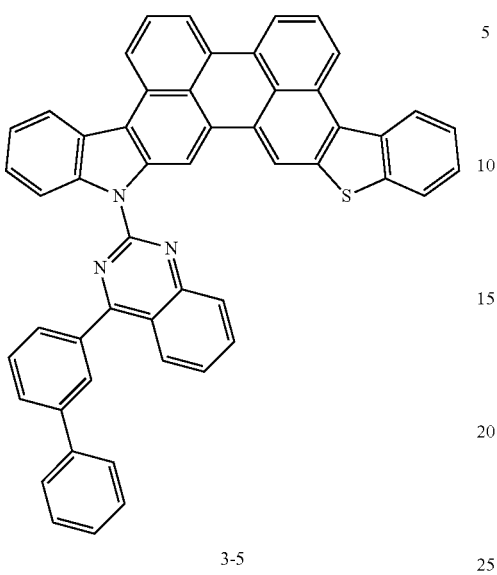

3-5

To a solution of 18H-benzo[5,10]benzo[4',5']thieno[3',2': 6,7]anthra[9,1-bc]carbazole (8.9 g, 20 mmol) and 4-([1,1'-biphenyl]-3-yl)-2-chloroquinazoline (7.6 g, 24 mmol) in Toluene was added Pd$_2$(dba)$_3$ (1.0 g, 1 mmol), PPh$_3$ (0.5 g, 2 mmol), NaOt-Bu (5.8 g, 60 mmol) and refluxed for 24 hr at 100° C. After completion of the reaction, the reaction solution was extracted with ether and water, dried with MgSO$_4$ and concentrated. The produced organic material was separated by silica gel column chromatography and recrystallized to obtain 9.5 g of Final product (yield: 65%).

Synthesis Method of 4-4

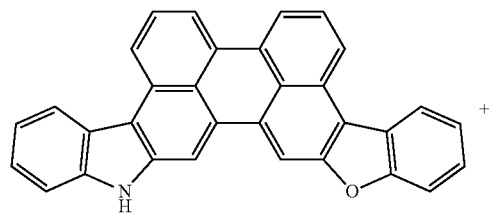

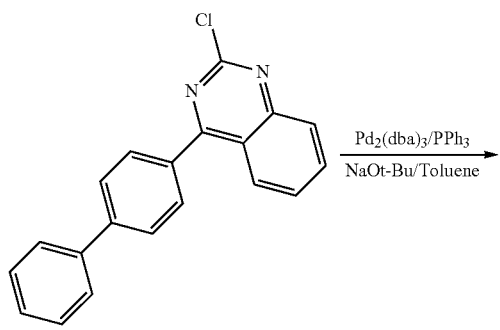

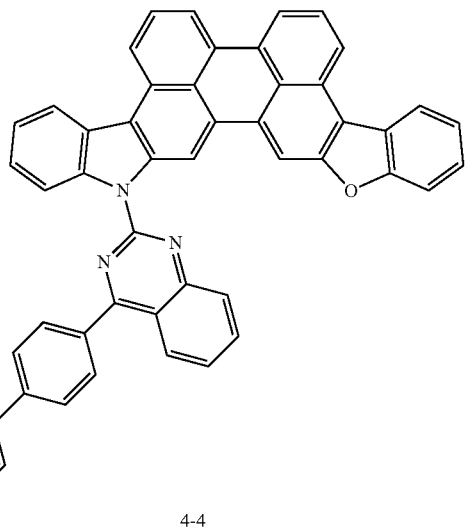

4-4

To a solution of 18H-benzo[5,10]benzofuro[3',2':6,7]anthra[9,1-bc]carbazole (8.6 g, 20 mmol) and 4-([1,1'-biphenyl]-4-yl)-2-chloroquinazoline (7.6 g, 24 mmol) in Toluene was added Pd$_2$(dba)$_3$ (1.0 g, 1 mmol), PPh$_3$ (0.5 g, 2 mmol), NaOt-Bu (5.8 g, 60 mmol) and refluxed for 24 hr at 100° C. After completion of the reaction, the reaction solution was extracted with ether and water, dried with MgSO$_4$ and concentrated. The produced organic material was separated by silica gel column chromatography and recrystallized to obtain 8.7 g of Final product (yield: 61%).

Synthesis Method of 5-15

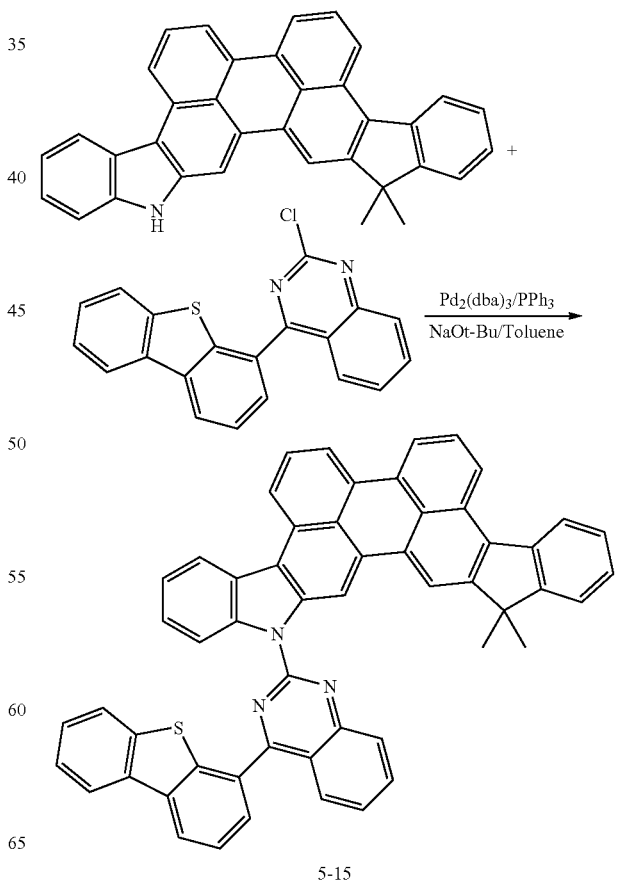

5-15

To a solution of 18,18-dimethyl-15,18-dihydrobenzo[5,10]indeno[1',2':6,7]anthra[9,1-bc]carbazole (9.2 g, 20 mmol) and 42-chloro-4-(dibenzo[b,d]thiophen-4-yl)quinazoline (8.3 g, 24 mmol) in Toluene was added Pd$_2$(dba)$_3$ (1.0 g, 1 mmol), PPh$_3$ (0.5 g, 2 mmol), NaOt-Bu (5.8 g, 60 mmol) and refluxed for 24 hr at 100° C. After completion of the reaction, the reaction solution was extracted with ether and water, dried with MgSO$_4$ and concentrated. The produced organic material was separated by silica gel column chromatography and recrystallized to obtain 8.9 g of Final product (yield: 58%).

TABLE 3

| Compound | FD-MS | Compound | FD-MS |
|---|---|---|---|
| 1-1 | m/z = 582.21(C$_{44}$H$_{26}$N$_2$ = 582.69) | 1-2 | m/z = 632.23(C$_{48}$H$_{28}$N$_2$ = 632.75) |
| 1-3 | m/z = 632.23(C$_{48}$H$_{28}$N$_2$ = 632.75) | 1-4 | m/z = 658.24(C$_{50}$H$_{30}$N$_2$ = 658.79) |
| 1-5 | m/z = 523.14(C$_{38}$H$_{21}$NS = 523.65) | 1-6 | m/z = 573.16(C$_{42}$H$_{23}$NS = 573.70) |
| 1-7 | m/z = 573.16(C$_{42}$H$_{23}$NS = 573.70) | 1-8 | m/z = 599.17(C$_{44}$H$_{25}$NS = 599.74) |
| 1-9 | m/z = 507.16(C$_{38}$H$_{21}$NO = 507.58) | 1-10 | m/z = 557.18(C$_{42}$H$_{23}$NO = 557.64) |
| 1-11 | m/z = 557.18(C$_{42}$H$_{23}$NO = 557.64) | 1-12 | m/z = 583.19(C$_{44}$H$_{25}$NO = 583.68) |
| 1-13 | m/z = 533.21(C$_{41}$H$_{27}$N = 533.66) | 1-14 | m/z = 583.23(C$_{45}$H$_{29}$N = 583.72) |
| 1-15 | m/z = 707.26(C$_{55}$H$_{33}$N = 707.86) | 1-16 | m/z = 731.26(C$_{57}$H$_{33}$N = 731.88) |
| 1-17 | m/z = 464.07(C$_{32}$H$_{16}$N$_2$ = 464.60) | 1-18 | m/z = 448.09(C$_{32}$H$_{16}$OS = 448.53) |
| 1-19 | m/z = 474.14(C$_{35}$H$_{22}$S = 474.61) | 1-20 | m/z = 598.18(C$_{45}$H$_{26}$S = 598.75) |
| 1-21 | m/z = 432.12(C$_{32}$H$_{16}$O$_2$ = 432.47) | 1-22 | m/z = 458.17(C$_{35}$H$_{22}$O = 458.55) |
| 1-23 | m/z = 582.20(C$_{45}$H$_{26}$O = 582.69) | 1-24 | m/z = 484.22(C$_{38}$H$_{28}$ = 484.63) |
| 1-25 | m/z = 608.25(C$_{48}$H$_{32}$ = 608.77) | 1-26 | m/z = 606.23(C$_{48}$H$_{30}$ = 606.75) |
| 1-27 | m/z = 732.28(C$_{58}$H$_{36}$ = 732.91) | 1-28 | m/z = 728.25(C$_{58}$H$_{32}$ = 728.87) |
| 1-29 | m/z = 736.26(C$_{54}$H$_{32}$N$_4$ = 736.86) | 1-30 | m/z = 737.26(C$_{53}$H$_{31}$N$_5$ = 737.85) |
| 1-31 | m/z = 677.19(C$_{48}$H$_{27}$N$_3$S = 677.81) | 1-32 | m/z = 678.19(C$_{47}$H$_{26}$N$_4$S = 678.80) |
| 1-33 | m/z = 661.22(C$_{48}$H$_{27}$N$_3$O = 661.75) | 1-34 | m/z = 662.21(C$_{47}$H$_{26}$N$_4$O = 667.74) |
| 1-35 | m/z = 687.27(C$_{51}$H$_{33}$N$_3$ = 687.83) | 1-36 | m/z = 688.26(C$_{50}$H$_{32}$N$_4$ = 688.82) |
| 2-1 | m/z = 710.25(C$_{52}$H$_{30}$N$_4$ = 710.82) | 2-2 | m/z = 760.26(C$_{56}$H$_{32}$N$_4$ = 760.88) |
| 2-3 | m/z = 760.26(C$_{56}$H$_{32}$N$_4$ = 760.88) | 2-4 | m/z = 786.28(C$_{58}$H$_{34}$N$_4$ = 786.92) |
| 2-5 | m/z = 786.28(C$_{58}$H$_{34}$N$_4$ = 786.92) | 2-6 | m/z = 715.28(C$_{52}$H$_{25}$D$_5$N$_4$ = 715.85) |
| 2-7 | m/z = 836.29(C$_{62}$H$_{36}$N$_4$ = 836.98) | 2-8 | m/z = 836.29(C$_{62}$H$_{36}$N$_4$ = 836.98) |
| 2-9 | m/z = 836.29(C$_{62}$H$_{36}$N$_4$ = 836.98) | 2-10 | m/z = 836.29(C$_{62}$H$_{36}$N$_4$ = 836.98) |
| 2-11 | m/z = 810.28(C$_{60}$H$_{34}$N$_4$ = 810.94) | 2-12 | m/z = 826.31(C$_{61}$H$_{38}$N$_4$ = 826.98) |
| 2-13 | m/z = 816.23(C$_{58}$H$_{32}$N$_4$S = 816.97) | 2-14 | m/z = 875.30(C$_{64}$H$_{37}$N$_5$ = 876.01) |
| 2-15 | m/z = 810.28(C$_{60}$H$_{34}$N$_4$ = 810.94) | 2-16 | m/z = 810.28(C$_{60}$H$_{34}$N$_4$ = 840.94) |
| 2-17 | m/z = 836.29(C$_{62}$H$_{36}$N$_4$ = 836.98) | 2-18 | m/z = 836.29(C$_{62}$H$_{36}$N$_4$ = 836.98) |
| 2-19 | m/z = 765.29(C$_{56}$H$_{27}$D$_5$N$_4$ = 765.91) | 2-20 | m/z = 886.31(C$_{66}$H$_{38}$N$_4$ = 887.03) |
| 2-21 | m/z = 886.31(C$_{66}$H$_{38}$N$_4$ = 887.03) | 2-22 | m/z = 886.31(C$_{66}$H$_{38}$N$_4$ = 887.03) |
| 2-23 | m/z = 886.31(C$_{66}$H$_{38}$N$_4$ = 887.03) | 2-24 | m/z = 860.29(C$_{64}$H$_{36}$N$_4$ = 861.00) |
| 2-25 | m/z = 876.33(C$_{65}$H$_{40}$N$_4$ = 877.04) | 2-26 | m/z = 866.25(C$_{62}$H$_{34}$N$_4$S = 867.03) |
| 2-27 | m/z = 925.32(C$_{68}$H$_{39}$N$_5$ = 926.07) | 2-28 | m/z = 810.28(C$_{60}$H$_{34}$N$_4$ = 810.94) |
| 2-29 | m/z = 836.29(C$_{62}$H$_{36}$N$_4$ = 836.98) | 2-30 | m/z = 836.29(C$_{62}$H$_{36}$N$_4$ = 836.98) |
| 2-31 | m/z = 765.29(C$_{56}$H$_{27}$D$_5$N$_4$ = 765.91) | 2-32 | m/z = 886.31(C$_{66}$H$_{38}$N$_4$ = 887.03) |
| 2-33 | m/z = 886.31(C$_{66}$H$_{38}$N$_4$ = 887.03) | 2-34 | m/z = 886.31(C$_{66}$H$_{38}$N$_4$ = 887.03) |
| 2-35 | m/z = 886.31(C$_{66}$H$_{38}$N$_4$ = 887.03) | 2-36 | m/z = 860.29(C$_{64}$H$_{36}$N$_4$ = 861.00) |
| 2-37 | m/z = 876.33(C$_{65}$H$_{40}$N$_4$ = 877.04) | 2-38 | m/z = 866.25(C$_{62}$H$_{34}$N$_4$S = 867.03) |
| 2-39 | m/z = 925.32(C$_{68}$H$_{39}$N$_5$ = 926.07) | 2-40 | m/z = 862.31(C$_{64}$H$_{38}$N$_4$ = 863.01) |
| 2-41 | m/z = 862.31(C$_{64}$H$_{38}$N$_4$ = 863.01) | 2-42 | m/z = 791.31(C$_{58}$H$_{29}$D$_5$N$_4$ = 791.95) |
| 2-43 | m/z = 912.33(C$_{68}$H$_{40}$N$_4$ = 913.07) | 2-44 | m/z = 912.33(C$_{68}$H$_{40}$N$_4$ = 913.07) |
| 2-45 | m/z = 912.33(C$_{68}$H$_{40}$N$_4$ = 913.07) | 2-46 | m/z = 912.33(C$_{68}$H$_{40}$N$_4$ = 913.07) |
| 2-47 | m/z = 886.31(C$_{66}$H$_{38}$N$_4$ = 632.75) | 2-48 | m/z = 902.34(C$_{67}$H$_{42}$N$_4$ = 903.08) |
| 2-49 | m/z = 711.24(C$_{51}$H$_{29}$N$_5$ = 711.81) | 2-50 | m/z = 761.26(C$_{55}$H$_{31}$N$_5$ = 761.87) |
| 2-51 | m/z = 761.26(C$_{55}$H$_{31}$N$_5$ = 761.87) | 2-52 | m/z = 787.27(C$_{57}$H$_{33}$N$_5$ = 787.91) |
| 3-1 | m/z = 651.18(C$_{46}$H$_{25}$N$_3$S = 651.78) | 3-2 | m/z = 701.19(C$_{50}$H$_{27}$N$_3$S = 701.83) |
| 3-3 | m/z = 701.19(C$_{50}$H$_{27}$N$_3$S = 701.83) | 3-4 | m/z = 727.21(C$_{52}$H$_{29}$N$_3$S = 727.87) |
| 3-5 | m/z = 727.21(C$_{52}$H$_{29}$N$_3$S = 727.87) | 3-6 | m/z = 656.21(C$_{46}$H$_{20}$D$_5$N$_3$S = 656.81) |
| 3-7 | m/z = 777.22(C$_{56}$H$_{31}$N$_3$S = 777.93) | 3-8 | m/z = 777.22(C$_{56}$H$_{31}$N$_3$S = 777.93) |
| 3-9 | m/z = 777.22(C$_{56}$H$_{31}$N$_3$S = 777.93) | 3-10 | m/z = 777.22(C$_{56}$H$_{31}$N$_3$S = 777.93) |
| 3-11 | m/z = 751.21(C$_{54}$H$_{29}$N$_3$S = 751.89) | 3-12 | m/z = 767.24(C$_{55}$H$_{33}$N$_3$S = 767.94) |
| 3-13 | m/z = 757.16(C$_{52}$H$_{27}$N$_3$S$_2$ = 757.92) | 3-14 | m/z = 816.23(C$_{58}$H$_{32}$N$_4$S = 816.97) |
| 3-15 | m/z = 740.20(C$_{52}$H$_{28}$N$_4$S = 740.87) | 3-16 | m/z = 866.25(C$_{62}$H$_{34}$N$_4$S = 867.03) |
| 4-1 | m/z = 635.20(C$_{46}$H$_{25}$N$_3$O = 635.71) | 4-2 | m/z = 685.22(C$_{50}$H$_{27}$N$_3$O = 685.77) |
| 4-3 | m/z = 685.22(C$_{50}$H$_{27}$N$_3$O = 685.77) | 4-4 | m/z = 711.23(C$_{52}$H$_{29}$N$_3$O = 711.81) |
| 4-5 | m/z = 711.23(C$_{52}$H$_{29}$N$_3$O = 711.81) | 4-6 | m/z = 640.23(C$_{46}$H$_{20}$D$_5$N$_3$O = 640.74) |
| 4-7 | m/z = 761.25(C$_{56}$H$_{31}$N$_3$O = 761.86) | 4-8 | m/z = 761.25(C$_{56}$H$_{31}$N$_3$O = 761.86) |
| 4-9 | m/z = 761.25(C$_{56}$H$_{31}$N$_3$O = 761.86) | 4-10 | m/z = 761.25(C$_{56}$H$_{31}$N$_3$O = 761.86) |
| 4-11 | m/z = 735.23(C$_{54}$H$_{29}$N$_3$S = 735.83) | 4-12 | m/z = 751.26(C$_{55}$H$_{33}$N$_3$O = 751.87) |
| 4-13 | m/z = 741.19(C$_{52}$H$_{27}$N$_3$OS = 741.86) | 4-14 | m/z = 800.26(C$_{58}$H$_{32}$N$_4$O = 800.90) |
| 4-15 | m/z = 724.23(C$_{52}$H$_{28}$N$_4$O = 724.80) | 4-16 | m/z = 850.27(C$_{62}$H$_{34}$N$_4$O = 850.96) |
| 5-1 | m/z = 661.25(C$_{49}$H$_{31}$N$_3$ = 661.79) | 5-2 | m/z = 711.27(C$_{53}$H$_{33}$N$_3$ = 711.85) |
| 5-3 | m/z = 711.27(C$_{53}$H$_{33}$N$_3$ = 711.85) | 5-4 | m/z = 737.28(C$_{55}$H$_{35}$N$_3$ = 737.89) |
| 5-5 | m/z = 737.28(C$_{55}$H$_{35}$N$_3$ = 737.89) | 5-6 | m/z = 666.28(C$_{49}$H$_{26}$D$_5$N$_3$ = 666.82) |
| 5-7 | m/z = 787.30(C$_{59}$H$_{37}$N$_3$ = 787.95) | 5-8 | m/z = 787.30(C$_{59}$H$_{37}$N$_3$ = 787.95) |
| 5-9 | m/z = 787.30(C$_{59}$H$_{37}$N$_3$ = 787.95) | 5-10 | m/z = 787.30(C$_{59}$H$_{37}$N$_3$ = 787.95) |
| 5-11 | m/z = 761.28(C$_{57}$H$_{35}$N$_3$ = 761.91) | 5-12 | m/z = 777.31(C$_{58}$H$_{39}$N$_3$ = 777.95) |
| 5-13 | m/z = 891.27(C$_{65}$H$_{37}$N$_3$S = 892.07) | 5-14 | m/z = 948.33(C$_{71}$H$_{40}$N$_4$ = 949.10) |
| 5-15 | m/z = 767.24(C$_{55}$H$_{33}$N$_3$S = 767.94) | 5-16 | m/z = 826.31(C$_{61}$H$_{38}$N$_4$ = 826.98) |

Fabrication and Evaluation of Organic Electronic Element

[Test Example 1] Green Organic Light Emitting Diode (Phosphorescence Host)

Organic electron emitting diode was manufactured according to a conventional method by using a synthetic compound of the present invention as alight emitting host material of a light emitting layer. First, an ITO layer (anode) was formed on a glass substrate, and a film of $N^1$-(naphthalen-2-yl)-$N^4$,$N^4$-bis(4-(naphthalen-2-yl(phenyl)amino)ph enyl)-$N^1$-phenylbenzene-1,4-diamine (hereinafter abbreviated as "2-TNATA") was vacuum-deposited on the ITO layer to form a hole injection layer with a thickness of 60 nm. Subsequently, 4,4-Bis[N-(1-naphthyl)-N-phenylamino] biphenyl (hereinafter abbreviated as "NPD" was vacuum-deposited on the hole injection layer to forma hole transfer layer with a thickness of 60 nm. And, a emitting layer with a thickness of 30 nm was deposited on the hole transfer layer by doping the hole transfer layer with the compound 1-1 as a host material and Ir(ppy)3 [tris(2-phenylpyridine)-iridium] as a dopant material in a weight ration of 95:5. Next, a film of ((1,1'-bisphenyl)-4-olato)bis(2-methyl-8-quinolinolato) aluminum (hereinafter abbreviated as "BAlq") was vacuum-deposited with a thickness of 10 nm on the light emitting layer to form a hole blocking layer, a film of tris(8-quinolinolato)aluminum (hereinafter abbreviated as "$Alq_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Test Example 2] to [Test Example 36] Green Organic Light Emitting Diode (Phosphorescence Host)

Organic electron emitting diode was manufactured in the same manner as described in Test Example 1, except that any one of the compounds 1-2 to 1-36 of the present invention in the Table 4 below was used as the light emitting host material, instead of the inventive compound 1-1.

Comparative Example 1

Organic electron emitting diode was manufactured in the same manner as described in Test Example 1, except that Comparative Compound 1 represented below was used as the light emitting host material, instead of the inventive compound 1-1.

<Comparative Compound 1>

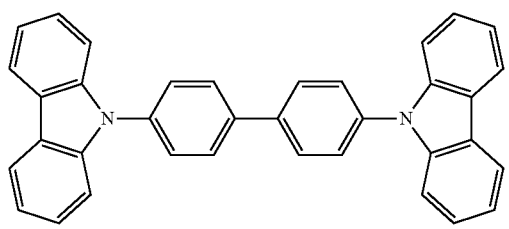 [SMILES: c1ccc2c(c1)c1ccccc1n2-c1ccc(-c2ccc(-n3c4ccccc4c4ccccc43)cc2)cc1]

Comparative Example 2

Organic electron emitting diode was manufactured in the same manner as described in Test Example 1, except that Comparative Compound 2 represented below was used as the light emitting host material, instead of the inventive compound 1-1.

<Comparative Compound 2>

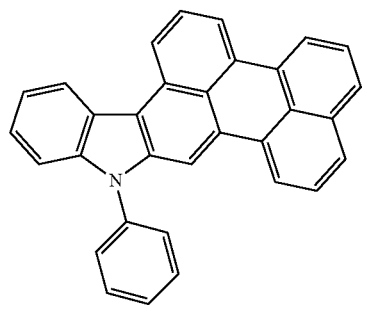 [SMILES: c1ccc(-n2c3ccccc3c3c4cccc5c6cccc7cccc(c(cc32)c54)c76)cc1]

Comparative Example 3

Organic electron emitting diode was manufactured in the same manner as described in Test Example 1, except that Comparative Compound 3 represented below was used as the light emitting host material, instead of the inventive compound 1-1.

<Comparative Compound 3>

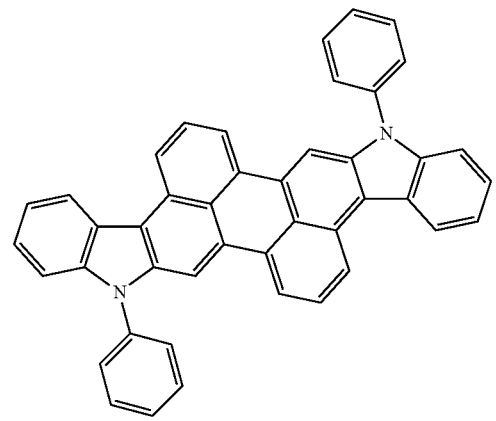 [SMILES: c1ccc(-n2c3ccccc3c3c4cccc5c6cc7c(c8cccc(c(cc32)c54)c68)c2ccccc2n7-c2ccccc2)cc1]

A forward bias DC voltage was applied to each of the OLEDs manufactured through Test Example 1 to 36 and Comparative Example 1 to 3, and electro-luminescence (EL) characteristics of the OLED were measured by PR-650 (Photoresearch). Also, T90 life span was measured by life span measuring equipment (Mcscience) at a reference brightness of 300 cd/m². Table 4 below shows evaluation results of OLEDs manufactured Test Examples and Comparative Examples.

TABLE 4

|  | Compound | Voltage (V) | Current Density (mA/cm²) | Brightness (cd/m²) | Efficiency (cd/A) | Lifetime T (90) | CIE (x, y) |
| --- | --- | --- | --- | --- | --- | --- | --- |
| com. Ex (1) | Com. Com 1 | 6.4 | 9.7 | 300.0 | 3.1 | 68.4 | (0.33, 0.61) |
| com. Ex (2) | Com. Com 2 | 6.3 | 9.2 | 300.0 | 3.3 | 71.4 | (0.31, 0.60) |
| com. Ex (3) | Com. Com 3 | 6.0 | 7.9 | 300.0 | 3.8 | 77.9 | 0.30, 0.61) |
| Ex. (1) | Com. (1-1) | 5.6 | 5.9 | 300.0 | 5.1 | 137.6 | (0.32, 0.61) |
| Ex. (2) | Com. (1-2) | 5.4 | 6.6 | 300.0 | 4.6 | 115.2 | (0.33, 0.60) |
| Ex. (3) | Com. (1-3) | 5.7 | 6.6 | 300.0 | 4.5 | 137.2 | (0.30, 0.61) |
| Ex. (4) | Com. (1-4) | 5.6 | 6.7 | 300.0 | 4.5 | 129.4 | (0.30 0.61) |
| Ex. (5) | Com. (1-5) | 5.5 | 5.6 | 300.0 | 5.3 | 116.3 | (0.31, 0.60) |
| Ex. (6) | Com. (1-6) | 5.4 | 6.1 | 300.0 | 4.9 | 124.2 | (0.33, 0.61) |
| Ex. (7) | Com. (1-7) | 5.7 | 6.5 | 300.0 | 4.6 | 90.7 | (0.32, 0.60) |
| Ex. (8) | Com. (1-8) | 5.5 | 5.8 | 300.0 | 5.2 | 144.2 | (0.32, 0.61) |
| Ex. (9) | Com. (1-9) | 5.6 | 5.7 | 300.0 | 5.3 | 125.9 | (0.33, 0.60) |
| Ex. (10) | Com. (1-10) | 5.3 | 5.7 | 300.0 | 5.2 | 94.2 | (0.30, 0.60) |
| Ex. (11) | Com. (1-11) | 5.5 | 5.7 | 300.0 | 5.3 | 98.6 | (0.30, 0.61) |
| Ex. (12) | Com. (1-12) | 5.5 | 5.5 | 300.0 | 5.5 | 145.7 | (0.31, 0.61) |
| Ex. (13) | Com. (1-13) | 5.5 | 6.1 | 300.0 | 4.9 | 138.6 | (0.31, 0.61) |
| Ex. (14) | Com. (1-14) | 5.4 | 6.4 | 300.0 | 4.7 | 140.8 | (0.31, 0.60) |
| Ex. (15) | Com. (1-15) | 5.7 | 5.7 | 300.0 | 5.3 | 125.6 | (0.31, 0.61) |
| Ex. (16) | Com. (1-16) | 5.6 | 5.6 | 300.0 | 5.3 | 132.4 | (0.32, 0.61) |
| Ex. (17) | Com. (1-17) | 5.3 | 6.0 | 300.0 | 5.0 | 112.0 | (0.31, 0.61) |
| Ex. (18) | Com. (1-18) | 5.7 | 6.2 | 300.0 | 4.9 | 129.5 | (0.33, 0.60) |
| Ex. (19) | Com. (1-19) | 5.7 | 6.3 | 300.0 | 4.7 | 103.3 | (0.31, 0.60) |
| Ex. (20) | Com. (1-20) | 5.5 | 5.8 | 300.0 | 5.2 | 102.4 | (0.32, 0.61) |
| Ex. (21) | Com. (1-21) | 5.6 | 6.3 | 300.0 | 4.7 | 136.9 | (0.32, 0.61) |
| Ex. (22) | Com. (1-22) | 5.5 | 6.4 | 300.0 | 4.7 | 104.4 | (0.33, 0.60) |
| Ex. (23) | Com. (1-23) | 5.4 | 6.1 | 300.0 | 4.9 | 108.4 | (0.30, 0.61) |
| Ex. (24) | Com. (1-24) | 5.3 | 6.5 | 300.0 | 4.6 | 125.3 | (0.31, 0.61) |
| Ex. (25) | Com. (1-25) | 5.5 | 6.2 | 300.0 | 4.8 | 93.7 | (0.30, 0.60) |
| Ex. (26) | Com. (1-26) | 5.4 | 6.1 | 300.0 | 4.9 | 140.5 | (0.33, 0.61) |
| Ex. (27) | Com. (1-27) | 5.5 | 6.4 | 300.0 | 4.7 | 142.4 | (0.32, 0.61) |
| Ex. (28) | Com. (1-28) | 5.4 | 5.8 | 300.0 | 5.2 | 141.4 | (0.33, 0.61) |
| Ex. (29) | Com. (1-29) | 5.6 | 5.9 | 300.0 | 5.1 | 103.0 | (0.32, 0.61) |
| Ex. (30) | Com. (1-30) | 5.5 | 5.9 | 300.0 | 5.1 | 137.6 | (0.33, 0.60) |
| Ex. (31) | Com. (1-31) | 5.4 | 6.6 | 300.0 | 4.6 | 115.2 | (0.30, 0.61) |
| Ex. (32) | Com. (1-32) | 5.4 | 6.6 | 300.0 | 4.5 | 137.2 | (0.30 0.61) |
| Ex. (33) | Com. (1-33) | 5.5 | 6.7 | 300.0 | 4.5 | 129.4 | (0.31, 0.60) |
| Ex. (34) | Com. (1-34) | 5.4 | 5.6 | 300.0 | 5.3 | 116.3 | (0.33, 0.61) |
| Ex. (35) | Com. (1-35) | 5.4 | 6.1 | 300.0 | 4.9 | 124.2 | (0.32, 0.60) |
| Ex. (36) | Com. (1-36) | 5.3 | 6.5 | 300.0 | 4.6 | 90.7 | (0.32, 0.61) |

As can be seen from the results of Table 4, when the materials of the organic electron emitting diode of the present invention is used as a material of a green light emitting layer, the driving voltage could be reduced, and light emitting efficiency, and lifespan could be improved.

The type of perylene core, Comparative compound 2 and 3, shows good results than Comparative Compound 1 of CPB, and Comparative compound 3 fused hetero rings both of the perylene core has good result than comparative compound 2 mono fused hetero ring as demonstrated by comparison between Comparative compound 2 and comparative compound 3. The reason can be predicted that LUMO value of both fused heterocycles is reduced than mono fused heterocycle, But the reduced energy value of perylene may get a energy balance with closer layer as suitable LUMO value and increase energy effiency.

Comparing the result between comparative compound 3 and organic electronic element using the compound of the present invention, the compound of the present invention fused the position of 2, 3, 10, 11 of phenylene group could be observed, has high effiency, a longer life span and a low driving voltage than comparative compound 3 fused the position of 2, 3, 8, 9. This can be explained because the planarity of the compound of the present invention is excellent than comparative compounds, it is improved packing density and mobility when consisted organic electronic element for can be operated the element as a low voltage. By the reason, a damage by thermal is reduced and effiency and life span could be improved.

The compound of the present invention which is fused the position of 2, 3, 10, 11 is relatively shorten a length of conjugation than Comparative compound 3 fused the position of 2, 3, 8, 9 and has wide energy band gap and high T1. This reason can be explained that the hole and electron are smoothly transferred to the light emitting layer and as a result, an exciton is produced easily and improved the efficiency.

[Test Example 37] Red Organic Light Emitting Diode (Phosphorescence Host)

Organic electron emitting diode was manufactured according to a conventional method by using a synthetic compound of the present invention as a organic electron emitting diode material of a light emitting layer. First, an ITO layer (anode) was formed on a glass substrate, and a film of 2-TNATA was vacuum-deposited on the ITO layer to forma hole injection layer with a thickness of 60 nm. Subsequently, NPD was vacuum-deposited on the hole injection layer to form a hole transfer layer with a thickness of 60 nm. Continually, a light emitting layer with a thickness of 30 nm was deposited on the hole transfer layer by doping the hole transfer layer with the compound 2-1 as a host material and (piq)$_2$Ir(acac) [bis-(1-phenylisoquinolyl) iridium(III)acetylacetonate] as a dopant material in a weight ration of 95:5. Next, BAlq was vacuum-deposited with a thickness of 10 nm on the light emitting layer to form a hole blocking layer, a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, Organic electron emitting diode was completed.

[Test Example 38] to [Test Example 136] Red Organic Light Emitting Diode(Phosphorescence Host)

Organic electron emitting diode was manufactured in the manner as described in Test Example 37, except that the compound 2-2 to 2-52, 3-1 to 3-16, 4-1 to 4-16 and 5-1 to 5-16 in the table 5 below was used as a Phosphorescence Host material, instead of the compound 2-1 of the present invention.

Comparative Example 4

Organic electron emitting diode was manufactured in the manner as described in Test Example 37, except that the Comparative compound 1 was used as a Phosphorescence Host material, instead of the compound 2-1 of the present invention.

Comparative Example 5

Organic electron emitting diode was manufactured in the manner as described in Test Example 37, except that the Comparative compound 2 was used as a Phosphorescence Host material, instead of the compound 2-1 of the present invention.

Comparative Example 6

Organic electron emitting diode was manufactured in the manner as described in Test Example 37, except that the Comparative compound 3 was used as a Phosphorescence Host material, instead of the compound 2-1 of the present invention.

A forward bias DC voltage was applied to each of Organic electron emitting diode manufactured through Test Example 37 to 136 and Comparative Example 4 to 6, and electroluminescence (EL) characteristics of the OLED were measured by PR-650 (Photoresearch). Also, T90 life span was measured by life span measuring equipment (Mcscience) at a reference brightness of 300 cd/m$^2$. Table 5 below shows evaluation results of OLEDs manufactured Test Examples and Comparative Examples.

TABLE 5

|  | Compound | Voltage (V) | Current Density (mA/cm$^2$) | Brightness (cd/m$^2$) | Efficiency (cd/A) | Lifetime T (90) | CIE (x, y) |
| --- | --- | --- | --- | --- | --- | --- | --- |
| Com. Ex (4) | Com. Com 1 | 6.5 | 6.5 | 300.0 | 4.6 | 54.2 | (0.66, 0.32) |
| Com. Ex (5) | Com. Com 2 | 6.1 | 6.0 | 300.0 | 5.0 | 60.4 | (0.67, 0.32) |
| Com. Ex (6) | Com. Com 3 | 5.8 | 5.5 | 300.0 | 5.4 | 65.2 | (0.66, 0.32) |
| Ex. (37) | Com. (2-1) | 4.8 | 4.3 | 300.0 | 6.9 | 101.7 | (0.65, 0.32) |
| Ex. (38) | Com. (2-2) | 4.7 | 4.1 | 300.0 | 7.3 | 93.1 | (0.66, 0.32) |
| Ex. (39) | Com. (2-3) | 4.8 | 4.1 | 300.0 | 7.3 | 139.7 | (0.66, 0.33) |
| Ex. (40) | Com. (2-4) | 4.7 | 4.1 | 300.0 | 7.3 | 144.3 | (0.66, 0.32) |
| Ex. (41) | Com. (2-5) | 4.7 | 4.3 | 300.0 | 7.1 | 143.0 | (0.65, 0.32) |
| Ex. (42) | Com. (2-6) | 4.6 | 4.3 | 300.0 | 7.0 | 112.2 | (0.66, 0.32) |
| Ex. (43) | Com. (2-7) | 4.5 | 4.3 | 300.0 | 7.0 | 133.4 | (0.66, 0.32) |
| Ex. (44) | Com. (2-8) | 4.7 | 4.3 | 300.0 | 6.9 | 121.1 | (0.67, 0.32) |
| Ex. (45) | Com. (2-9) | 4.7 | 4.3 | 300.0 | 7.0 | 104.2 | (0.66, 0.32) |
| Ex. (46) | Com. (2-10) | 4.5 | 4.1 | 300.0 | 7.4 | 138.7 | (0.66, 0.33) |
| Ex. (47) | Com. (2-11) | 4.5 | 4.2 | 300.0 | 7.1 | 98.7 | (0.66, 0.32) |
| Ex. (48) | Com. (2-12) | 4.6 | 4.1 | 300.0 | 7.3 | 98.4 | (0.65, 0.32) |
| Ex. (49) | Com. (2-13) | 4.7 | 4.3 | 300.0 | 7.0 | 112.1 | (0.66, 0.32) |
| Ex. (50) | Com. (2-14) | 4.6 | 4.3 | 300.0 | 6.9 | 101.4 | (0.66, 0.33) |
| Ex. (51) | Com. (2-15) | 4.8 | 4.0 | 300.0 | 7.5 | 149.9 | (0.66, 0.32) |
| Ex. (52) | Com. (2-16) | 4.8 | 4.2 | 300.0 | 7.2 | 139.7 | (0.65, 0.32) |
| Ex. (53) | Com. (2-17) | 4.6 | 4.1 | 300.0 | 7.3 | 146.9 | (0.66, 0.32) |
| Ex. (54) | Com. (2-18) | 4.6 | 4.3 | 300.0 | 7.0 | 127.1 | (0.66, 0.32) |
| Ex. (55) | Com. (2-19) | 4.6 | 4.0 | 300.0 | 7.5 | 142.1 | (0.66, 0.32) |
| Ex. (56) | Com. (2-20) | 4.7 | 4.2 | 300.0 | 7.1 | 141.8 | (0.67, 0.32) |
| Ex. (57) | Com. (2-21) | 4.5 | 4.0 | 300.0 | 7.4 | 96.3 | (0.66, 0.32) |
| Ex. (58) | Com. (2-22) | 4.6 | 4.0 | 300.0 | 7.4 | 117.6 | (0.66, 0.33) |
| Ex. (59) | Com. (2-23) | 4.7 | 4.1 | 300.0 | 7.2 | 124.8 | (0.66, 0.32) |
| Ex. (60) | Com. (2-24) | 4.5 | 4.1 | 300.0 | 7.3 | 116.9 | (0.65, 0.32) |
| Ex. (61) | Com. (2-25) | 4.7 | 4.2 | 300.0 | 7.2 | 101.4 | (0.66, 0.32) |
| Ex. (62) | Com. (2-26) | 4.5 | 4.3 | 300.0 | 7.0 | 99.8 | (0.66, 0.33) |
| Ex. (63) | Com. (2-27) | 4.7 | 4.3 | 300.0 | 6.9 | 126.9 | (0.66, 0.32) |
| Ex. (64) | Com. (2-28) | 4.8 | 4.1 | 300.0 | 7.3 | 115.2 | (0.65, 0.32) |
| Ex. (65) | Com. (2-29) | 4.7 | 4.2 | 300.0 | 7.1 | 129.8 | (0.66, 0.32) |
| Ex. (66) | Com. (2-30) | 4.7 | 4.0 | 300.0 | 7.4 | 118.8 | (0.66, 0.32) |
| Ex. (67) | Com. (2-31) | 4.5 | 4.1 | 300.0 | 7.3 | 101.7 | (0.67, 0.32) |
| Ex. (68) | Com. (2-32) | 4.8 | 4.2 | 300.0 | 7.2 | 98.7 | (0.66, 0.32) |
| Ex. (69) | Com. (2-33) | 4.6 | 4.3 | 300.0 | 7.0 | 94.9 | (0.66, 0.33) |
| Ex. (70) | Com. (2-34) | 4.5 | 4.0 | 300.0 | 7.4 | 112.9 | (0.66, 0.32) |
| Ex. (71) | Com. (2-35) | 4.7 | 4.1 | 300.0 | 7.3 | 118.7 | (0.65, 0.32) |
| Ex. (72) | Com. (2-36) | 4.5 | 4.2 | 300.0 | 7.1 | 94.3 | (0.66, 0.32) |

TABLE 5-continued

| | Compound | Voltage (V) | Current Density (mA/cm$^2$) | Brightness (cd/m$^2$) | Efficiency (cd/A) | Lifetime T (90) | CIE (x, y) |
|---|---|---|---|---|---|---|---|
| Ex. (73) | Com. (2-37) | 4.7 | 4.2 | 300.0 | 7.2 | 94.2 | (0.66, 0.33) |
| Ex. (74) | Com. (2-38) | 4.7 | 4.1 | 300.0 | 7.3 | 128.0 | (0.66, 0.32) |
| Ex. (75) | Com. (2-39) | 4.7 | 4.1 | 300.0 | 7.2 | 136.6 | (0.65, 0.32) |
| Ex. (76) | Com. (2-40) | 4.8 | 4.3 | 300.0 | 7.0 | 95.6 | (0.66, 0.32) |
| Ex. (77) | Com. (2-41) | 4.6 | 4.0 | 300.0 | 7.5 | 149.2 | (0.66, 0.32) |
| Ex. (78) | Com. (2-42) | 4.7 | 4.1 | 300.0 | 7.3 | 101.7 | (0.66, 0.32) |
| Ex. (79) | Com. (2-43) | 4.6 | 4.2 | 300.0 | 7.2 | 103.0 | (0.67, 0.32) |
| Ex. (80) | Com. (2-44) | 4.8 | 4.2 | 300.0 | 7.1 | 118.0 | (0.66, 0.32) |
| Ex. (81) | Com. (2-45) | 4.8 | 4.2 | 300.0 | 7.1 | 120.5 | (0.66, 0.33) |
| Ex. (82) | Com. (2-46) | 4.6 | 4.1 | 300.0 | 7.2 | 111.9 | (0.66, 0.32) |
| Ex. (83) | Com. (2-47) | 4.5 | 4.2 | 300.0 | 7.1 | 123.7 | (0.65, 0.32) |
| Ex. (84) | Com. (2-48) | 4.7 | 4.1 | 300.0 | 7.3 | 140.2 | (0.66, 0.32) |
| Ex. (85) | Com. (2-49) | 4.6 | 4.0 | 300.0 | 7.4 | 102.8 | (0.66, 0.33) |
| Ex. (86) | Com. (2-50) | 4.7 | 4.3 | 300.0 | 7.0 | 126.0 | (0.66, 0.32) |
| Ex. (87) | Com. (2-51) | 4.5 | 4.1 | 300.0 | 7.2 | 120.9 | (0.65, 0.32) |
| Ex. (88) | Com. (2-52) | 4.7 | 4.1 | 300.0 | 7.3 | 95.8 | (0.66, 0.32) |
| Ex. (89) | Com. (3-1) | 4.9 | 4.5 | 300.0 | 6.7 | 127.6 | (0.66, 0.32) |
| Ex. (90) | Com. (3-2) | 4.8 | 4.5 | 300.0 | 6.6 | 115.3 | (0.67, 0.32) |
| Ex. (91) | Com. (3-3) | 4.9 | 4.5 | 300.0 | 6.6 | 115.0 | (0.66, 0.32) |
| Ex. (92) | Com. (3-4) | 5.0 | 4.6 | 300.0 | 6.6 | 148.8 | (0.66, 0.33) |
| Ex. (93) | Com. (3-5) | 4.9 | 4.5 | 300.0 | 6.7 | 104.8 | (0.66, 0.32) |
| Ex. (94) | Com. (3-6) | 4.8 | 4.4 | 300.0 | 6.8 | 132.8 | (0.65, 0.32) |
| Ex. (95) | Com. (3-7) | 4.8 | 4.6 | 300.0 | 6.5 | 112.3 | (0.66, 0.32) |
| Ex. (96) | Com. (3-8) | 4.8 | 4.6 | 300.0 | 6.6 | 98.3 | (0.66, 0.33) |
| Ex. (97) | Com. (3-9) | 4.8 | 4.6 | 300.0 | 6.6 | 134.6 | (0.66, 0.32) |
| Ex. (98) | Com. (3-10) | 4.8 | 4.5 | 300.0 | 6.6 | 116.2 | (0.65, 0.32) |
| Ex. (99) | Com. (3-11) | 4.8 | 4.4 | 300.0 | 6.8 | 142.1 | (0.66, 0.32) |
| Ex. (100) | Com. (3-12) | 4.9 | 4.5 | 300.0 | 6.6 | 124.0 | (0.66, 0.32) |
| Ex. (101) | Com. (3-13) | 4.9 | 4.6 | 300.0 | 6.6 | 100.6 | (0.66, 0.32) |
| Ex. (102) | Com. (3-14) | 4.9 | 4.6 | 300.0 | 6.5 | 95.7 | (0.66, 0.32) |
| Ex. (103) | Com. (3-15) | 4.9 | 4.4 | 300.0 | 6.8 | 94.2 | (0.65, 0.32) |
| Ex. (104) | Com. (3-16) | 4.9 | 4.6 | 300.0 | 6.5 | 149.9 | (0.66, 0.32) |
| Ex. (105) | Com. (4-1) | 5.2 | 4.8 | 300.0 | 6.2 | 110.4 | (0.66, 0.32) |
| Ex. (106) | Com. (4-2) | 5.0 | 4.7 | 300.0 | 6.4 | 140.1 | (0.67, 0.32) |
| Ex. (107) | Com. (4-3) | 5.2 | 4.7 | 300.0 | 6.4 | 107.4 | (0.66, 0.32) |
| Ex. (108) | Com. (4-4) | 5.0 | 4.7 | 300.0 | 6.4 | 104.6 | (0.66, 0.33) |
| Ex. (109) | Com. (4-5) | 5.2 | 4.7 | 300.0 | 6.4 | 135.1 | (0.66, 0.32) |
| Ex. (110) | Com. (4-6) | 5.3 | 4.8 | 300.0 | 6.2 | 112.9 | (0.65, 0.32) |
| Ex. (111) | Com. (4-7) | 5.2 | 4.7 | 300.0 | 6.4 | 140.9 | (0.66, 0.32) |
| Ex. (112) | Com. (4-8) | 5.1 | 4.8 | 300.0 | 6.2 | 128.1 | (0.66, 0.33) |
| Ex. (113) | Com. (4-9) | 5.2 | 4.7 | 300.0 | 6.4 | 108.0 | (0.66, 0.32) |
| Ex. (114) | Com. (4-10) | 5.1 | 4.9 | 300.0 | 6.2 | 139.0 | (0.65, 0.32) |
| Ex. (115) | Com. (4-11) | 5.2 | 4.9 | 300.0 | 6.2 | 125.0 | (0.66, 0.32) |
| Ex. (116) | Com. (4-12) | 5.1 | 4.8 | 300.0 | 6.2 | 144.3 | (0.66, 0.32) |
| Ex. (117) | Com. (4-13) | 5.3 | 4.8 | 300.0 | 6.2 | 129.2 | (0.66, 0.32) |
| Ex. (118) | Com. (4-14) | 5.1 | 4.7 | 300.0 | 6.4 | 127.1 | (0.67, 0.32) |
| Ex. (119) | Com. (4-15) | 5.0 | 4.9 | 300.0 | 6.2 | 99.0 | (0.66, 0.32) |
| Ex. (120) | Com. (4-16) | 5.1 | 4.7 | 300.0 | 6.4 | 135.3 | (0.66, 0.33) |
| Ex. (121) | Com. (5-1) | 5.4 | 5.1 | 300.0 | 5.9 | 145.3 | (0.66, 0.32) |
| Ex. (122) | Com. (5-2) | 5.4 | 5.0 | 300.0 | 6.0 | 113.4 | (0.65, 0.32) |
| Ex. (123) | Com. (5-3) | 5.4 | 4.9 | 300.0 | 6.1 | 146.0 | (0.66, 0.32) |
| Ex. (124) | Com. (5-4) | 5.5 | 4.9 | 300.0 | 6.1 | 137.5 | (0.66, 0.33) |
| Ex. (125) | Com. (5-5) | 5.4 | 5.1 | 300.0 | 5.8 | 136.4 | (0.66, 0.32) |
| Ex. (126) | Com. (5-6) | 5.4 | 5.0 | 300.0 | 6.0 | 131.5 | (0.65, 0.32) |
| Ex. (127) | Com. (5-7) | 5.4 | 5.1 | 300.0 | 5.9 | 103.2 | (0.66, 0.32) |
| Ex. (128) | Com. (5-8) | 5.3 | 5.1 | 300.0 | 5.8 | 129.0 | (0.66, 0.32) |
| Ex. (129) | Com. (5-9) | 5.5 | 5.1 | 300.0 | 5.9 | 135.4 | (0.67, 0.32) |
| Ex. (130) | Com. (5-10) | 5.4 | 5.1 | 300.0 | 5.8 | 140.0 | (0.66, 0.32) |
| Ex. (131) | Com. (5-11) | 5.4 | 5.0 | 300.0 | 6.0 | 116.8 | (0.66, 0.33) |
| Ex. (132) | Com. (5-12) | 5.5 | 5.2 | 300.0 | 5.8 | 98.1 | (0.66, 0.32) |
| Ex. (133) | Com. (5-13) | 5.5 | 5.1 | 300.0 | 5.9 | 92.8 | (0.65, 0.32) |
| Ex. (134) | Com. (5-14) | 5.4 | 5.1 | 300.0 | 5.9 | 106.0 | (0.66, 0.32) |
| Ex. (135) | Com. (5-15) | 5.3 | 5.0 | 300.0 | 6.0 | 133.5 | (0.66, 0.33) |
| Ex. (136) | Com. (5-16) | 5.4 | 5.1 | 300.0 | 5.8 | 108.8 | (0.66, 0.32) |

As can be seen from the results of Table 5, when the materials of the organic electron emitting diode of the present invention is used as a material of a red light emitting layer, the driving voltage could be reduced, and light emitting efficiency, and lifespan could be improved.

The type of perylene core, Comparative compound 2 and 3, shows good results than Comparative Compound 1 of CPB, and Comparative compound 3 fused hetero rings both of the perylene core has good result than comparative compound 2 mono fused hetero ring as demonstrated by comparison between Comparative compound 2 and comparative compound 3. The reason can be predicted that LUMO value of both fused heterocycles is reduced than mono fused heterocycle, But the reduced energy value of perylene may get a energy balance with closer layer as suitable LUMO value and increase energy effieiency.

Comparing the result between comparative compound 3 and organic electronic element using the compound of the present invention, the compound of the present invention fused the position of 2, 3, 10, 11 of phenylene group could be observed has high effiency, a longer life span and a low driving voltage than comparative compound 3 fused the position of 2, 3, 8, 9. This can be explained because the planarity of the compound of the present invention is excellent than comparative compounds, it is improved packing density and mobility when consisted organic electronic element for can be operated the element as a low voltage. By the reason, a damage by thermal is reduced and effiency and life span could be improved.

The compound of the present invention which is fused the position of 2, 3, 10, 11 is relatively shorten a length of conjugation than Comparative compound 3 fused the position of 2, 3, 8, 9 and has wide energy band gap and high T1. This reason can be explained that the hole and electron are smoothly transferred to the light emitting layer and as a result, an exciton is produced easily and improved the efficiency.

It is obvious that even when the inventive compounds are used in other organic material layers of an OLED, for example, an electron injection layer, an electron transport layer, and a hole injection layer, the same effects can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

[Formula 1]

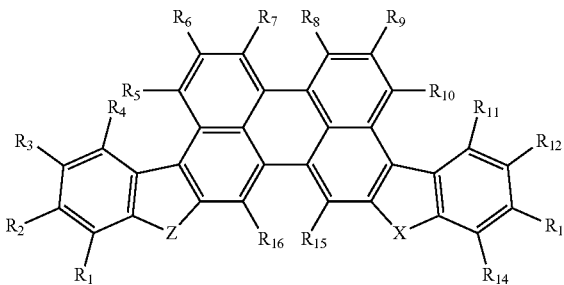

wherein, $R_1$ to $R_{16}$ i) are independently selected from the group consisting of hydrogen, deuterium, halogen, a $C_6$-$C_{60}$ aryl group, a $C_2$-$C_{60}$ heterocyclic group containing at least one heteroatom selected from O, N, S, Si, and P, a $C_1$-$C_{60}$ alkyl group, -L-N(Ar$_1$)(Ar$_2$) and a fluorenyl group, or ii) any adjacent groups of $R_1$ and $R_2$, $R_2$ and $R_3$, $R_3$ and $R_4$, $R_5$ and $R_6$, $R_6$ and $R_7$, $R_8$ and $R_9$, $R_9$ and $R_{10}$, $R_{11}$ and $R_{12}$, $R_{12}$ and $R_{13}$, and $R_{13}$ and $R_{14}$, can be independently linked together to form at least one fused ring, wherein, $R_1$ to $R_{14}$ that don't form a fused ring can be as defined above i), X and Z are the same or different, independently N(Ar), S, O or C(R')(R"), wherein Ar is selected from the group consisting of a $C_6$-$C_{60}$ aryl group, a $C_2$-$C_{60}$ heterocyclic group containing at least one heteroatom selected from O, N, S, Si, and P, a $C_1$-$C_{60}$ alkyl group, a $C_2$-$C_{20}$ alkenyl group, a fluorenyl group, a $C_1$-$C_{30}$ alkoxyl group and -L$_1$-N(Ar$_3$)(Ar$_4$), L and L$_1$ are independently selected from the group consisting of a single bond, $C_6$-$C_{60}$ arylen group, $C_2$-$C_{60}$ heteroarylene group, fluorenylene group, and a divalent aliphatic hydrocarbon group, Ar$_1$ to Ar$_4$ are independently selected from the group consisting of a $C_6$-$C_{60}$ aryl group, a $C_2$-$C_{60}$ heterocyclic group containing at least one heteroatom selected from O, N, S, Si, and P, a $C_1$-$C_{60}$ alkyl group, $C_2$-$C_{60}$ alkenyl group, $C_1$-$C_{30}$ alkoxy group, fluorenylene group, R' and R" are independently selected from the group consisting of a $C_6$-$C_{60}$ aryl group, a fluorenylene group, a $C_2$-$C_{60}$ heterocyclic group containing at least one heteroatom selected from O, N, S, Si, and P, a $C_1$-$C_{50}$ alkyl group, with the provisos that, the aryl group, fluorenyl group, heterocyclic group, alkyl group, alkenyl group, and alkoxy group may be optionally substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group, with the provisos that, the arylene group, heteroarylene group, fluorenyl group and divalent aliphatic hydrocarbon group may be optionally substituted by one or more substituents selected from the group consisting of nitro group, cyano group, halogen, $C_1$-$C_{20}$ alkyl group, $C_6$-$C_{20}$ aryl group, $C_2$-$C_{20}$ heterocyclic group, $C_1$-$C_{20}$ alkoxy group and amino group.

2. The compound as claimed in claim 1, wherein the compound is represented by one of Formulas below:

[Formula 2]

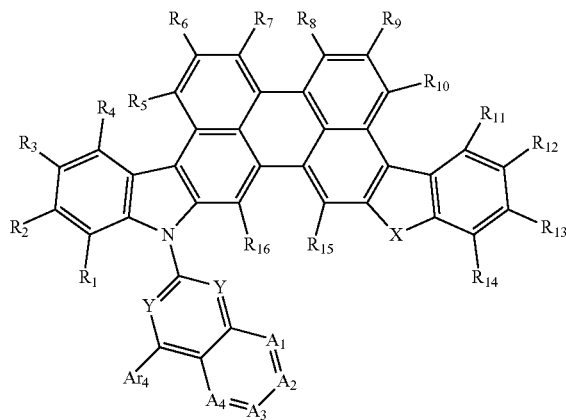

[Formula 3]

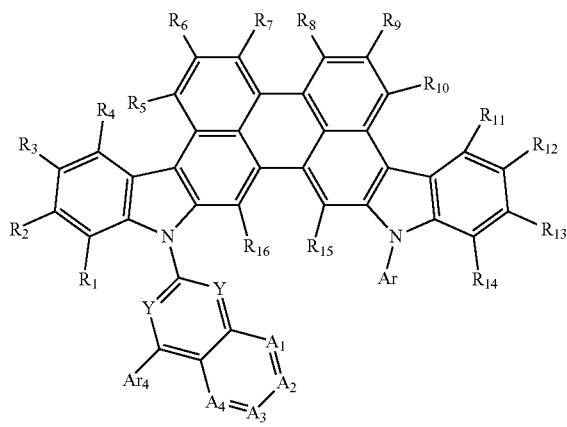

[Formula 4]

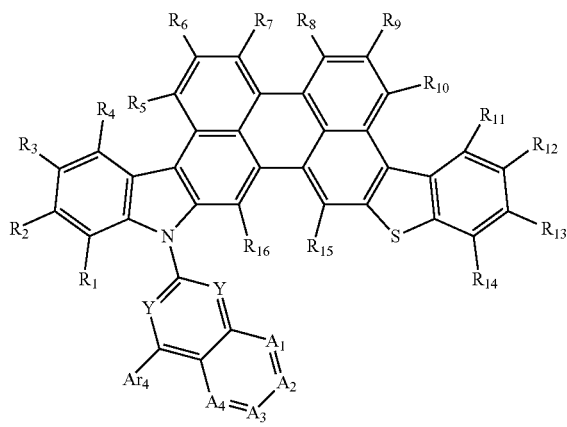

[Formula 5]

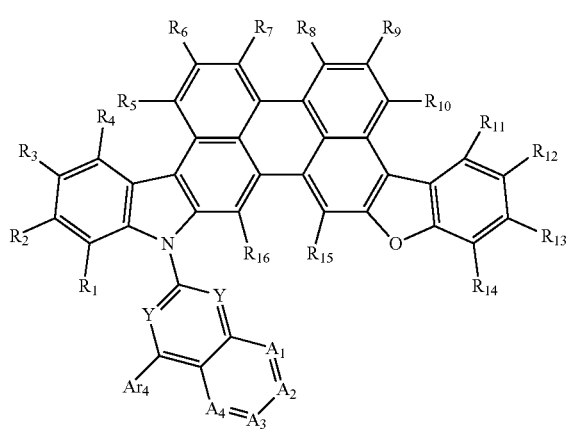

[Formula 6]

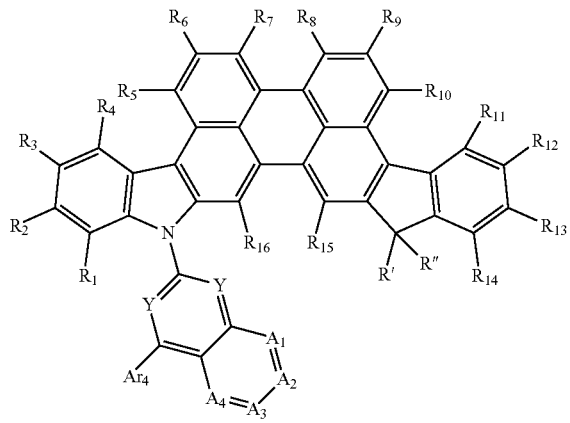

wherein, $R_1$ to $R_{16}$, X, R', R" and Ar are defined as in claim 1,

Y and $A_1$ to $A_4$ are the same or different, independently, N or C($R_{17}$), $R_{17}$ is hydrogen, deuterium, $C_6$-$C_{60}$ aryl group, or $C_2$-$C_{60}$ heterocyclic group consisting at least one heteroatom selected from O, N, S, Si, and P, $Ar_4$ can be selected from the group consisting of $C_6$-$C_{60}$ aryl group, $C_2$-$C_{60}$ heterocyclic group consisting at least one heteroatom selected from O, N, S, Si, and P, $C_1$-$C_{50}$ alkyl group, $C_2$-$C_{20}$ alkenyl group, $C_1$-$C_{30}$ alkoxy group and fluorenyl group.

3. The compound as claimed in claim 1, being any one of the compounds below:

1-1

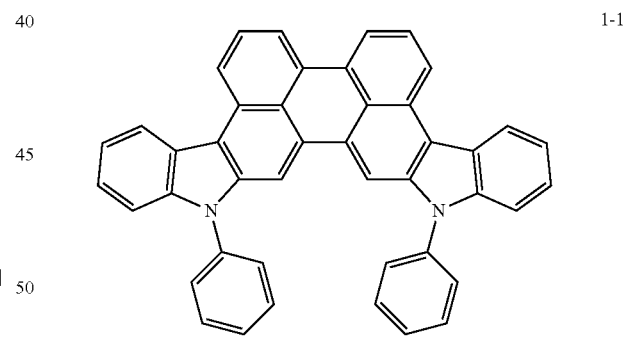

1-2

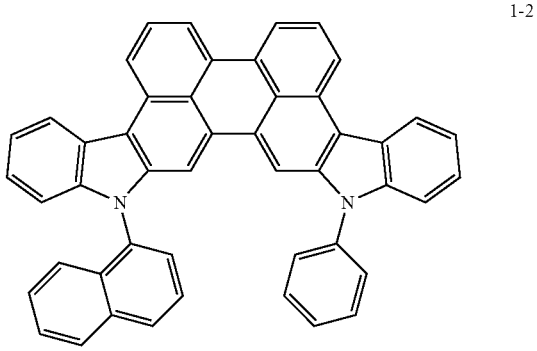

-continued
1-3
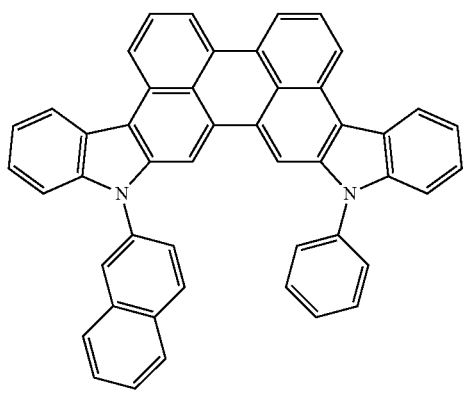
1-4
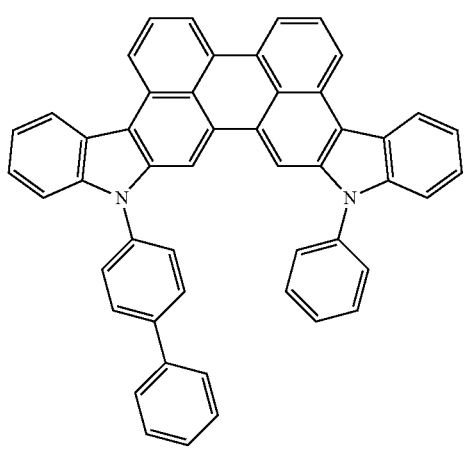
1-5
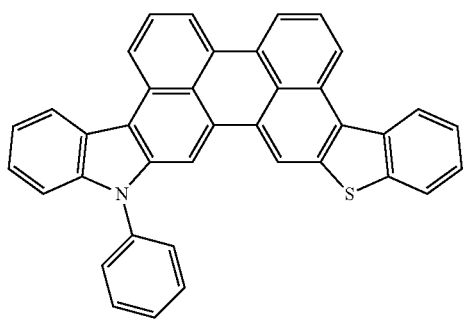
I-6
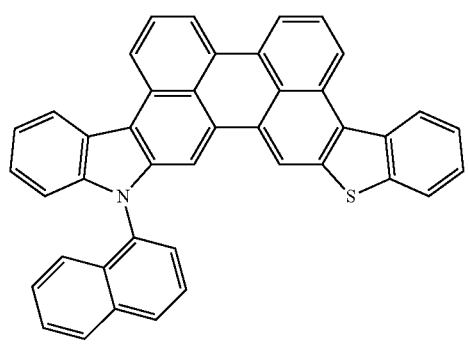
-continued
1-7
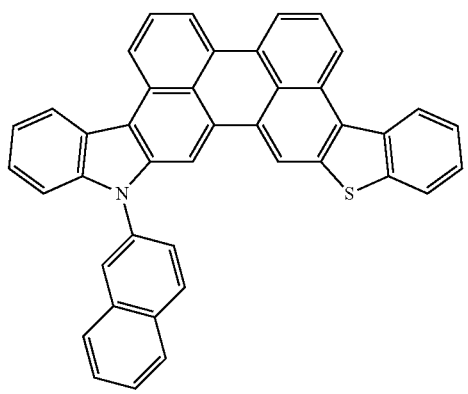
1-8
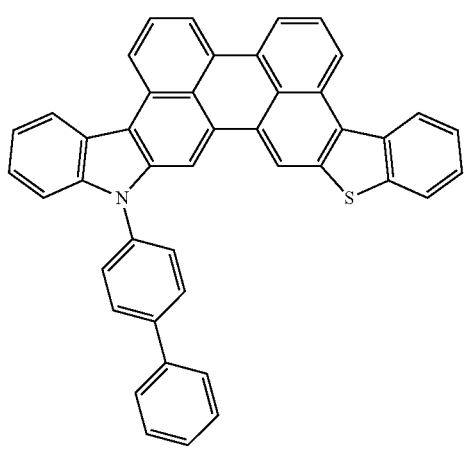
1-9
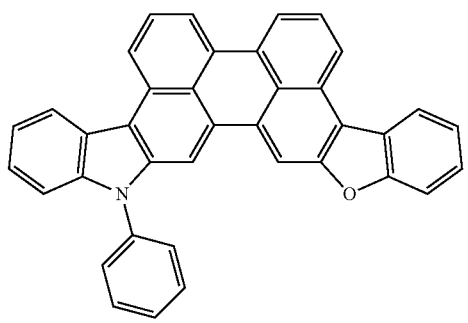
1-10
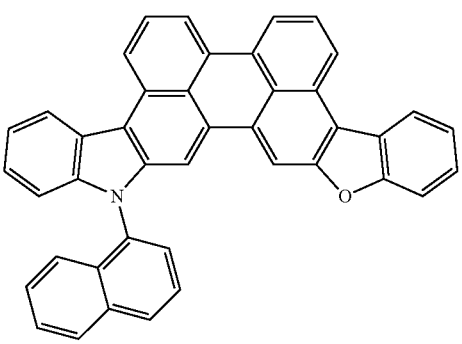

1-11 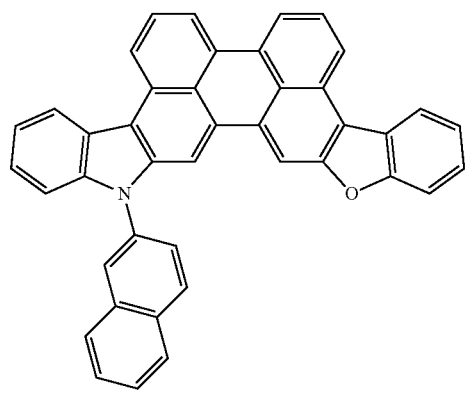
1-12 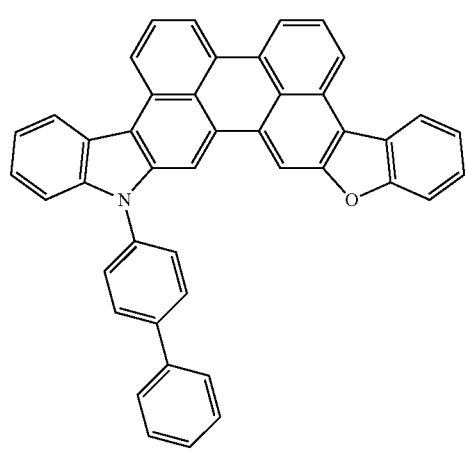
1-13 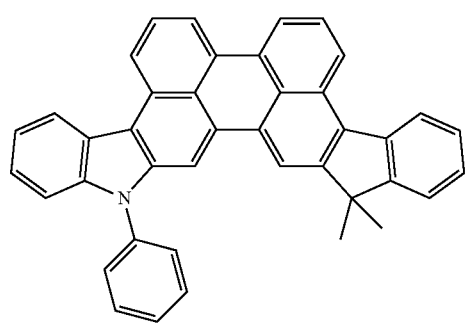
1-14 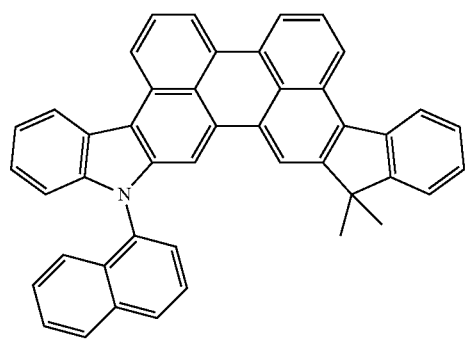
1-15 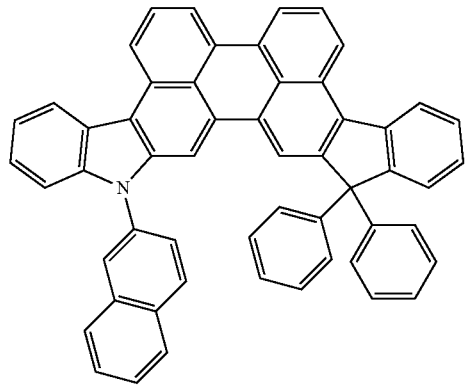
1-16 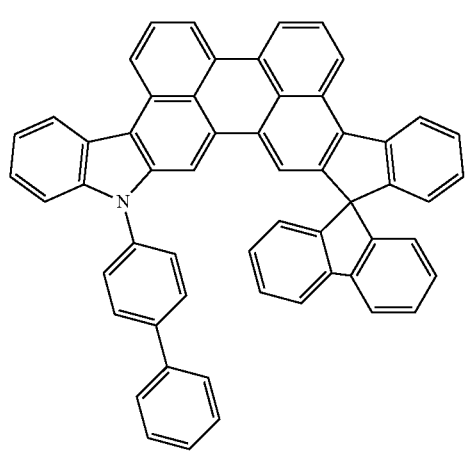
1-17 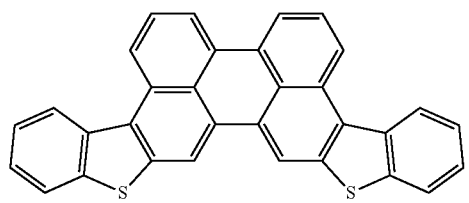
1-18 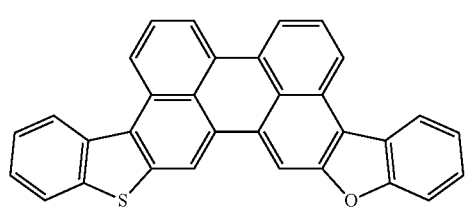
1-19 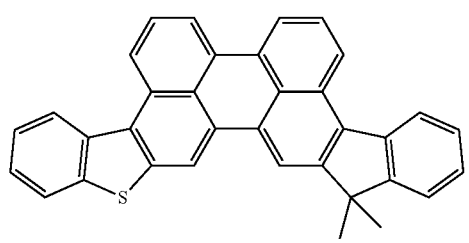

-continued
1-20
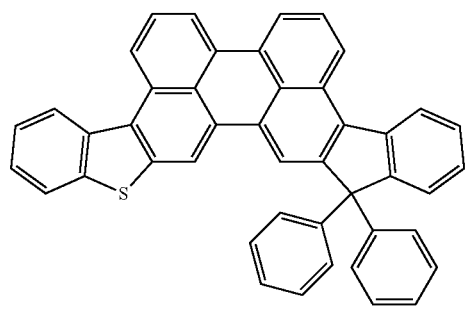
1-21
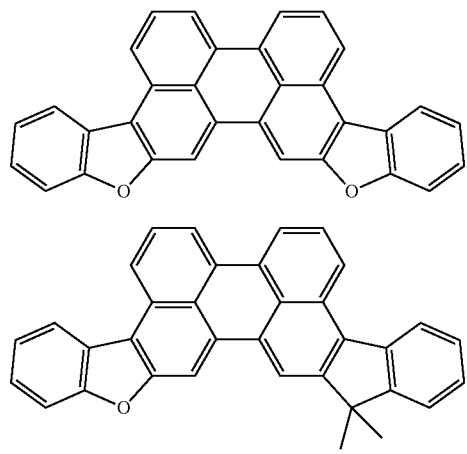
1-22
1-23
1-24
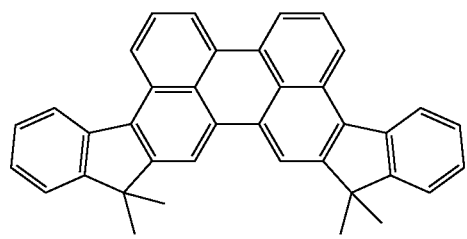
1-25
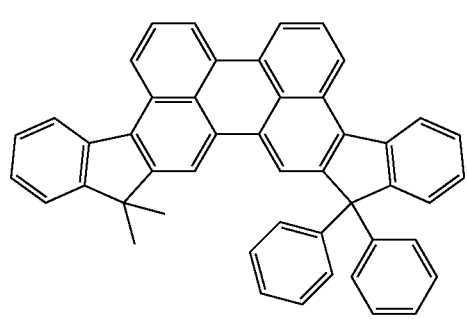
-continued
1-26
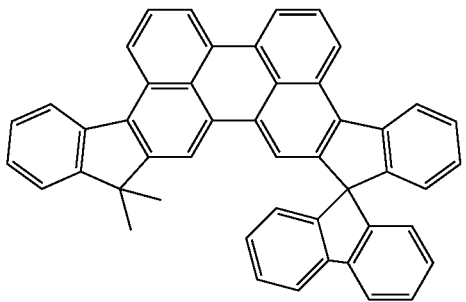
1-27
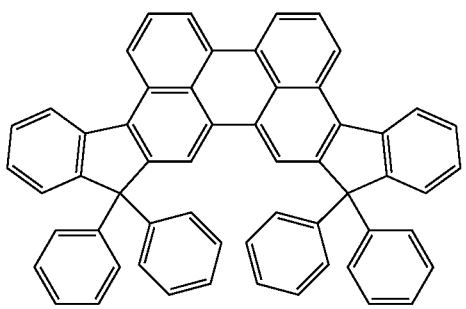
1-28
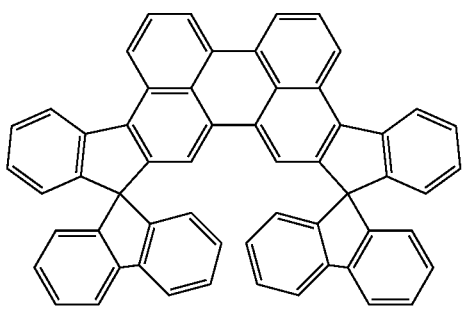
1-29
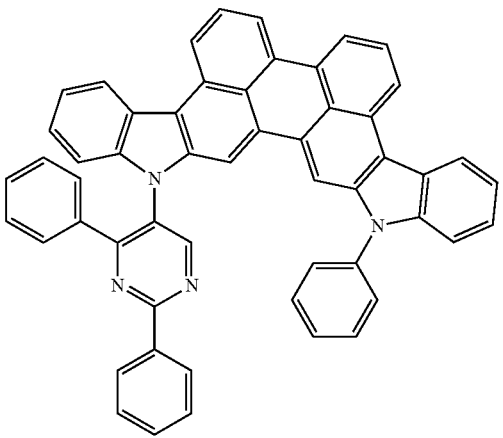

1-30
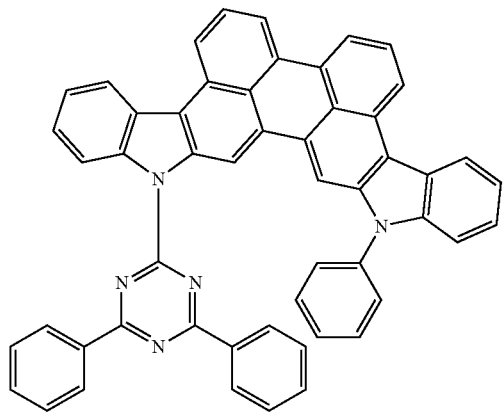
1-31
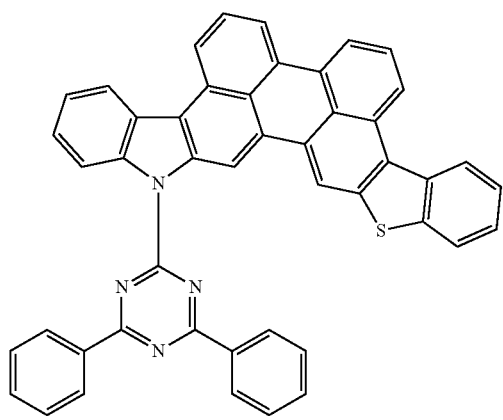
1-32
1-33
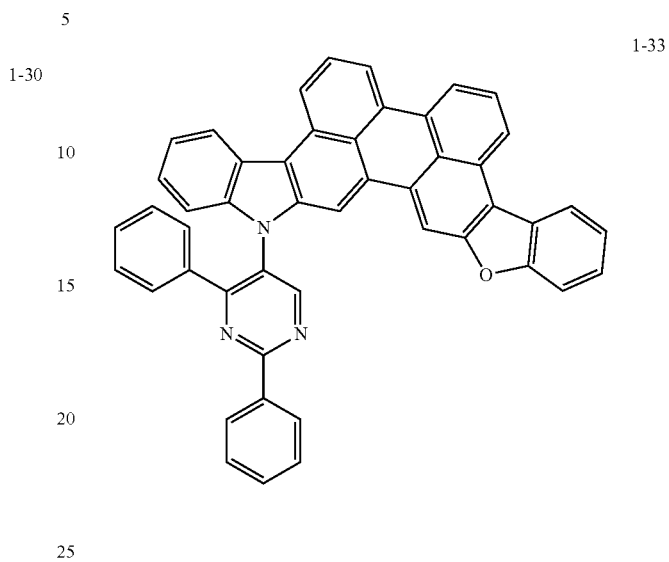
1-34
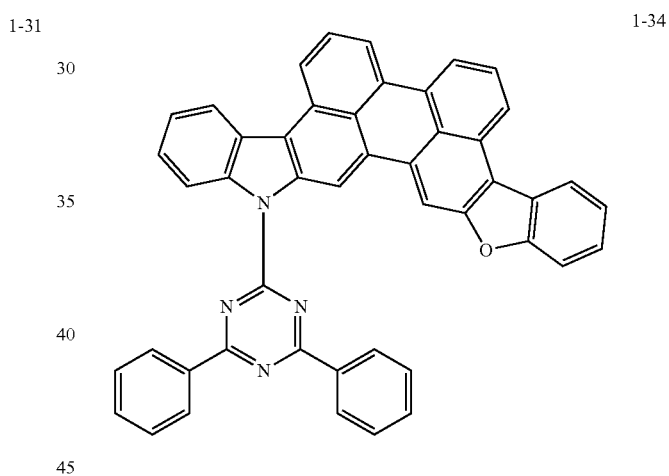
1-35
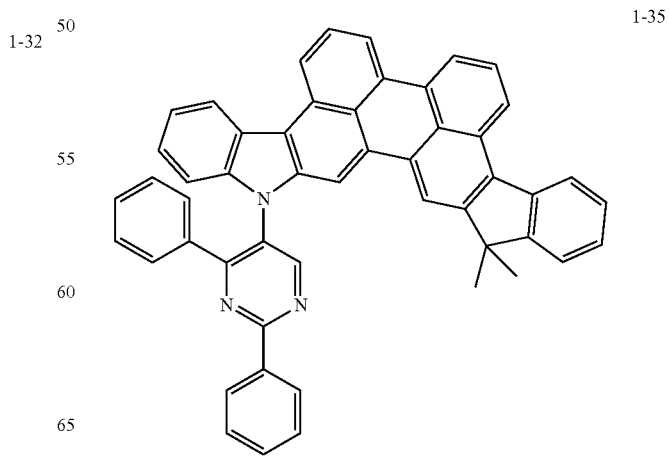

101
-continued
1-36
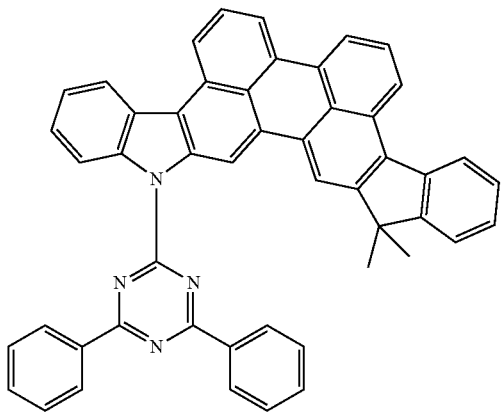
2-1
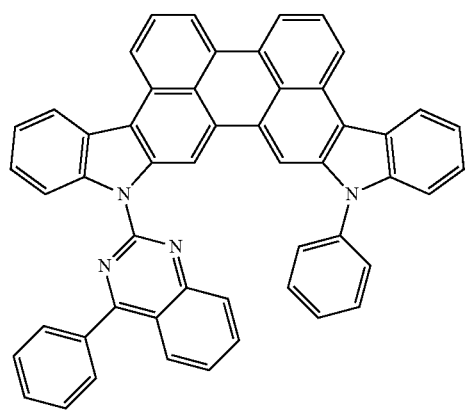
2-2
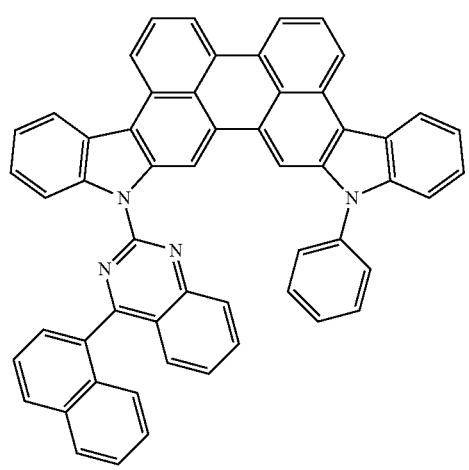
102
-continued
2-3
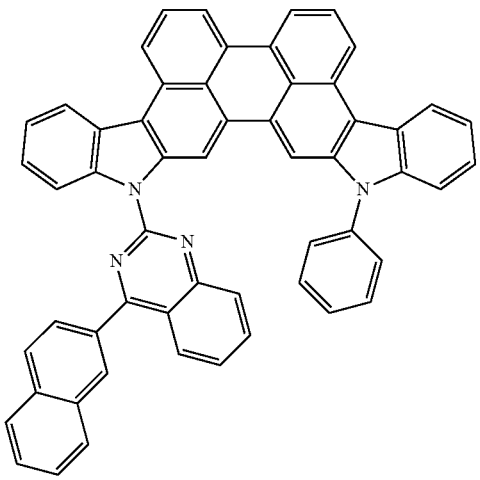
2-4
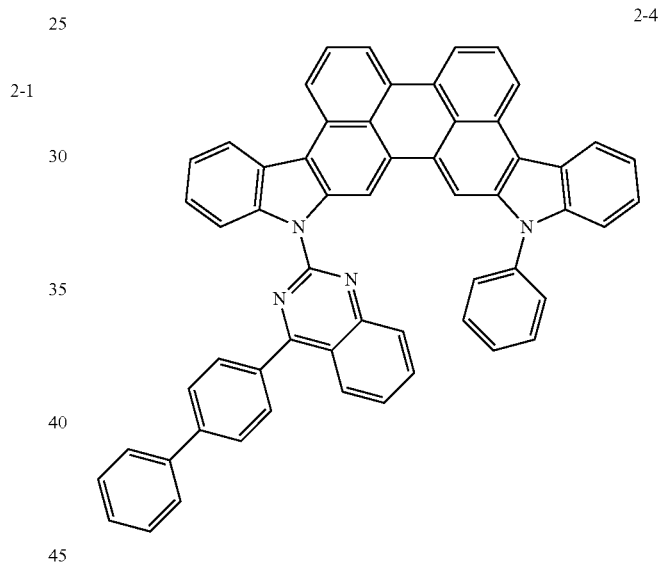
2-5
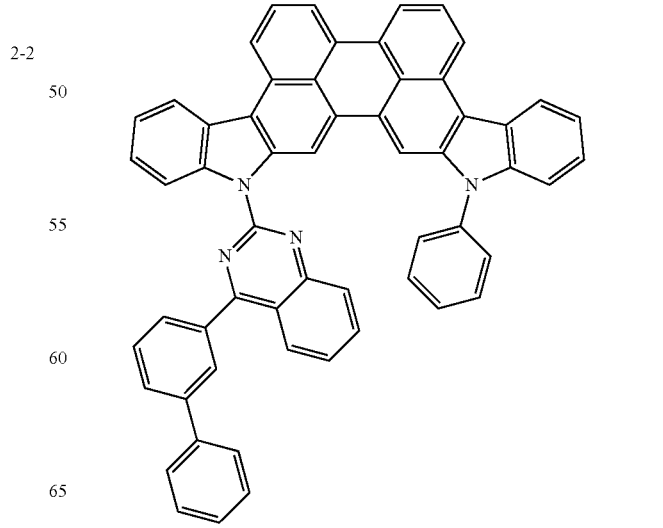

2-6
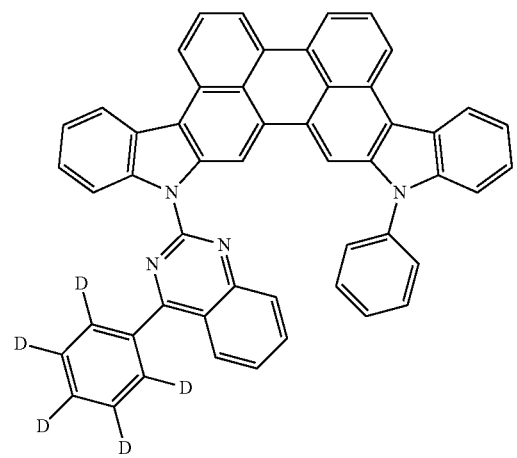
2-7
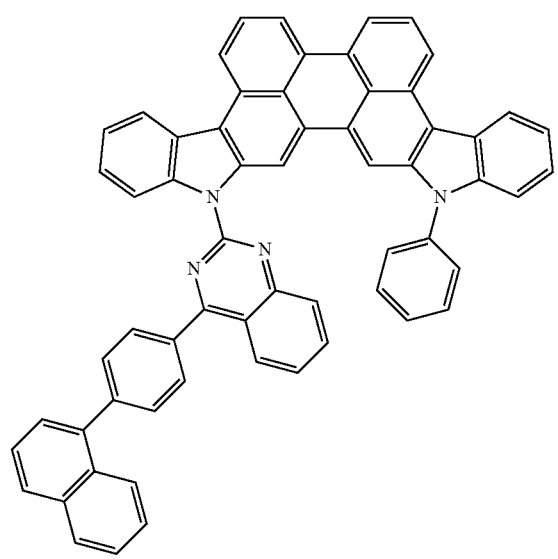
2-8
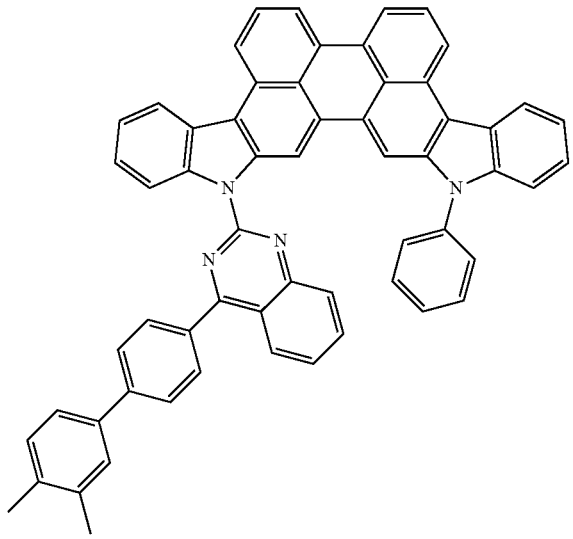
2-9
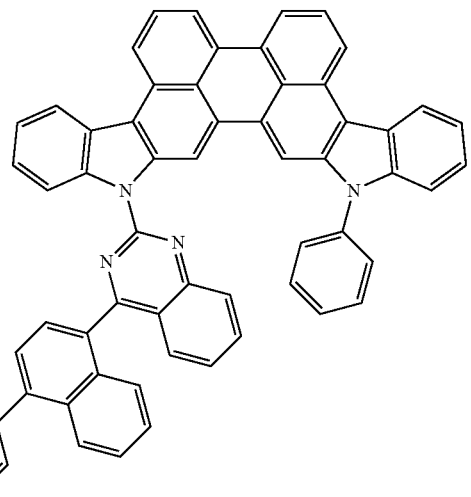
2-10
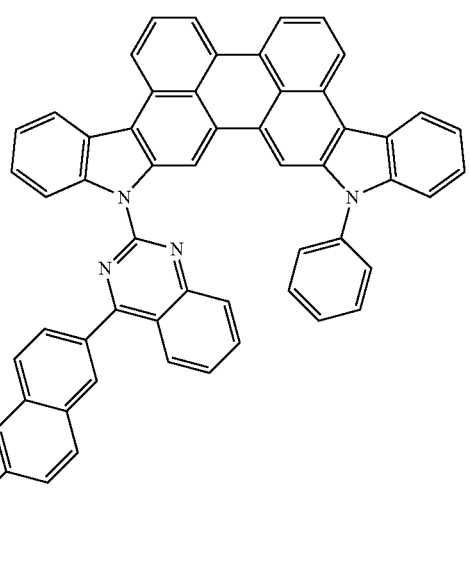
2-11
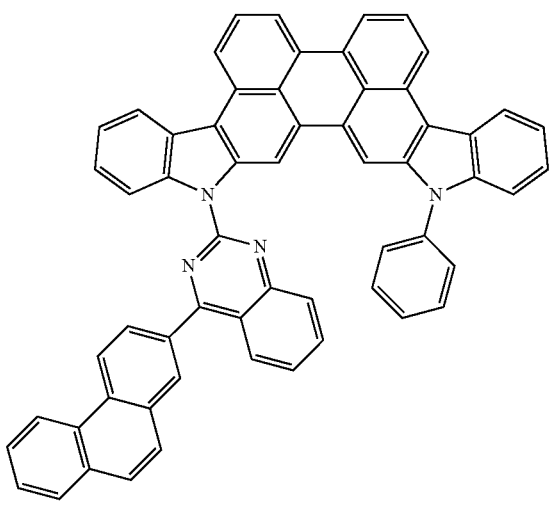

-continued
2-12
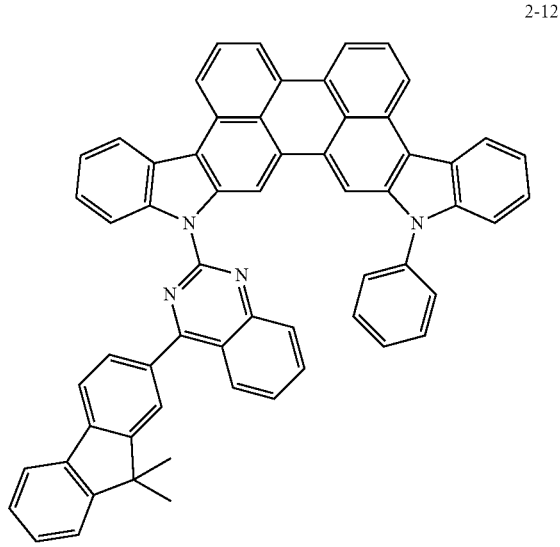
2-13
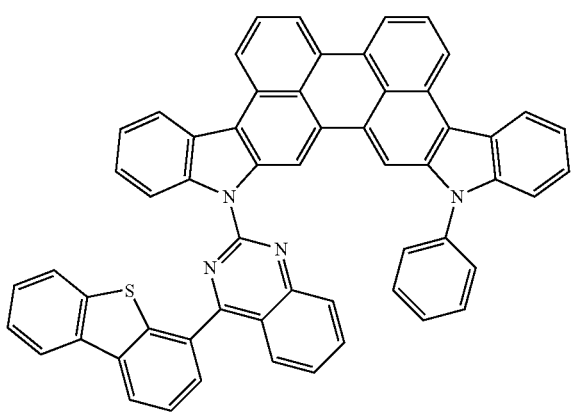
2-14
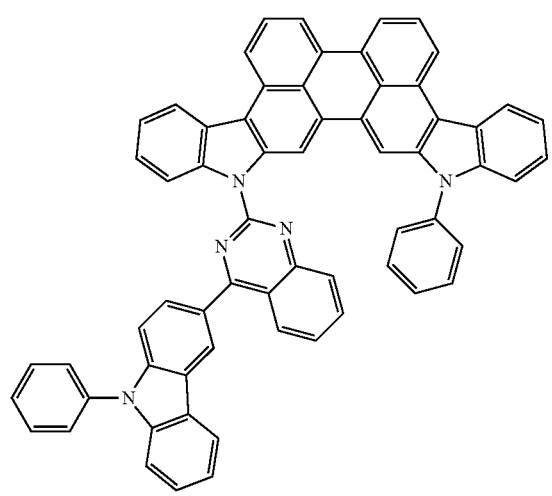
-continued
2-15
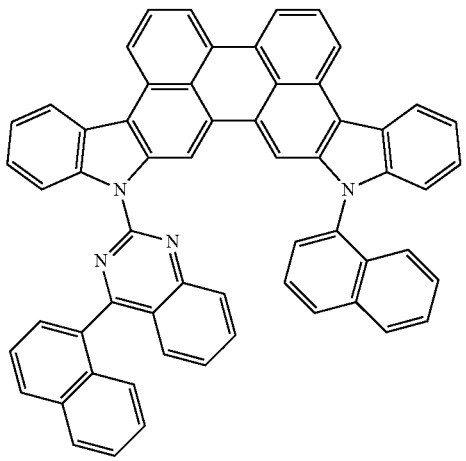
2-16
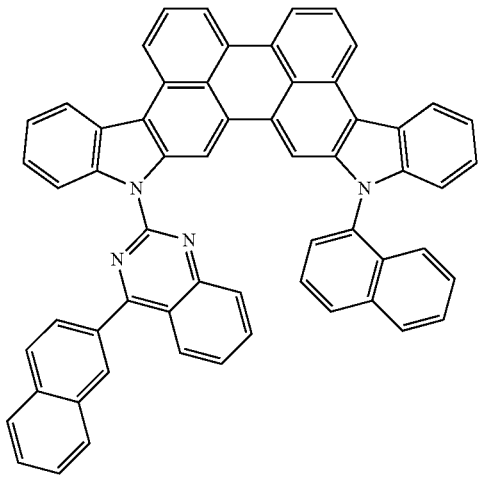
2-17
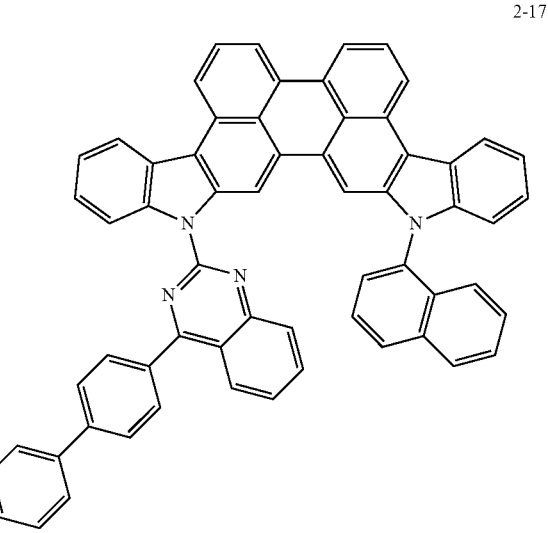

2-18
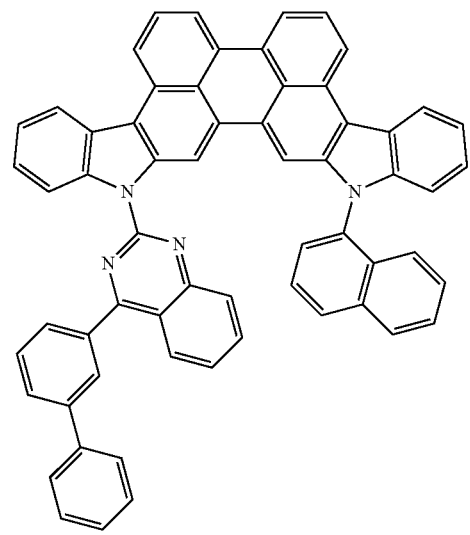
2-19
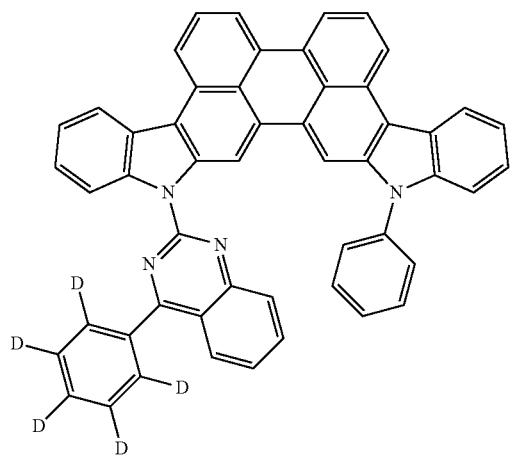
2-20
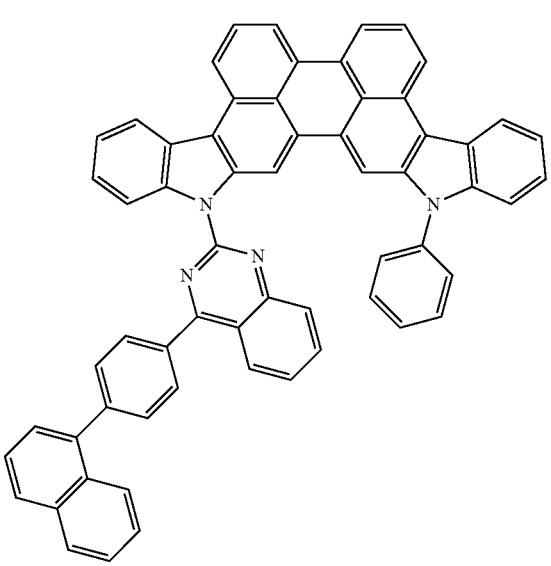
2-21
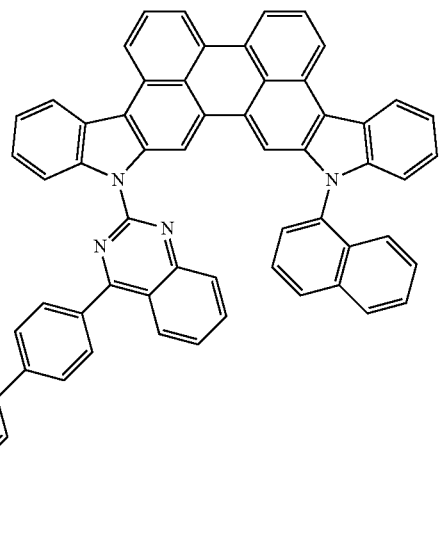
2-22
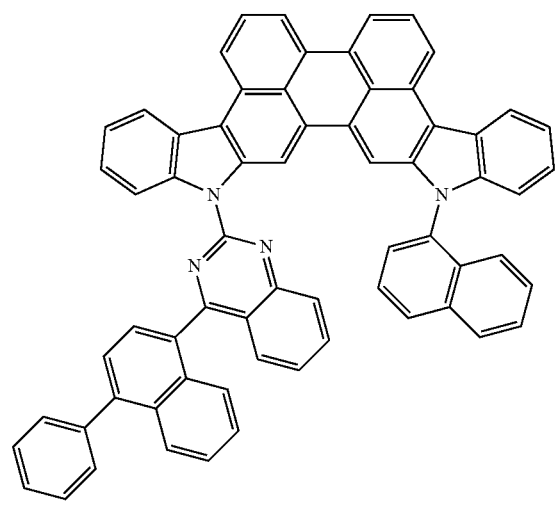
2-23
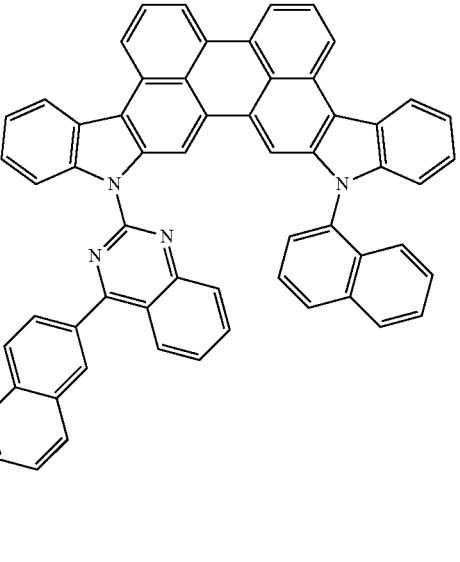

2-24
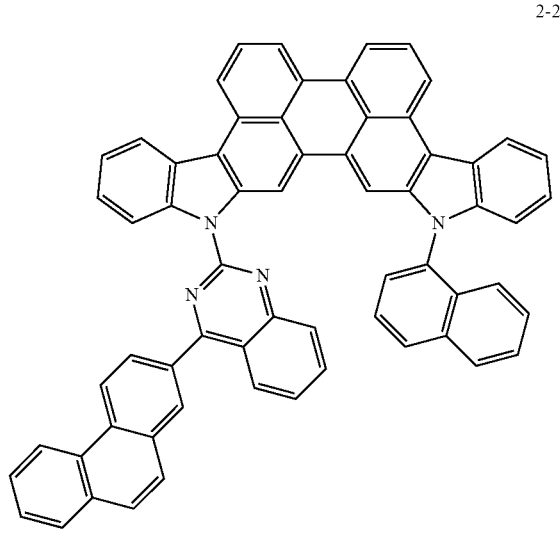
2-25
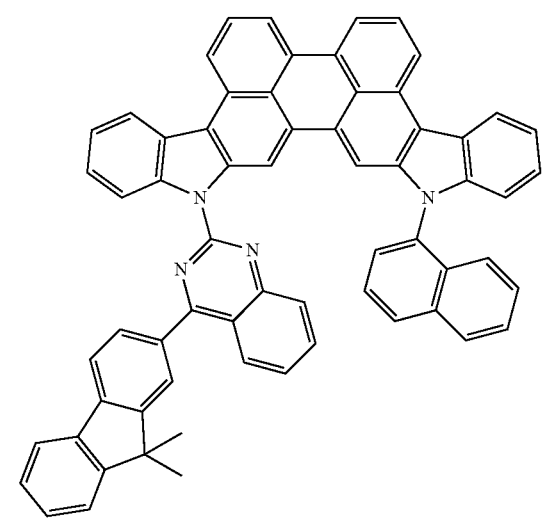
2-26
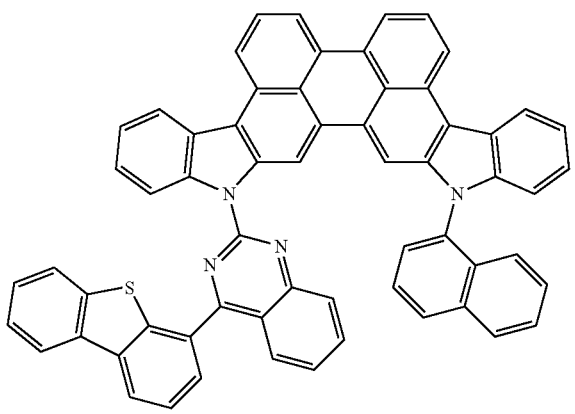
2-27
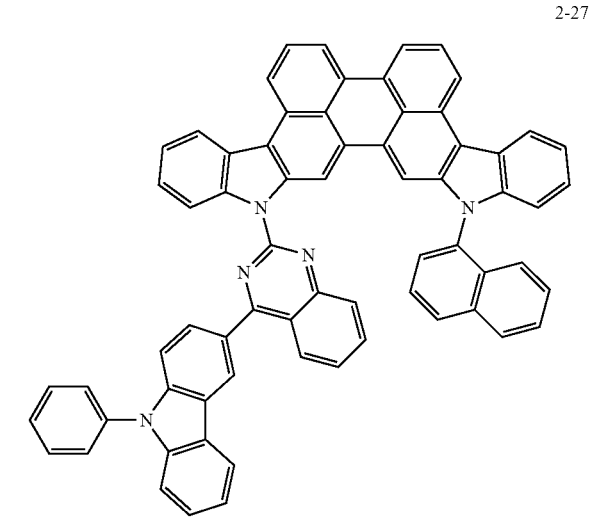
2-28
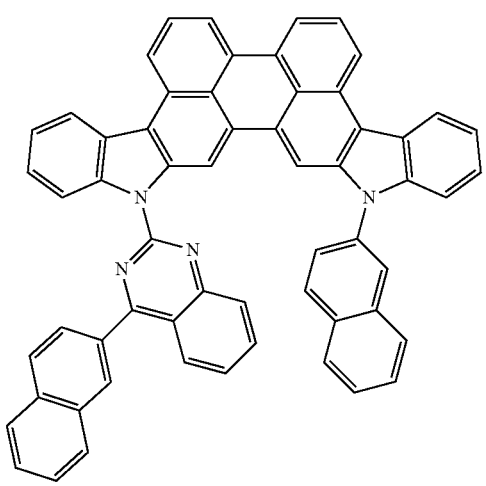
2-29
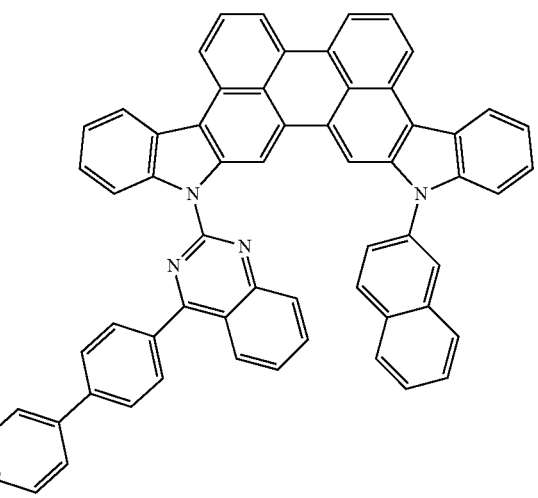

2-30
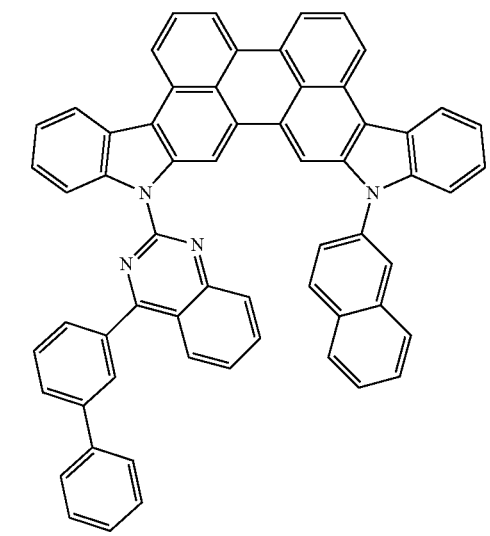
2-31
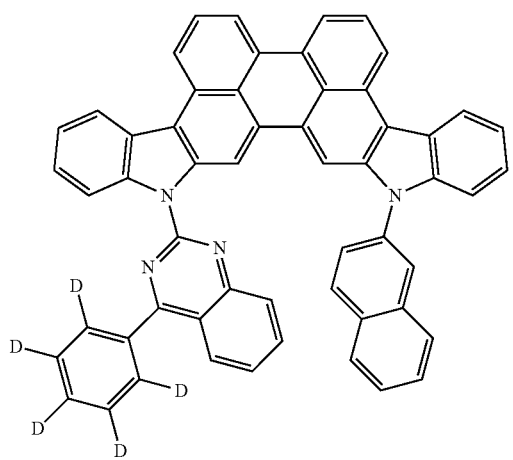
2-32
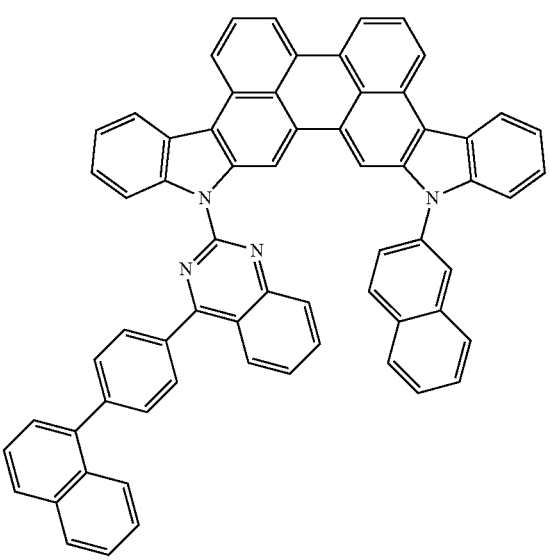
2-33
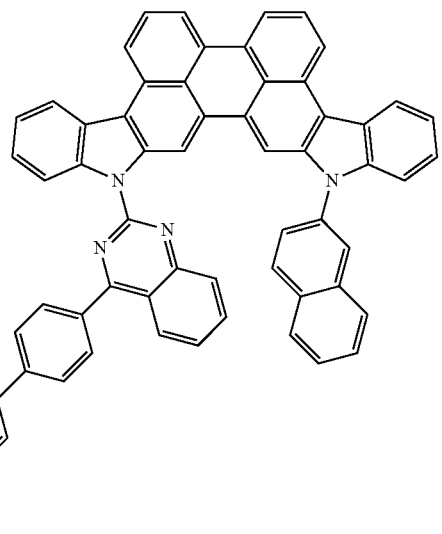
2-34
2-35
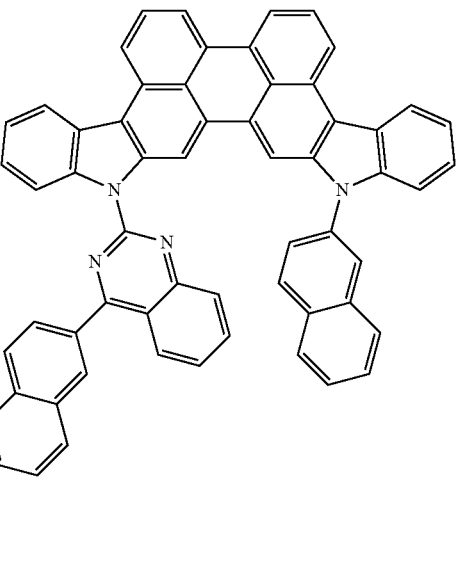

2-36
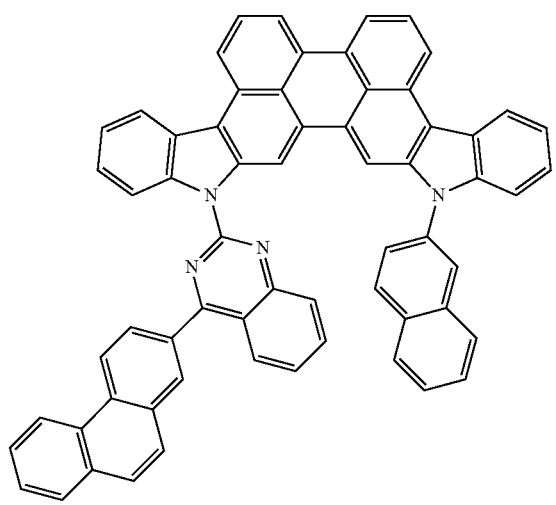
2-37
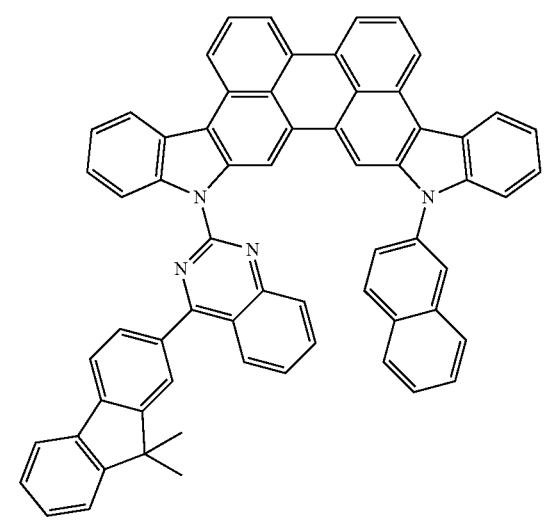
2-38
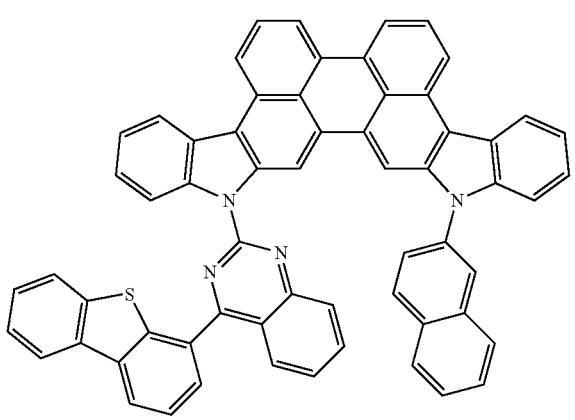
2-39
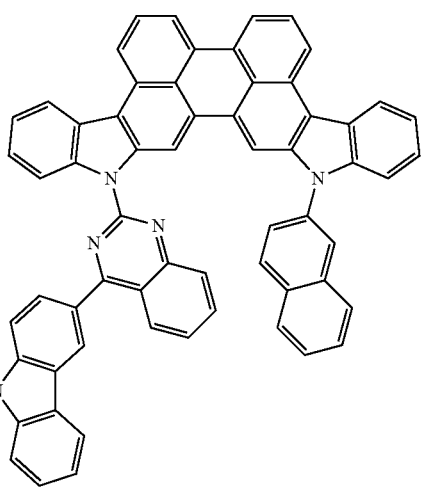
2-40
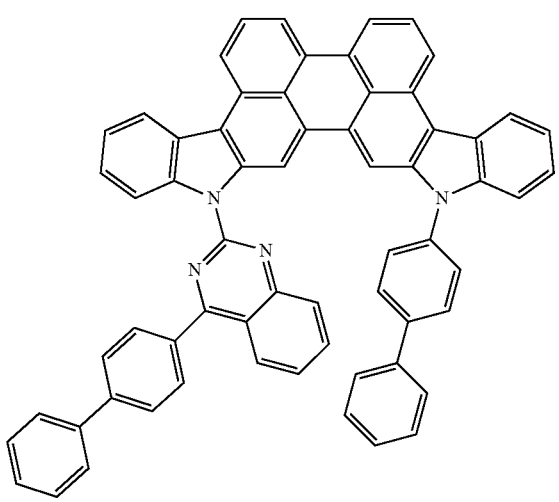
2-41
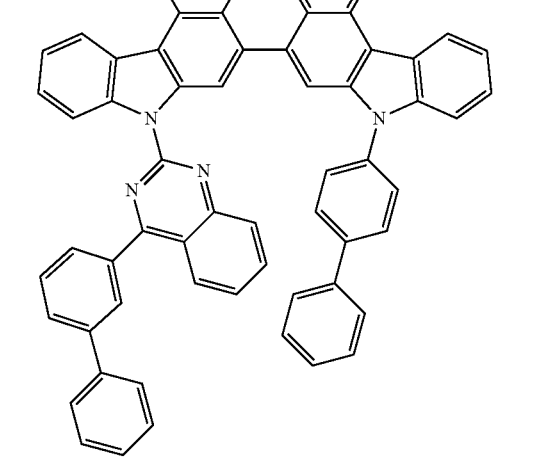

2-42
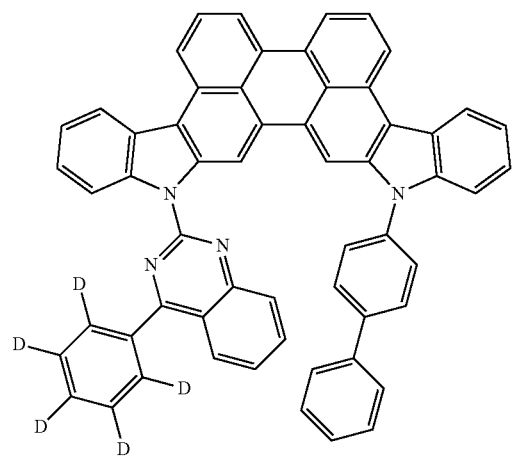
2-45
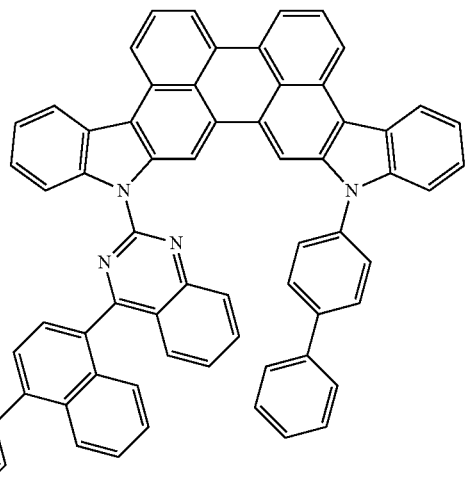
2-43
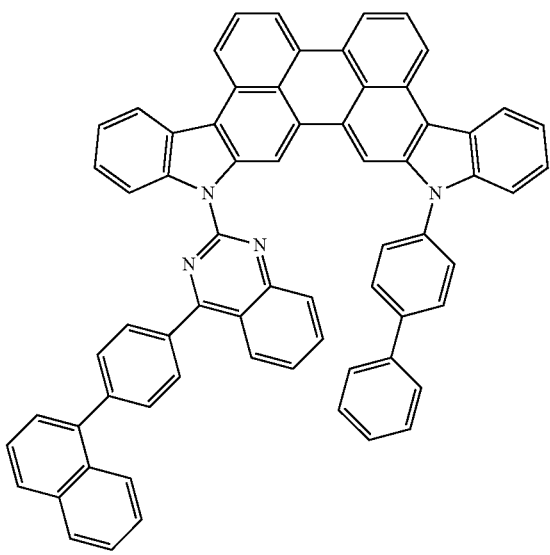
2-46
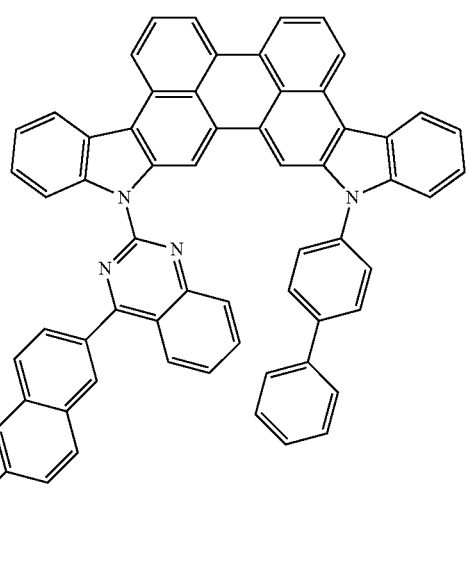
2-44
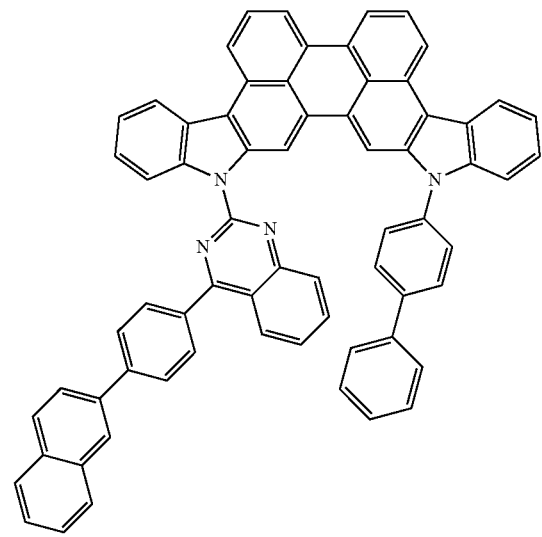
2-47
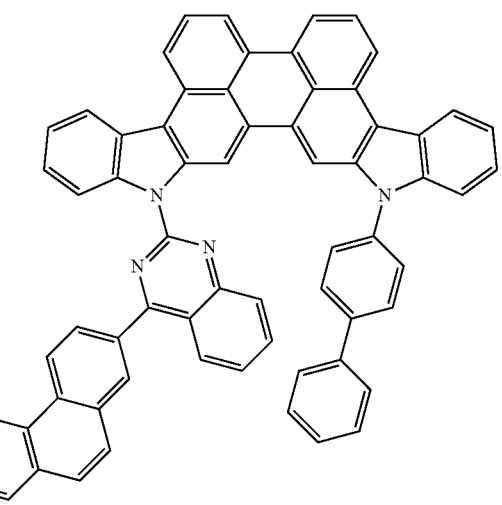

2-48
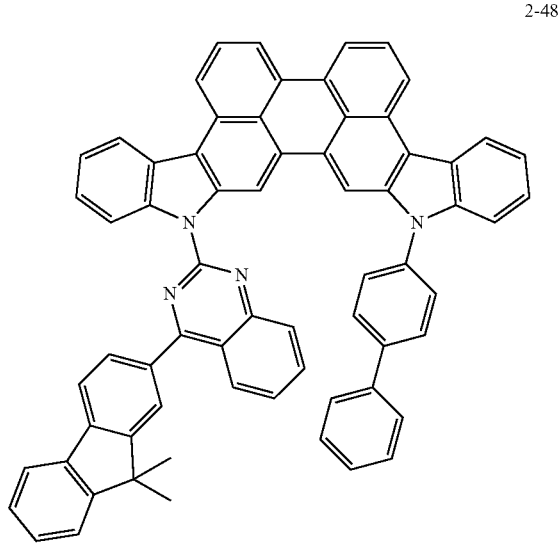
2-51
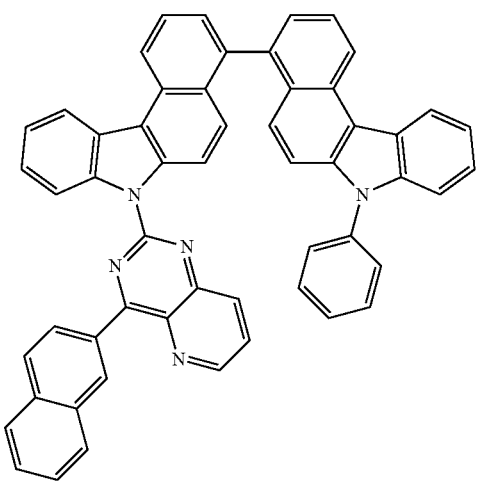
2-49
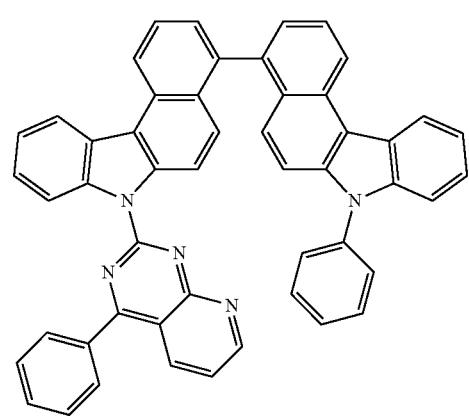
2-52
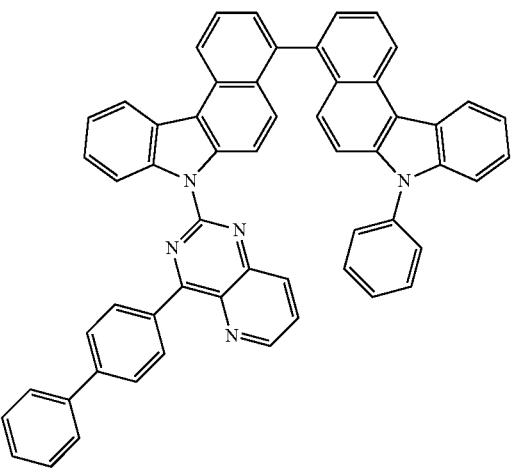
2-50
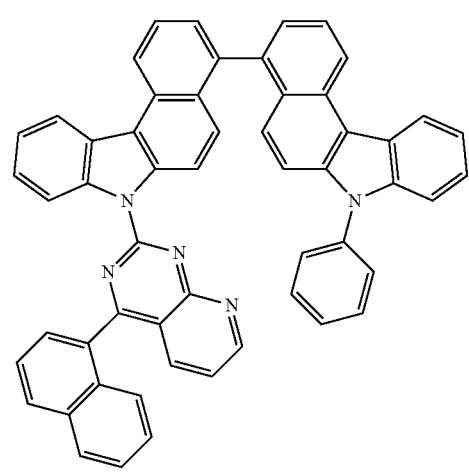
3-1
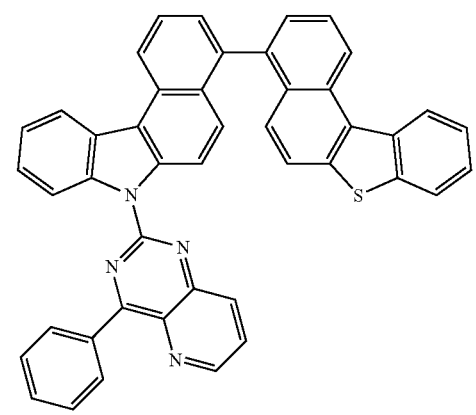

3-2
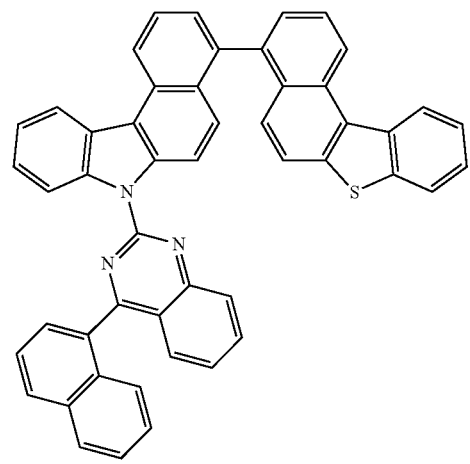
3-3
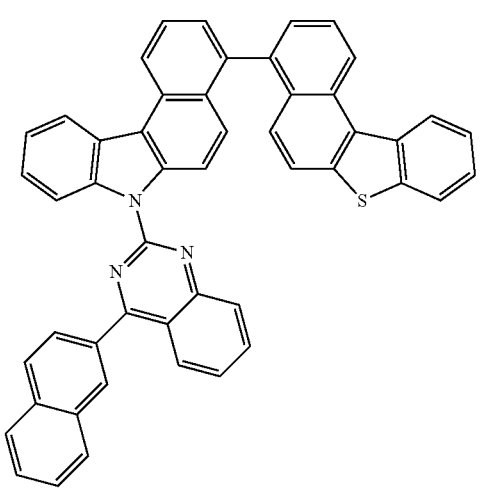
3-4
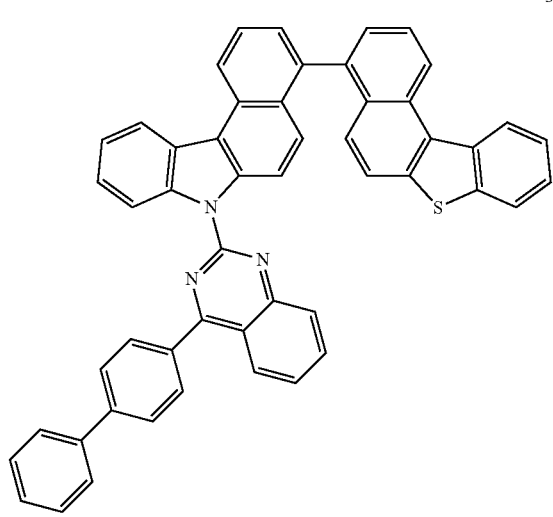
3-5
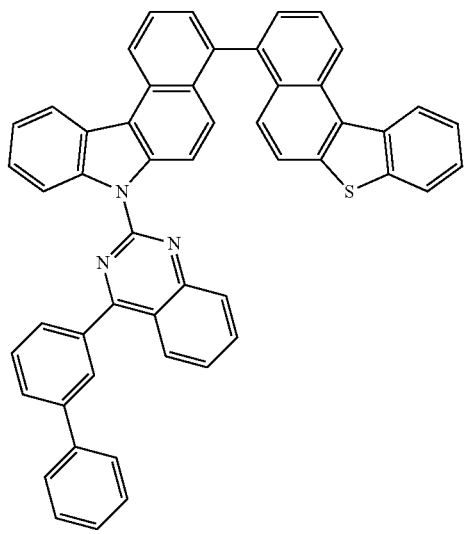
3-6
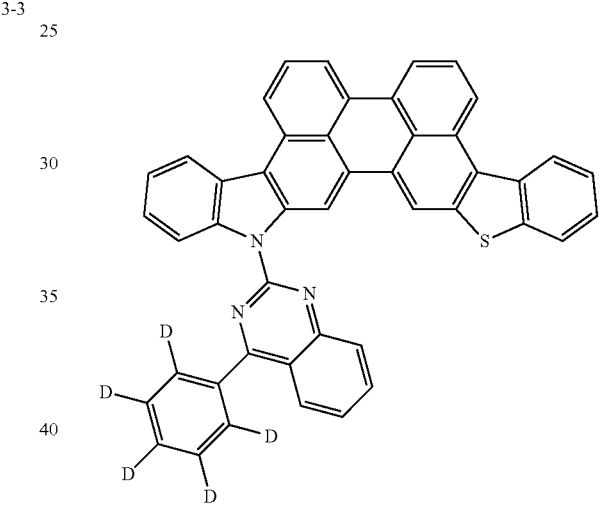
3-7
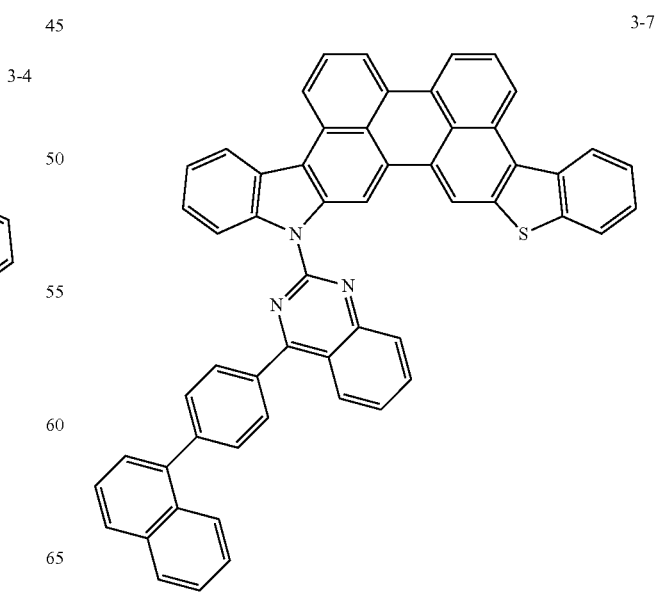

-continued
3-8
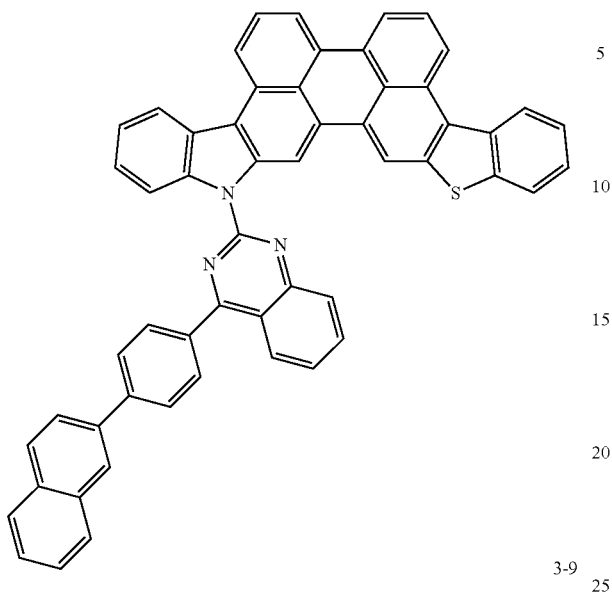
3-9
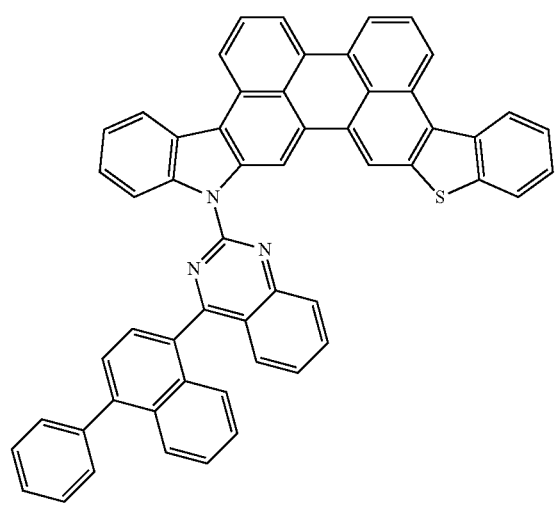
3-10
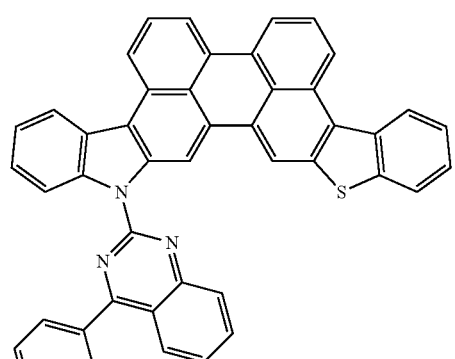
-continued
3-11
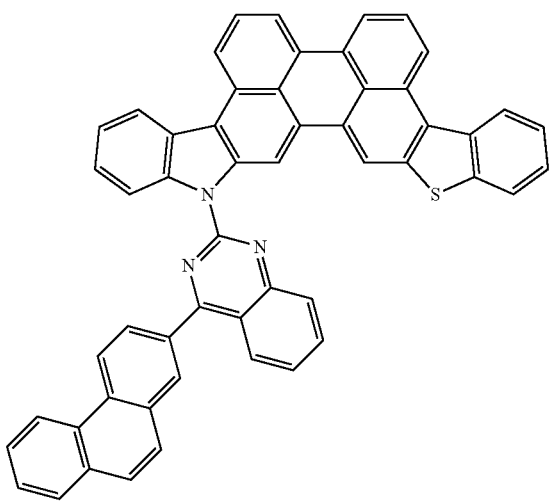
3-12
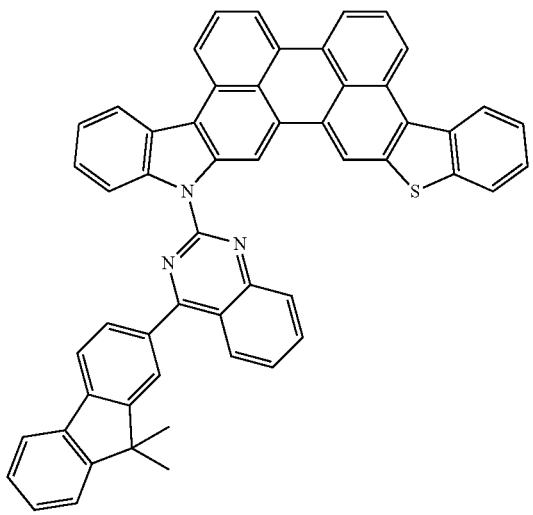
3-13
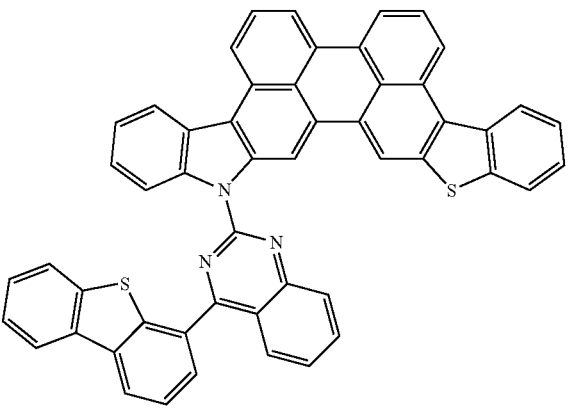

3-14
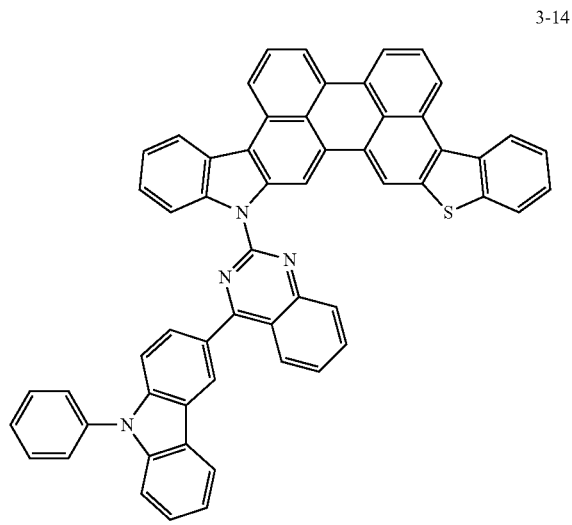
4-1
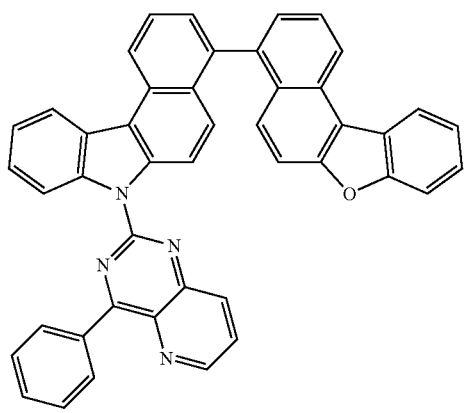
3-15
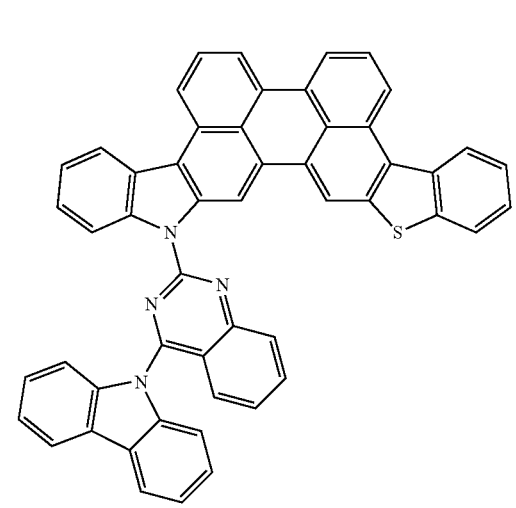
4-2
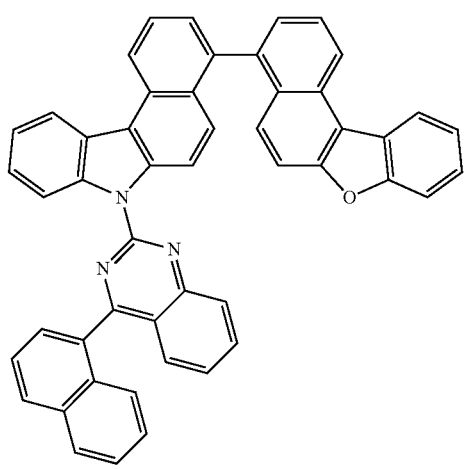
3-16
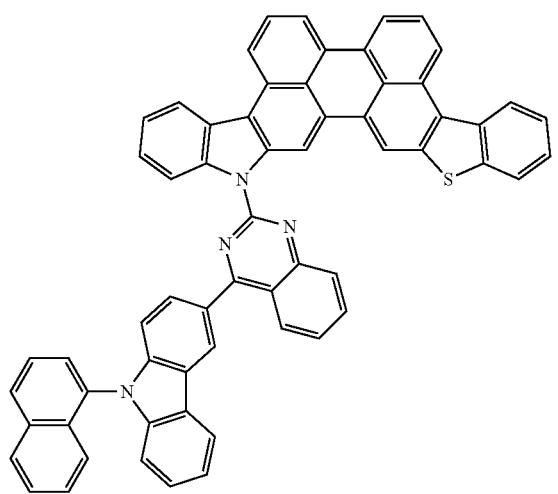
4-3
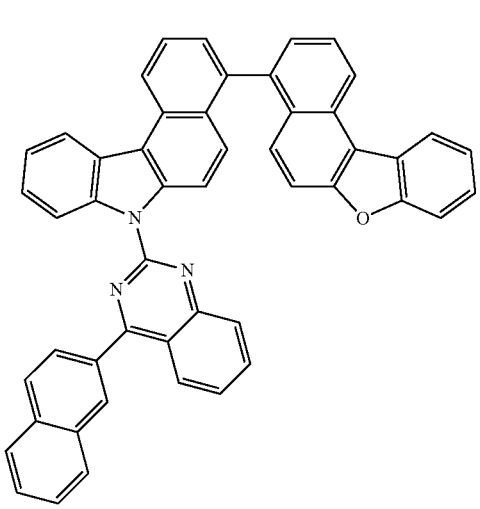

4-4
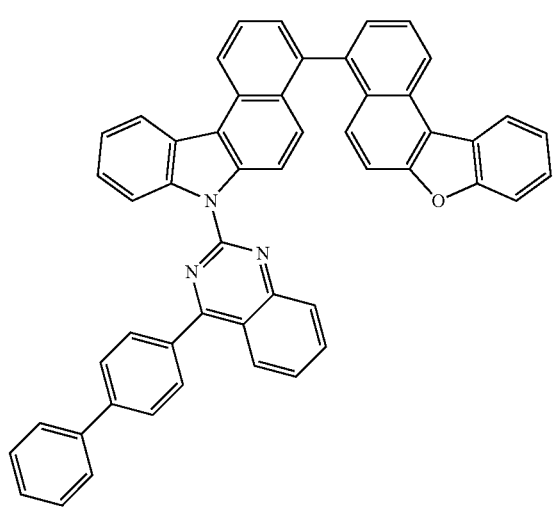
4-5
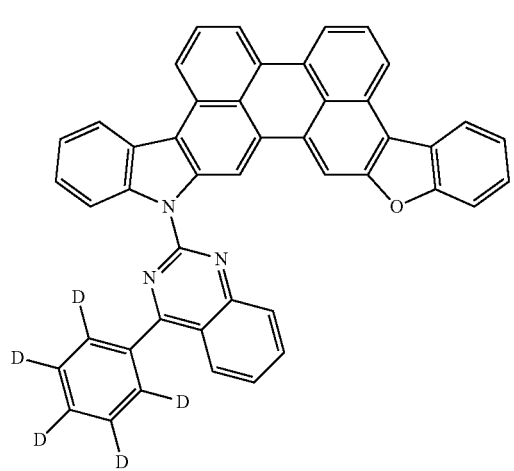
4-6
4-7
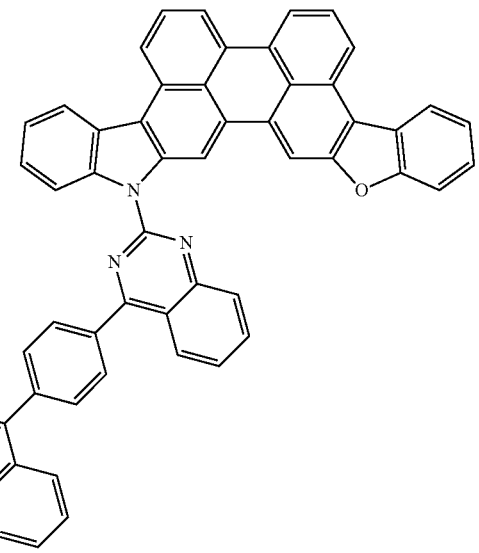
4-8
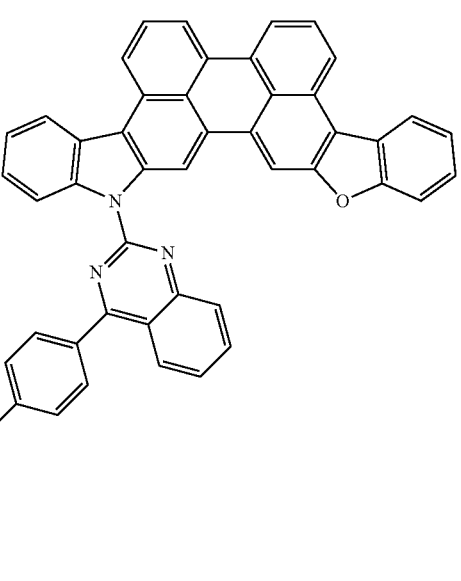
4-9

4-10
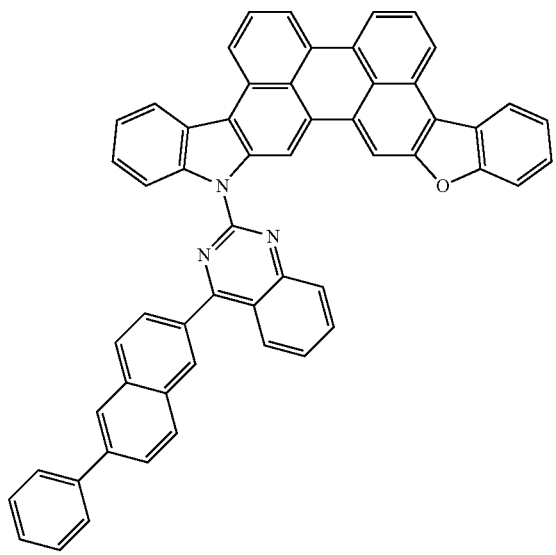
4-11
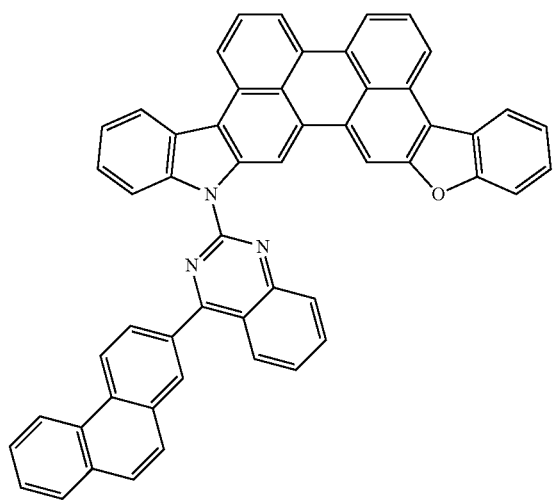
4-12
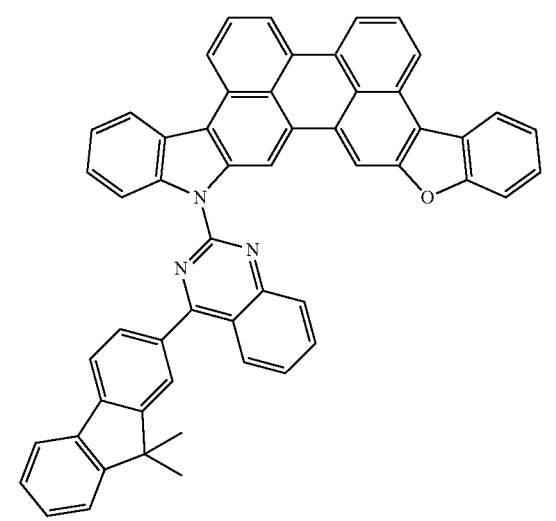
4-13
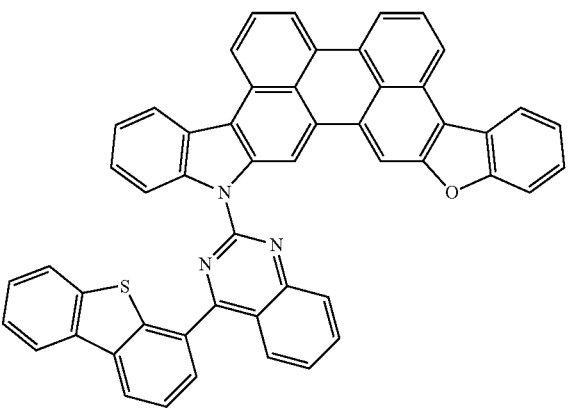
4-14
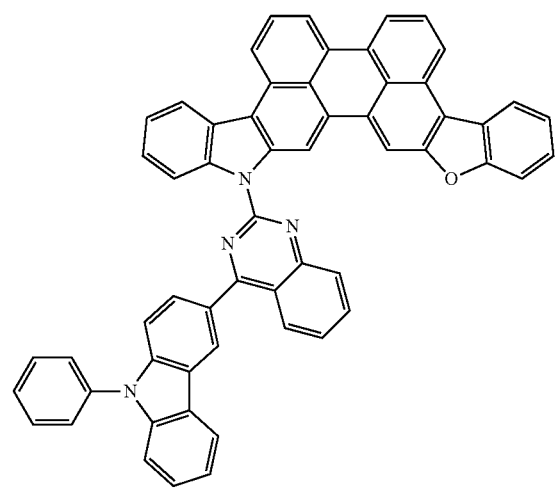
4-15
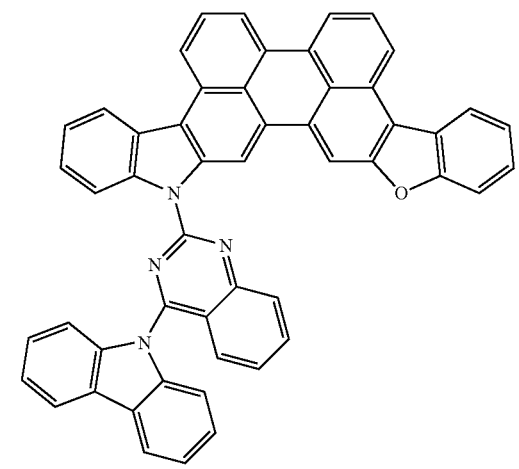

4-16
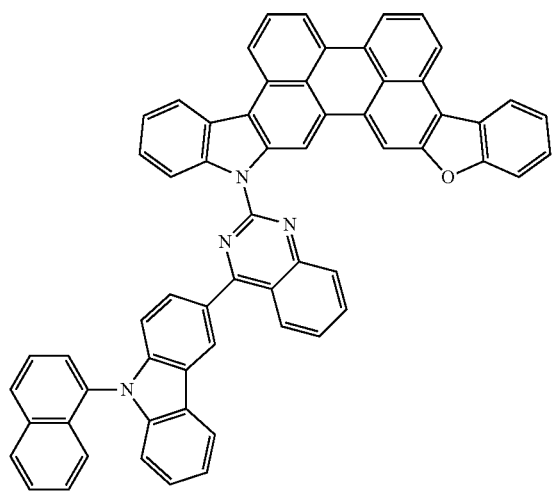
5-1
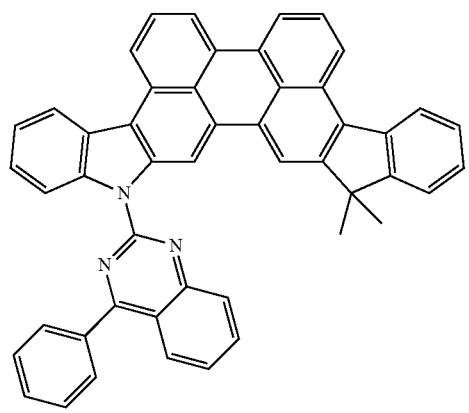
5-2
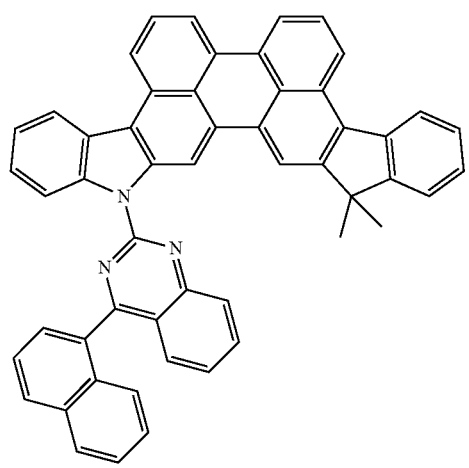
5-3
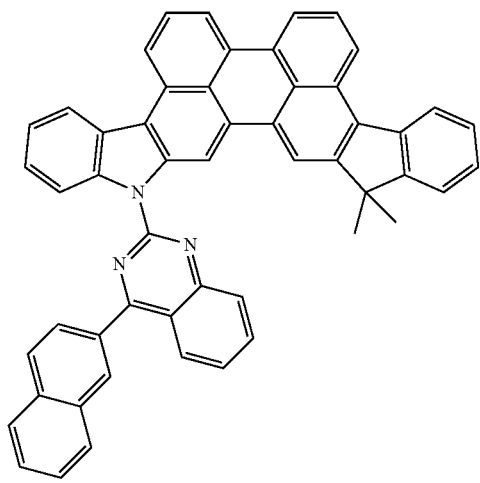
5-4
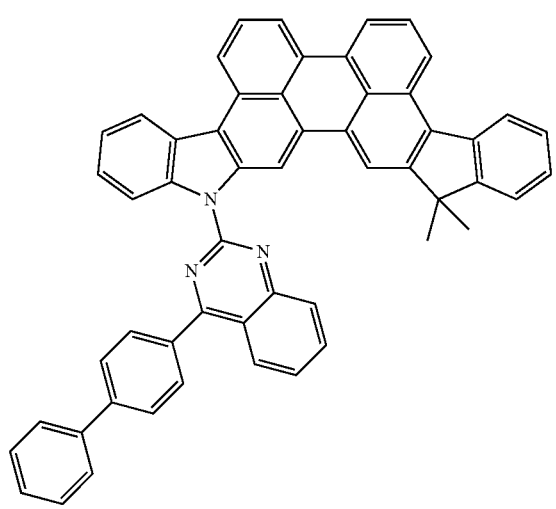
5-5
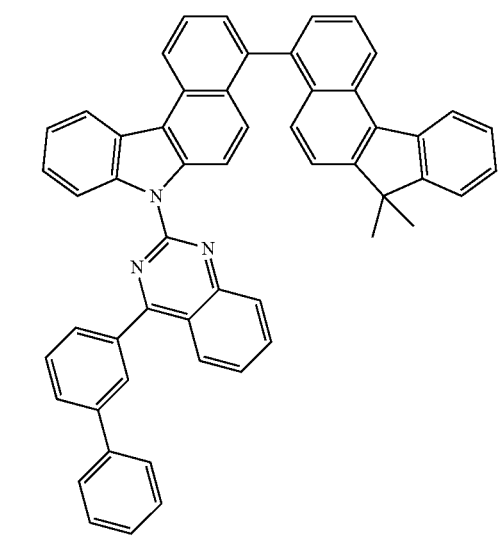

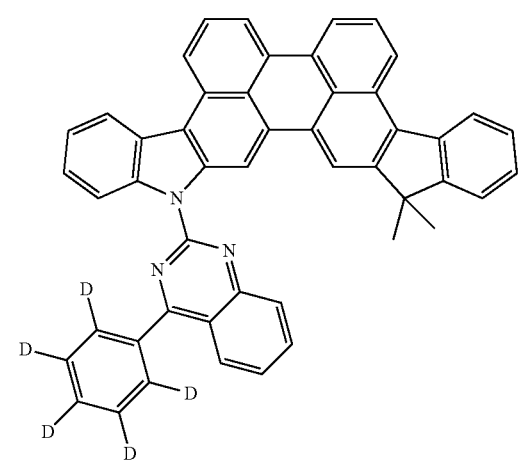
5-6
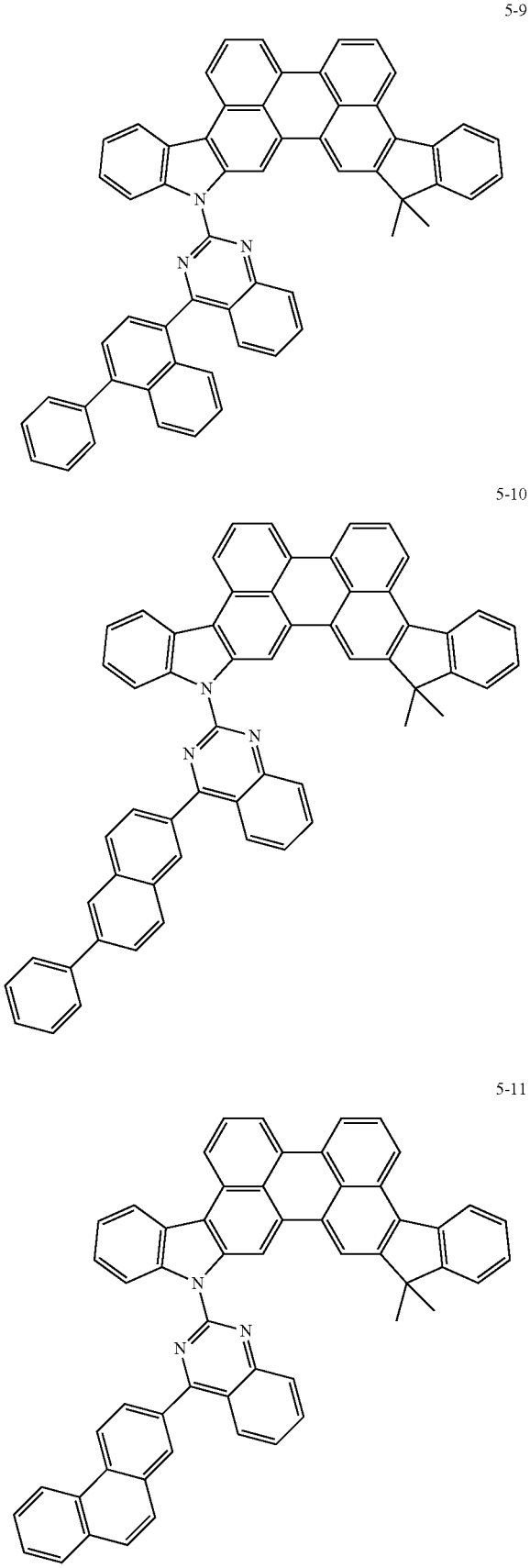
5-9
5-7
5-10
5-8
5-11

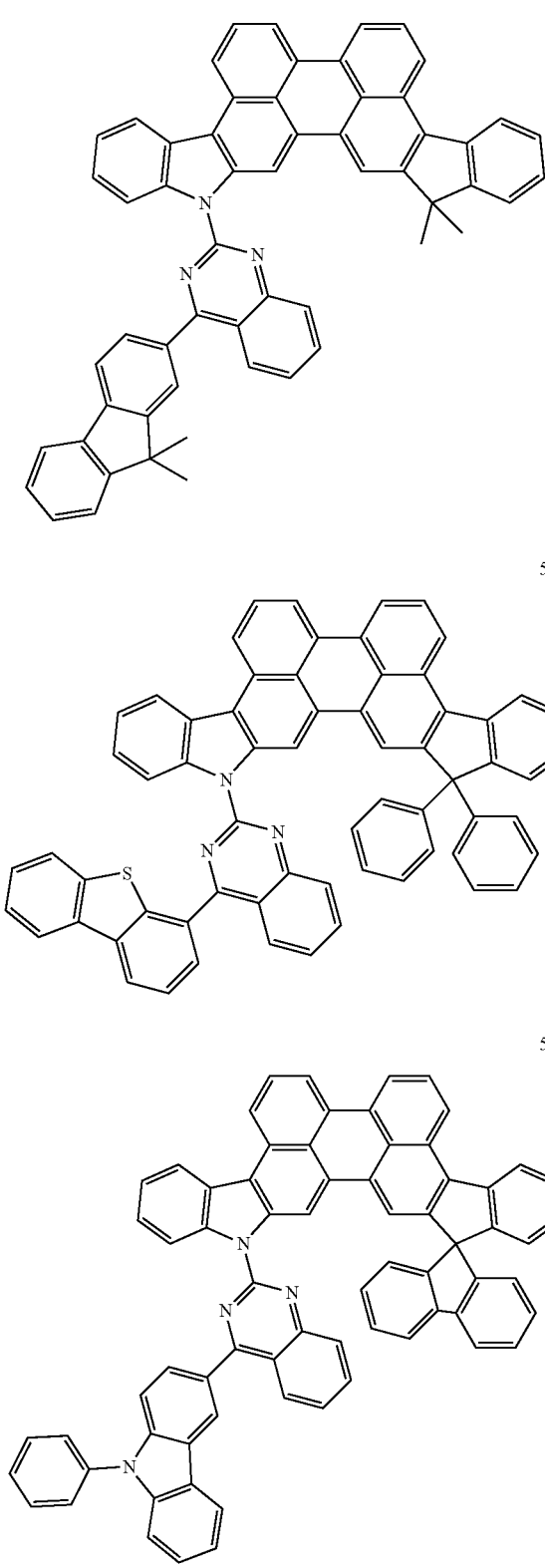

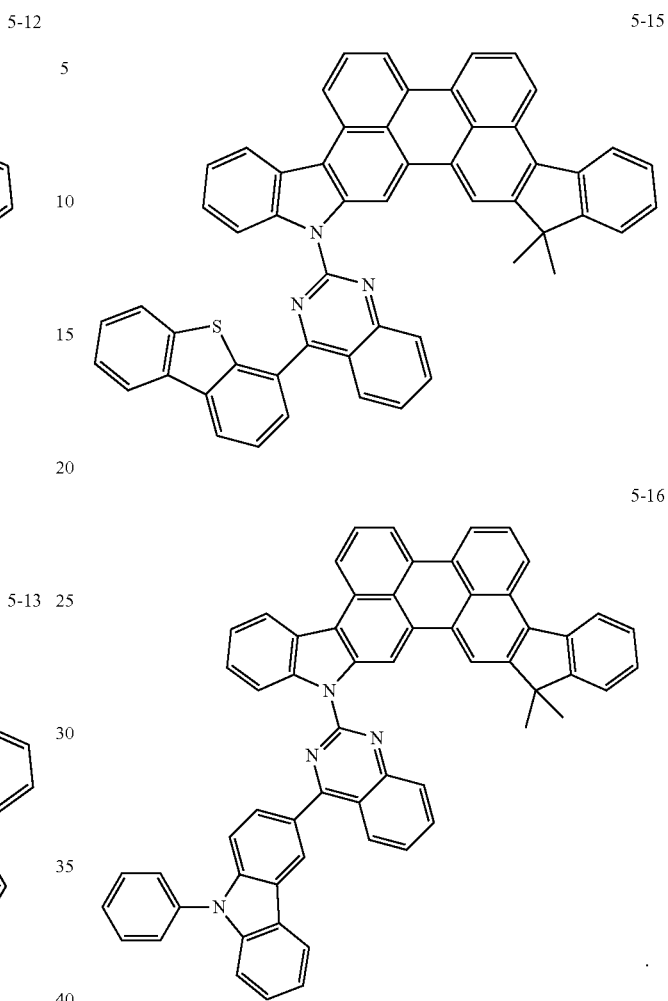

4. An organic electric element comprising a first electrode, a second electrode, and an organic material layer disposed between the first electrode and the second electrode, wherein the organic material layer comprises the compound of claim 1.

5. The organic electric element as claimed in claim 4, wherein the organic material layer is formed by a soluble process.

6. The organic electric element as claimed in claim 4, wherein the organic material layer comprises a light emitting layer.

7. An electronic device comprising a display device, the display device comprising the organic electric element as claimed in claim 4, and a control unit for driving the display device.

8. The electronic device as claimed in claim 7, wherein the organic electric element comprises at least one of an organic light emitting diode, an organic solar cell, an organic photo conductor, an organic transistor, and an element for monochromatic or white illumination.

* * * * *